US010428146B2

(12) United States Patent
Qiu et al.

(10) Patent No.: US 10,428,146 B2
(45) Date of Patent: Oct. 1, 2019

(54) ANTI PD-1 ANTIBODIES

(71) Applicant: CB Therapeutics, Inc., Santa Clara, CA (US)

(72) Inventors: Junzhuan Qiu, Santa Clara, CA (US); Ziyong Sun, Santa Clara, CA (US); Jiping Zha, Santa Clara, CA (US)

(73) Assignee: CB Therapeutics, Inc., Santa Clara, CA (US)

( * ) Notice: Subject to any disclaimer, the term of this patent is extended or adjusted under 35 U.S.C. 154(b) by 50 days.

(21) Appl. No.: 15/328,225

(22) PCT Filed: Jul. 22, 2015

(86) PCT No.: PCT/US2015/041575
§ 371 (c)(1),
(2) Date: Jan. 23, 2017

(87) PCT Pub. No.: WO2016/014688
PCT Pub. Date: Jan. 28, 2016

(65) Prior Publication Data
US 2017/0267762 A1    Sep. 21, 2017

(30) Foreign Application Priority Data

Jul. 22, 2014    (WO) ................ PCT/CN2014/082721

(51) Int. Cl.
C07K 16/28         (2006.01)
C12N 5/0783        (2010.01)
A61K 39/00         (2006.01)

(52) U.S. Cl.
CPC ........ *C07K 16/2818* (2013.01); *C12N 5/0636* (2013.01); *A61K 2039/505* (2013.01); *C07K 2317/24* (2013.01); *C07K 2317/33* (2013.01); *C07K 2317/56* (2013.01); *C07K 2317/565* (2013.01); *C07K 2317/73* (2013.01); *C07K 2317/74* (2013.01); *C07K 2317/76* (2013.01); *C07K 2317/92* (2013.01); *C07K 2319/30* (2013.01); *C07K 2319/32* (2013.01); *C12N 2501/599* (2013.01)

(58) Field of Classification Search
None
See application file for complete search history.

(56) References Cited

U.S. PATENT DOCUMENTS

| | | |
|---|---|---|
| 5,225,539 A | 7/1993 | Winter |
| 5,624,821 A | 4/1997 | Winter et al. |
| 5,629,204 A | 5/1997 | Honjo et al. |
| 5,648,260 A | 7/1997 | Winter et al. |
| 5,698,520 A | 12/1997 | Honjo et al. |
| 5,994,514 A | 11/1999 | Jardieu et al. |
| 6,165,745 A | 12/2000 | Ward et al. |
| 6,194,551 B1 | 2/2001 | Idusogie et al. |
| 6,528,624 B1 | 3/2003 | Idusogie et al. |
| 6,632,927 B2 | 10/2003 | Adair et al. |
| 6,737,056 B1 | 5/2004 | Presta |
| 6,808,710 B1 | 10/2004 | Wood et al. |
| 6,936,704 B1 | 8/2005 | Freeman et al. |
| 7,029,674 B2 | 4/2006 | Carreno et al. |
| 7,038,013 B2 | 5/2006 | Freeman et al. |
| 7,101,550 B2 | 9/2006 | Wood et al. |
| 7,122,637 B2 | 10/2006 | Presta |
| 7,297,775 B2 | 11/2007 | Idusogie et al. |
| 7,317,091 B2 | 1/2008 | Lazar et al. |
| 7,332,581 B2 | 2/2008 | Presta |
| 7,335,742 B2 | 2/2008 | Presta |
| 7,355,008 B2 | 4/2008 | Stavenhagen et al. |
| 7,364,731 B2 | 4/2008 | Idusogie et al. |
| 7,371,826 B2 | 5/2008 | Presta |
| 7,414,171 B2 | 8/2008 | Honjo et al. |
| 7,416,726 B2 | 8/2008 | Ravetch |
| 7,488,802 B2 | 2/2009 | Collins et al. |
| 7,563,869 B2 | 7/2009 | Honjo et al. |
| 7,595,048 B2 | 9/2009 | Honjo et al. |
| 7,597,889 B1 | 10/2009 | Armour et al. |
| 7,608,429 B2 | 10/2009 | Reilly et al. |
| 7,635,757 B2 | 12/2009 | Freeman et al. |
| 7,638,492 B2 | 12/2009 | Wood et al. |
| 7,655,783 B2 | 2/2010 | Reilly et al. |
| 7,670,600 B2 | 3/2010 | Dall'Acqua et al. |
| 7,741,072 B2 | 6/2010 | Idusogie et al. |
| 7,790,858 B2 | 9/2010 | Presta |
| 7,851,598 B2 | 12/2010 | Davis |
| 7,863,419 B2 | 1/2011 | Taylor et al. |
| 7,943,743 B2 | 5/2011 | Korman et al. |
| 7,998,479 B2 | 8/2011 | Honjo et al. |

(Continued)

FOREIGN PATENT DOCUMENTS

| | | |
|---|---|---|
| AU | 2014201367 A1 | 4/2014 |
| CN | 1687135 A | 10/2005 |

(Continued)

OTHER PUBLICATIONS

Vajdos et al. (J Mol Biol. Jul. 5, 2002;320(2):415-28).*
Brown et al. (J Immunol. May 1996;156(9):3285-91.*
Office Action for European Application No. 15824277.6, dated Nov. 2, 2018, 6 pages.
Extended European Search Report for European Application No. 15829791.1 dated Mar. 28, 2018, 17 pages.
Agata et al., "Expression of the PD-1 antigen on the surface of stimulated mouse T and B lymphocytes." Int Immunol. (1996); 8(5): 765-772.
Ahmadzadeh, M. et al., "Tumor antigen-specific CD8 T cells infiltrating the tumor express high levels of PD-1 and are functionally impaired," Blood. Aug. 20, 2009;114(8):1537-1544. doi: 10.1182/blood-2008-12-195792. Epub May 7, 2009.

(Continued)

*Primary Examiner* — Brian Gangle
(74) *Attorney, Agent, or Firm* — Cooley LLP

(57) ABSTRACT

The present invention relates to antibodies and antigen-binding fragments thereof that bind to PD-1, and to methods of using such antibodies and antigen-binding fragments. For example, the present invention provides humanized anti-PD-1 antibodies and methods of use thereof.

26 Claims, 20 Drawing Sheets
Specification includes a Sequence Listing.

(56) References Cited

U.S. PATENT DOCUMENTS

| | | |
|---|---|---|
| 8,008,449 B2 | 8/2011 | Korman et al. |
| 8,088,905 B2 | 1/2012 | Collins et al. |
| 8,168,179 B2 | 5/2012 | Honjo et al. |
| 8,168,757 B2 | 5/2012 | Finnefrock et al. |
| 8,246,955 B2 | 8/2012 | Honjo et al. |
| 8,354,509 B2 | 1/2013 | Carven et al. |
| 8,617,546 B2 | 12/2013 | Kang et al. |
| 8,728,474 B2 | 5/2014 | Honjo et al. |
| 8,735,553 B1 | 5/2014 | Li et al. |
| 8,779,105 B2 | 7/2014 | Korman et al. |
| 8,911,726 B2 | 12/2014 | Takahashi et al. |
| 8,945,561 B2 | 2/2015 | Davis |
| 9,067,999 B1 | 6/2015 | Honjo et al. |
| 9,073,994 B2 | 7/2015 | Honjo et al. |
| 9,084,776 B2 | 7/2015 | Korman et al. |
| 9,139,653 B1 | 9/2015 | Campbell et al. |
| 9,217,034 B2 | 12/2015 | Li et al. |
| 9,492,540 B2 | 11/2016 | Korman et al. |
| 9,834,606 B2 | 12/2017 | Li et al. |
| 9,988,450 B2 | 6/2018 | Li et al. |
| 2004/0038339 A1 | 2/2004 | Kufer et al. |
| 2005/0064514 A1 | 3/2005 | Stavenhagen et al. |
| 2005/0202028 A1 | 9/2005 | Ledbetter et al. |
| 2006/0121032 A1 | 6/2006 | Dahiyat et al. |
| 2006/0134105 A1 | 6/2006 | Lazar et al. |
| 2006/0263856 A1 | 11/2006 | Gillies et al. |
| 2007/0160597 A1 | 7/2007 | Lazar et al. |
| 2008/0227704 A1 | 9/2008 | Kamens et al. |
| 2009/0068175 A1 | 3/2009 | Lazar et al. |
| 2009/0155256 A1 | 6/2009 | Black et al. |
| 2009/0217401 A1 | 8/2009 | Korman et al. |
| 2010/0151492 A1 | 6/2010 | Ahmed et al. |
| 2010/0197924 A1 | 8/2010 | Gould et al. |
| 2010/0278832 A1 | 11/2010 | Kamogawa et al. |
| 2010/0317834 A1 | 12/2010 | Lazar et al. |
| 2011/0008815 A1 | 1/2011 | Finnefrock et al. |
| 2011/0052584 A1 | 3/2011 | Ravetch |
| 2011/0054151 A1 | 3/2011 | Lazar et al. |
| 2011/0159023 A1 | 6/2011 | Langermann |
| 2011/0171215 A1 | 7/2011 | Davis et al. |
| 2011/0171220 A1 | 7/2011 | Davis et al. |
| 2011/0177088 A1 | 7/2011 | Olive et al. |
| 2011/0195068 A1 | 8/2011 | Langermann et al. |
| 2011/0271358 A1 | 11/2011 | Freeman et al. |
| 2011/0287032 A1 | 11/2011 | Lazar et al. |
| 2012/0076726 A1 | 3/2012 | Gellerfors et al. |
| 2012/0251531 A1 | 10/2012 | Baehner et al. |
| 2013/0004514 A1 | 1/2013 | Zahn et al. |
| 2013/0089541 A1 | 4/2013 | D'Angelo et al. |
| 2013/0133091 A1 | 5/2013 | Korman et al. |
| 2013/0259868 A1 | 10/2013 | Roschke et al. |
| 2013/0291136 A1 | 10/2013 | Freeman et al. |
| 2013/0309250 A1 | 11/2013 | Cogswell et al. |
| 2014/0044738 A1 | 2/2014 | Langermann et al. |
| 2014/0162316 A1 | 6/2014 | O'Neil et al. |
| 2014/0243504 A1 | 8/2014 | Davis et al. |
| 2014/0245468 A1 | 8/2014 | McWhirter et al. |
| 2014/0271642 A1 | 9/2014 | Murphy et al. |
| 2014/0314714 A1 | 10/2014 | Honjo et al. |
| 2014/0341902 A1 | 11/2014 | Maecker et al. |
| 2014/0356363 A1 | 12/2014 | Zhou et al. |
| 2014/0377269 A1 | 12/2014 | Mabry et al. |
| 2015/0044231 A1 | 2/2015 | Kjaergaard et al. |
| 2015/0125444 A1 | 5/2015 | Tsui et al. |
| 2015/0210763 A1 | 7/2015 | Kuramochi et al. |
| 2015/0315274 A1 | 11/2015 | Li et al. |
| 2015/0337053 A1 | 11/2015 | McCarthy et al. |
| 2015/0353631 A1 | 12/2015 | Buttini et al. |
| 2017/0044260 A1 | 2/2017 | Baruah et al. |
| 2017/0204184 A1 | 7/2017 | Zha et al. |
| 2018/0111995 A1 | 4/2018 | Li et al. |
| 2018/0215825 A1 | 8/2018 | Li et al. |
| 2018/0251551 A1 | 9/2018 | Li et al. |

FOREIGN PATENT DOCUMENTS

| | | |
|---|---|---|
| CN | 101104640 A | 1/2008 |
| CN | 101899114 A | 12/2010 |
| RU | 2478400 C2 | 4/2013 |
| WO | WO 1994/029351 | 12/1994 |
| WO | WO 2005/077981 | 8/2005 |
| WO | WO 2006/084015 | 8/2006 |
| WO | WO 2006/121168 | 11/2006 |
| WO | WO 2007/005874 | 1/2007 |
| WO | WO 2007/064972 | 6/2007 |
| WO | WO 2007/067444 | 6/2007 |
| WO | WO 2007/136572 | 11/2007 |
| WO | WO 2008/008315 | 1/2008 |
| WO | WO 2008/083174 A2 | 7/2008 |
| WO | WO 2008/145142 | 12/2008 |
| WO | WO 2008/156712 | 12/2008 |
| WO | WO 2010/036959 | 4/2010 |
| WO | WO 2010/089411 | 8/2010 |
| WO | WO 2010/104949 | 9/2010 |
| WO | WO 2011/110604 A1 | 9/2011 |
| WO | WO 2012/135408 | 10/2012 |
| WO | WO 2012/145493 | 10/2012 |
| WO | WO 2013/079174 | 6/2013 |
| WO | WO 2013/173223 | 11/2013 |
| WO | WO 2013/181452 | 12/2013 |
| WO | WO 2013/181634 | 12/2013 |
| WO | WO 2014/022758 | 2/2014 |
| WO | WO 2014/055897 | 4/2014 |
| WO | WO 2014/066834 | 5/2014 |
| WO | WO 2014/100079 | 6/2014 |
| WO | WO 2015/035606 | 3/2015 |
| WO | WO 2016/000619 | 1/2016 |
| WO | WO 2016/014688 | 1/2016 |
| WO | WO 2016/022630 | 2/2016 |
| WO | WO 2017/011580 A2 | 1/2017 |

OTHER PUBLICATIONS

Amarnath, et al. "The PDL1-PD1 Axis Converts Human Th1 Cells Into Regulatory T Cells." Sci Transl Med. (2011); 3(111): 111ra120.

Araki, K. et al., "Programmed cell death 1-directed immunotherapy for enhancing T-cell function," Cold Spring Harbor Symposia on Quantitative Biology, vol. LXXVIII, 239-247 (2013).

Arlauckas, S.P. et al., "In vivo imaging reveals a tumor-associated macrophage-mediated resistance pathway in anti-PD-1 therapy," Sci. Transl. Med., 9, eaal3604 (May 2017).

Barber, et al. "Restoring function in exhausted CD8 T cells during chronic viral infection." Nature (2006); 439.7077: 682.

Bennett, et al. "Program death-1 engagement upon TCR activation has distinct effects on costimulation and cytokine-driven proliferation: attenuation of ICOS, IL-4, and IL-21, but not CD28, IL-7, and IL-15 responses." The Journal of Immunology (2003); 170(2): 711-718.

Berger, R. et al., "Phase I safety and pharmacokinetic study of CT-011, a humanized antibody interacting with PD-1, in patients with advanced hematologic malignancies," Clinical Cancer Research (2008); 14(10): 3044-3051.

Blank et al. "Blockade of PD-L1 (B7-H1) augments human tumor-specific T cell responses in vitro." International Journal of Cancer (2006); 119(2): 317-327.

Blank, et al. "Interaction of PD-L1 on tumor cells with PD-1 on tumor-specific T cells as a mechanism of immune evasion: implications for tumor immunotherapy." Cancer Immunology, Immunotherapy (2005); 54(4): 307-314.

Brahmer, J. R. et al., "Phase I study of single-agent anti-programmed death-1 (MDX-1106) in refractory solid tumors: safety, clinical activity, pharmacodynamics, and immunologic correlates," J Clin Oncol. (2010); 28(19): 3167-3175.

Brahmer, J. R. et al., "Safety and Activity of Anti-PD-L1 Antibody in Patients with Advanced Cancer," N Engl J Med. (Jun. 28, 2012), 366(26):2455-2465.

Brown, et al. "Blockade of programmed death-1 ligands on dendritic cells enhances T cell activation and cytokine production." The Journal of Immunology (2003); 170(3): 1257-1266.

(56) References Cited

OTHER PUBLICATIONS

Carter, et al. "PD-1: PD-L inhibitory pathway affects both CD4+ and CD8+ T cells and is overcome by IL-2." European Journal of Immunology (2002); 32(3): 634-643.
Chemnitz, et al. "SHP-1 and SHP-2 associate with immunoreceptor tyrosine-based switch motif of programmed death 1 upon primary human T cell stimulation, but only receptor ligation prevents T cell activation." The Journal of Immunology (2004); 173(2): 945-954.
Chia-Jui, Y. et al., Abstract of "Preliminary results of a phase 1A/1B study of BGB-A317, an anti-PD-1 monoclonal antibody (mAb), in patients with advanced hepatocellular carcinoma (HCC)," Annals of Oncology (2017).
Clynes, R. A. et al., "Inhibitory Fc receptors modulate in vivo cytotoxicity against tumor targets," Nat. Med. 6(4):443-446 (Apr. 2000).
Dahan, R. et al., "FcγRs Modulate the Anti-tumor Activity of Antibodies Targeting the PD-1/PD-L1 Axis," Cancer Cell. Sep. 14, 2015;28(3):285-95. doi: 10.1016/j.ccel1.2015.08.004.
Datta-Mannan, et al. "Humanized IgG1 variants with differential binding properties to the neonatal Fc receptor: relationship to pharmacokinetics in mice and primates." Drug Metab Dispos. (2007); 35(1): 86-94.
Dong, et al. "B7-H1 pathway and its role in the evasion of tumor immunity." Journal of Molecular Medicine (2003); 81(5): 281-287.
Dong, et al. "Tumor-associated B7-H1 promotes T-cell apoptosis: a potential mechanism of immune evasion." Nature Medicine (2002); 8(8): 793-800.
Dorfman, D. M. et al., "Programmed death-1 (PD-1) is a marker of germinal center-associated T Cells and angioimmunoblastic T-cell lymphoma," American Journal of Surgical Pathology (2006); 30(7): 802-810.
European Search Report for European Application No. 16167542.6, dated Nov. 14, 2016, 5 pages.
Fife, et al. "Interactions between PD-1 and PD-L1 promote tolerance by blocking the TCR-induced stop signal." Nature Immunolog (2009); 10(11): 1185-1192.
Francisco, et al. "PD-L1 regulates the development, maintenance, and function of induced regulatory T cells." Journal of Experimental Medicine (2009); 206(13): 3015-3029.
Freeman, et al. "Engagement of the PD-1 immunoinhibitory receptor by a novel B7 family member leads to negative regulation of lymphocyte activation." Journal of Experimental Medicine (2000); 192(7): 1027-1034.
Fuller, M. J. et al., "Immunotherapy of chronic hepatitis C virus infection with antibodies against programmed cell death-1 (PD-1)," Proceedings of the National Academy of Sciences (2013); 110(37):15001-15006.
Gelderman, K. A. et al., "Complement function in mAb-mediated cancer immunotherapy," Trends in Immunology (2004); 25(3): 158-164.
Graziani, et al., "Ipilimumab: A novel immunostimulatory monoclonal antibody for the treatment of cancer." Pharmacological Research (2012); 65(1): 9-22.
Hamid, O. et al., "Safety and tumor responses with lambrolizumab (Anti-PD-1) in melanoma," New England Journal of Medicine (2013); 369(2): 134-144.
Hofmeyer, et al. "The PD-1/PD-L1 (B7-H1) pathway in chronic infection-induced cytotoxic T lymphocyte exhaustion." BioMed Research International (2011); vol. 2011, Article ID 451694, 9 pages.
Idusogie, et al. "Mapping of the C1q binding site on rituxan, a chimeric antibody with a human IgG1 Fc." The Journal of Immunology (2000); 164(8): 4178-4184.
International Search Report and Written Opinion for International Application No. PCT/CN2013/083467, dated Jun. 16, 2014, 9 pages.
International Search Report and Written Opinion for International Application No. PCT/CN2015/083066, dated Sep. 24, 2015, 8 pages.
International Preliminary Report on Patentability for International Application No. PCT/US2015/041575, dated Jan. 24, 2017, 8 pages.
International Search Report and Written Opinion for International Application No. PCT/US2015/041575, dated Jan. 6, 2016, 12 pages.
International Preliminary Report on Patentability for International Application No. PCT/US2015/043723, dated Feb. 7, 2017, 9 pages.
International Search Report and Written Opinion for International Application No. PCT/US2015/043723, dated Jan. 6, 2016, 14 pages.
InvivoGen Insight, "IgG-Fc Engineering for Therapeutic Use," Apr./May 2006, 4 pages.
Iwai, et al. "Involvement of PD-L1 on tumor cells in the escape from host immune system and tumor immunotherapy by PD-L1 blockade." Proceedings of the National Academy of Sciences (2002); 99(19): 12293-12297.
James, L. K. et al., "Potential Mechanisms for IgG4 Inhibition of Immediate Hypersensitivity Reactions," Curr Allergy Asthma Rep. 2016; 16: 23. Published online Feb. 18, 2016. doi: 10.1007/s11882-016-0600-2.
Jiao, Yu et al., "Advances in the research of the anti-cancer agent—Raf kinase inhibitor," Strait Pharmaceutical Journal, vol. 19, No. 8, 2007, pp. 1-5 (with English Abstract).
Kettleborough, et al. "Optimization of primers for cloning libraries of mouse immunoglobulin genes using the polymerase chain reaction." European Journal of Immunology (1993); 23(1): 206-211.
Konishi, et al. "B7-H1 expression on non-small cell lung cancer cells and its relationship with tumor-infiltrating lymphocytes and their PD-1 expression." Clinical Cancer Research (2004); 10(15): 5094-5100.
Latchman, et al. "PD-L1-deficient mice show that PD-L1 on T cells, antigen-presenting cells, and host tissues negatively regulates T cells." Proceedings of the National Academy of Sciences of the United States of America (2004); 101(29): 10691-10696.
Latchman, Yvette, et al. "PD-L2 is a second ligand for PD-1 and inhibits T cell activation." Nature immunology (2001); 2(3): 261.
Lee, et al. "Blocking the monocyte chemoattractant protein-1/CCR2 chemokine pathway induces permanent survival of islet allografts through a programmed death-1 ligand-1-dependent mechanism." The Journal of Immunology (2003); 171(12): 6929-6935.
Lund, J. et al., "Multiple interactions of IgG with its core oligosaccharide can modulate recognition by complement and human Fc gamma receptor I and influence the synthesis of its oligosaccharide chains," J Immunol. (1996); 157(11): 4963-4969.
Medzihradszky, et al. "Characterization of site-specific N-glycosylation." Methods Mol Biol. (2008); 446: 293-316.
Moore, et al. "Engineered Fc variant antibodies with enhanced ability to recruit complement and mediate effector functions." MAbs. (2010); 2(2): 181-189.
Mueller, et al. "PD-L1 has distinct functions in hematopoietic and nonhematopoietic cells in regulating T cell responses during chronic infection in mice." The Journal of Clinical Investigation (2010); 120(7): 2508-2515.
Nomi, et al. "Clinical significance and therapeutic potential of the programmed death-1 ligand/programmed death-1 pathway in human pancreatic cancer." Clinical Cancer Research (2007); 13(7): 2151-2157.
Office Action for U.S. Appl. No. 14/736,966, dated Jun. 1, 2017, 18 pages.
Okazaki, et al. "New regulatory co-receptors: inducible co-stimulator and PD-1." Current Opinion in Immunology (2002); 14(6): 779-782.
Okazaki, et al. "PD-1 and PD-1 ligands: from discovery to clinical application." International Immunology (2007); 19(7): 813-824.
Panka, D. J. et al., "Variable region framework differences result in decreased or increased affinity of variant anti-digoxin antibodies," Proc. Natl. Acad. Sci. USA (1988); 85: 3080-3084.
Partial Search Report for European Application No. 15829791.1 dated Nov. 23, 2017, 12 pages.
Presta, L. G. et al., "Engineering therapeutic antibodies for improved function," Biochemical Society Transactions (2002); 30(4): 487-490.
Rudikoff, S. et al., "Single amino acid substitution altering antigen-binding specificity," Proc. Natl. Acad. Sci. USA (1982); 79: 1979-1983.

(56) References Cited

OTHER PUBLICATIONS

Sequence Alignment, 2014, 1 page.
Shields, R. L. et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry (2001); 276(9): 6591-6604.
Smith, K. G. et al., "FcγRIIB in autoimmunity and infection: evolutionary and therapeutic implications," Nat Rev Immunol. (2010); 10(5): 328-343.
Spiekermann, et al. "Receptor-mediated immunoglobulin G transport across mucosal barriers in adult life." Journal of Experimental Medicine (2002); 196(3): 303-310.
Stave, J. W. et al., "Antibody and antigen contact residues define epitope and paratope size and structure," The Journal of Immunology (2013); 191: 1428-1435.
Strebe, et al. "Cloning of variable domains from mouse hybridoma by PCR." Antibody Engineering (2010): 3-14.
Strome, et al. "B7-H1 blockade augments adoptive T-cell immunotherapy for squamous cell carcinoma." Cancer Research (2003); 63(19): 6501-6505.
Supplementary Partial European Search Report for European Application No. 13893636.4, dated Feb. 28, 2017, 13 pages.
Supplementary European Search Report for European Application No. 15824277.6 dated Dec. 15, 2017, 11 pages.
Sznol, M. et al., "Antagonist antibodies to PD-1 and B7-H1 (PD-L1) in the treatment of advanced human cancer," Clinical Cancer Research (2013); 19(5): 1021-1034.
Tai, et al. "Potent in vitro and in vivo activity of an Fc-engineered humanized anti-HM1. 24 antibody against multiple myeloma via augmented effector function." Blood (2012); 119(9): 2074-2082.
Thompson, et al. "PD-1 is expressed by tumor-infiltrating immune cells and is associated with poor outcome for patients with renal cell carcinoma." Clinical Cancer Research (2007); 13(6): 1757-1761.
Thompson, et al. "Tumor B7-H1 is associated with poor prognosis in renal cell carcinoma patients with long-term follow-up." Cancer Research (2006); 66(7): 3381-3385.
Tsushima, et al. "Predominant expression of B7-H1 and its immunoregulatory roles in oral squamous cell carcinoma." Oral Oncology (2006); 42(3): 268-274.
KOIZ16, UniProtKB Accession No. KOIZ16, Uncharacterized protein, Dec. 11, 2013 1-3 [online]. [Retrieved on Nov. 2, 2015]. Retrieved from the internet <URL: http://www.uniprot.org/uniprot/KOIZ 16.txt?version= 10> Entire document, 1 page.
Wang, C. et al., "In Vitro Characterization of the Anti-PD-1 Antibody Nivolumab, BMS-936558, and In Vivo Toxicology in Non-Human Primates," Cancer Immunol Res (2014); 2(9): 846-856.
Wherry, E. J., "T cell exhaustion," Nature Immunology 12(6):492-499 (2011). Published online May 18, 2011.
Wintterle, et al. "Expression of the B7-Related Molecule B7-H1 by Glioma Cells." Cancer Research (2003); 63(21): 7462-7467.
Wong, et al. "Programmed death-1 blockade enhances expansion and functional capacity of human melanoma antigen-specific CTLs." International Immunology(2007); 19(10): 1223-1234.
Wu, H. et al., "Humanization of a murine monoclonal antibody by simultaneous optimization of framework and CDR residues," Journal of Molecular Biology, 294(1):151-162 (Nov. 1999).
Xu, D. et al., "In vitro characterization of five humanized OKT3 effector function variant antibodies," Cell Immunol. (2000); 200(1): 16-26.
Abdiche, et al., "Assessing kinetic and epitopic diversity across orthogonal monoclonal antibody generation platforms." mABs (Feb.-Mar. 2016); 8(2): 264-277.
Boyd and Crowe Jr., "Deep sequencing and human antibody repertoire analysis." Current Opinion in Immunology (Jun. 2016); 40: 103-109. Epub Apr. 8, 2016.
Conroy, et al., "Antibodies: From novel repertoires to defining and refining the structure of biologically important targets." Methods (Mar. 2017); 116: 12-22. Epub Jan. 11, 2017.
Damschroder, et al., "Analysis of human and primate CD2 molecules by protein sequence and epitope mapping with anti-human CD2 antibodies." Mol Immunol. (Aug. 2004); 41(10): 985-1000.
Ferrara, et al., "Recombinant renewable polyclonal antibodies." mABs (2015); 7(1): 32-41.
Khan, et al., "Cross-neutralizing anti-HIV-1 human single chain variable fragments (scFvs) against CD4 binding site and N332 glycan identified from a recombinant phage library." Scientific Reports (2017); Article No. 45163, 12 pages.
Könitzer, et al., "Generation of a highly diverse panel of antagonistic chicken monoclonal antibodies against the GIP receptor." mABs (Apr. 2017); 9(3): 536-549. Epub Jan. 5, 2017.
Lee, et al., "Molecular-level analysis of the serum antibody repertoire in young adults before and after seasonal influenza vaccination." Nat Med. (Dec. 2016); 22(12): 1456-1464. Epub Nov. 7, 2016.
Parola, et al., "Integrating high-throughput screening and sequencing for monoclonal antibody discovery and engineering." Immunology (Jan. 2018); 153(1): 31-41. Epub Oct. 30, 2017.
Roitt, et al., "Antibody Specificity and Affinity". Immunology, Moscow, 2000, Publishing House "Mir", p. 153 (with English summary/abstract of pertinent p. 153), 594 pages.
Sheehan and Marasco, "Phage and Yeast Display." Microbial. Spectr. (2015); 3(1): AID-0028-2014; 17 pages.
Van Regenmortel, Marc H. V., "Development of a Preventive HIV Vaccine Requires Solving Inverse Problems Which Is Unattainable by Rational Vaccine Design." Front Immunol. (Jan. 2018); 8: 2009. eCollection 2017.
Zhou, et al., "Structural Repertoire of HIV-1-Neutralizing Antibodies Targeting the CD4 Supersite in 14 Donors." Cell (Jun. 2015); 161(6): 1280-1292.
Invitation to Pay Additional Fees for International Application No. PCT/US2015/041575, dated Oct. 30, 2015, 3 pages.
Invitation to Pay Additional Fees for International Application No. PCT/US2015/043723, dated Oct. 30, 2015, 3 pages.
Köhler, G., "Immunoglobulin chain loss in hybridoma lines." Proc Natl Acad Sci USA (Apr. 1980); 77(4): 2197-2199.
Ozturk and Palsson, "Loss of antibody productivity during long-term cultivation of a hybridoma cell line in low serum and serum-free media." Hybridoma (Apr. 1990); 9(2): 167-175.

\* cited by examiner

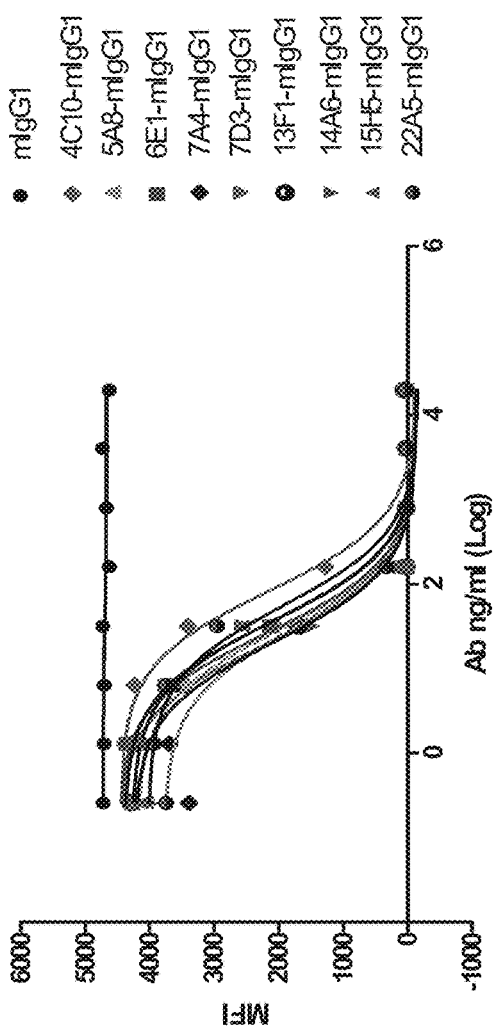

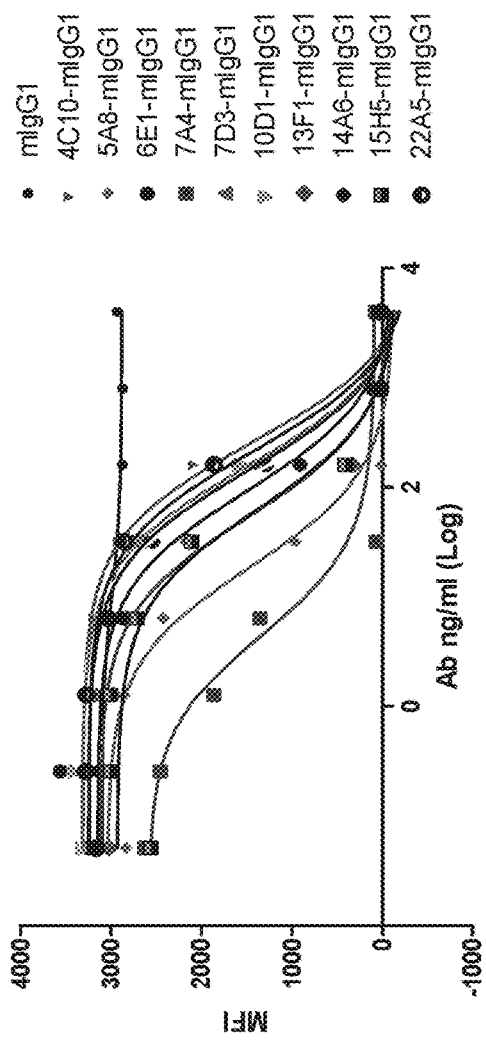

Figure 6
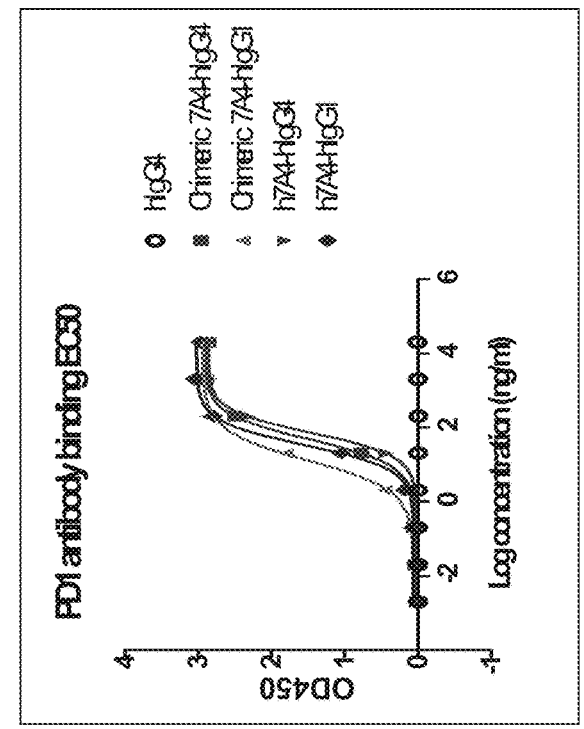
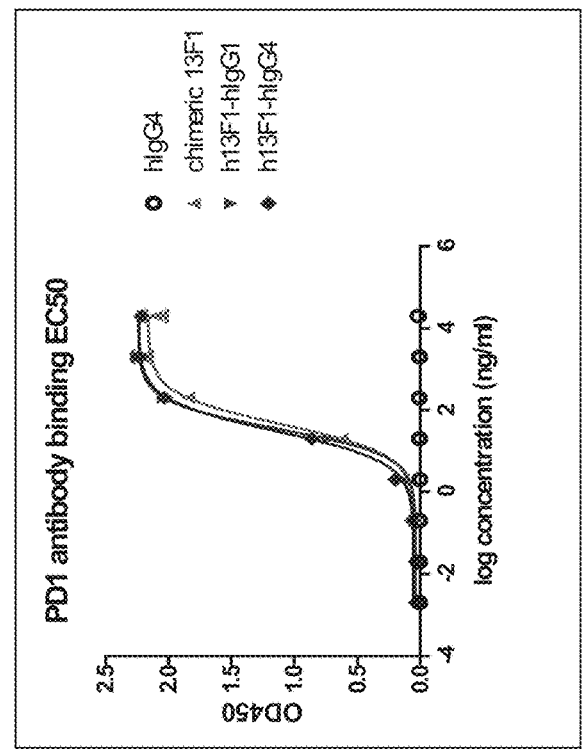

Figure 7
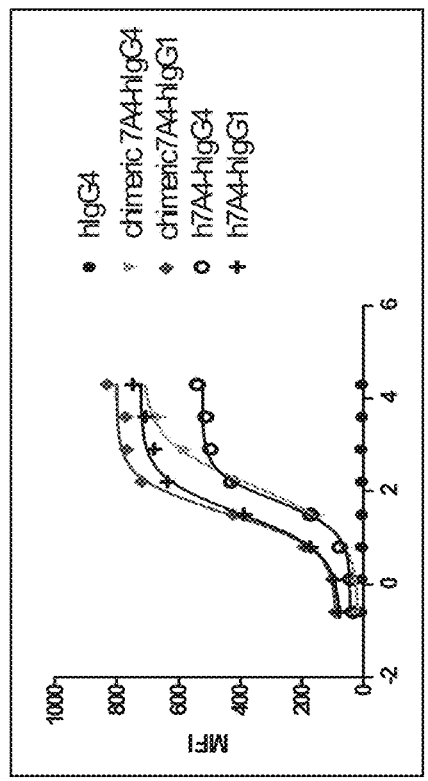
B
| ng/ml | Chimeric 7A4-hIgG4 | Chimeric 7A4 –hIgG1 | h7A4-hIgG4 | h7A4-hIgG1 |
|---|---|---|---|---|
| EC50 | 137.3 | 33.73 | 62.14 | 33.2 |
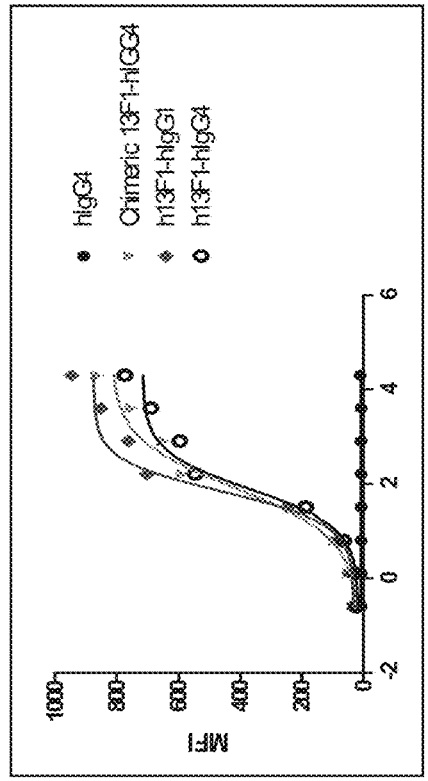
A
| ng/ml | Chimeric 13F1-hIgG4 | h13F1-hIgG1 | h3F1-hIgG4 |
|---|---|---|---|
| EC50 | 81.48 | 66.83 | 76.26 |

Figure 8
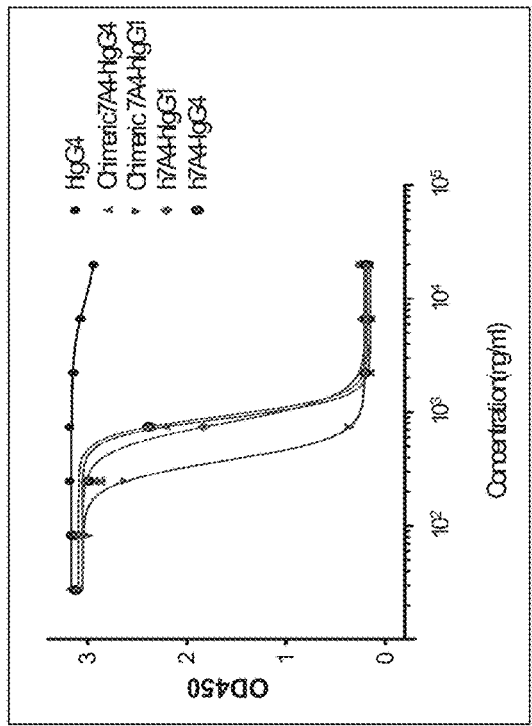
A
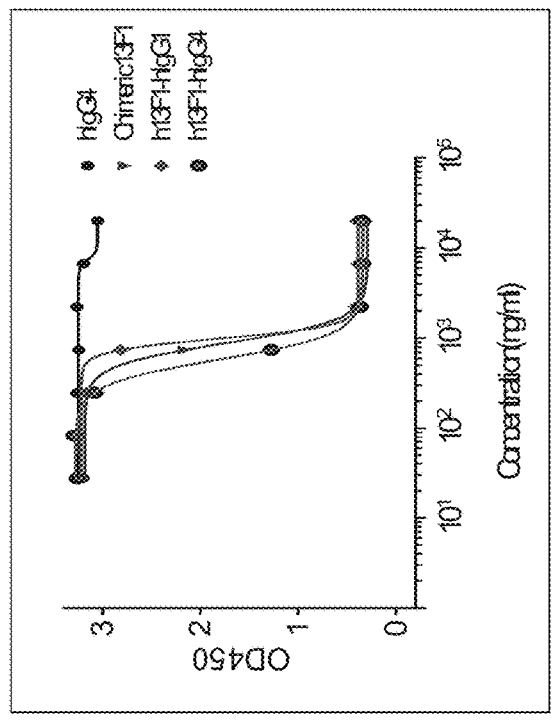
B
| ng/ml | Ch13F1 | h13F1-hIgG1 | h13F1-hIgG4 | Ch 7A4-hIgG4 | Ch 7A4-IgG1 | 7A4-hIgG1 | 7A4-hIgG4 |
|---|---|---|---|---|---|---|---|
| IC50 | 878.4 | 985.4 | 579.0 | 844.6 | 355.8 | 763.0 | 885.8 |
C

ANTI PD-1 ANTIBODIES

CROSS-REFERENCE TO RELATED APPLICATIONS

This application is a U.S. National Stage of International Application No. PCT/US2015/041575, filed Jul. 22, 2015, which claims priority to International Application No. PCT/CN2014/082721, filed Jul. 22, 2014, each of which is incorporated herein by reference in its entirety for all purposes.

FIELD OF THE INVENTION

The present invention relates to antibodies and antigen-binding fragments thereof that bind to PD-1, and to methods of using such antibodies and antigen-binding fragments.

DESCRIPTION OF THE TEXT FILE SUBMITTED ELECTRONICALLY

The content of the text file submitted electronically herewith is incorporated herein by reference in its entirety: A computer readable format copy of the Sequence Listing (filename: CRBI_006_01WO_SeqList_ST25); date recorded: Jul. 14, 2015; file size 147 KB).

BACKGROUND

Programmed death receptor 1 (PD-1) is primarily expressed on lymphocytes and has two ligands, PD-L1 and PD-L2. PD-1 is a 55 kDa protein encoded by a gene Pdcd1 and was shown to down-regulate antigen receptor signaling driven by its ligand's engagement (Freeman et al. (2000) J Exp Med 192:1027-34; Latchman, et. al. (2001) Nat Immunol 2:261-8; Carter et al. (2002) Eur J Immunol 32:634-43). PD-1 belongs to the immunoglobulin superfamily which includes members such as CD28, CTLA-4, ICOS and BTLA. PD-1 is type I transmembrane glycoprotein containing an Ig variable-type (V-type) domain for ligand binding and a cytoplasmic tail for the binding of signaling molecules. PD-1 contains two cytoplasmic tyrosine-based signaling motifs, an immunoreceptor tyrosine-based inhibition motif (ITIM) and an immunoreceptor tyrosine-based switch motif (ITSM). Following T cell stimulation, PD-1 recruits the tyrosine phosphatase SHP-2 to the ITSM motif within its cytoplasmic tail, leading to the dephosphorylation of effector molecules such as CD3 Zeta, PKC theta and ZAP70 that are involved in the CD3 T cell signaling cascade. In contrast, PD-1's ligands (PD-L1 and PD-L2) have two short cytoplasmic regions with no known functions. The ligands have an extracellular region containing IgV- and IgC-like domains and are constitutively expressed or can be induced in a variety of cell types, including non-hematopoietic tissues as well as various tumor types. PD-L1 is not only expressed on B, T, myeloid and dendritic cells (DCs), but also on peripheral cells, like microvascular endothelial cells and non-lymphoid organs like heart, lung etc. In contrast, PD-L2 is only found on macrophages and DCs. The expression pattern of PD-1 ligands is suggestive of a role for PD-1 in maintaining peripheral tolerance and may serve regulate self-reactive T- and B-cell responses in the periphery. To date, numerous studies have shown that interaction of PD-1 with its ligands leads to the inhibition of lymphocyte proliferation in vitro and in vivo. Disruption of the PD-1/PDL1 interaction has been shown to increase T cell proliferation and promote cytokine production.

Thus, there is an important role for the PD-1/PD-L1 pathway in controlling immune responses. Dysfunction of PD-1/PD-L1 signaling appears to be correlated with initiation and development of diseases such as cancer and viral infection. Analysis of knockout animals has led to the understanding that PD-1 functions mainly in inducing and regulating peripheral tolerance. Thus, therapeutic blockade of the PD-1 pathway would be helpful in overcoming immune tolerance and in the treatment of cancer or infection as well as in boosting immunity during vaccination (either prophylactic or therapeutic). There is a need in the art for improved methods for blocking the PD-1 pathway.

SUMMARY OF THE INVENTION

In one aspect, the present invention provides antibodies and antigen-binding fragments thereof that bind to programmed death receptor 1 (PD-1). In some embodiments, the antibodies and antigen-binding fragments thereof bind to human PD-1. In some embodiments, the antibodies and antigen-binding fragments thereof bind to PD-1 and block binding of PD-L1 and/or PD-L2 to PD-1. In further embodiments, the anti-PD-1 antibodies and fragments thereof bind to PD-1 and disrupt the PD-1/PD-L1 or PD1/PD-L2 pathway. In one embodiment, the antibody or fragment thereof is a murine antibody, a chimeric antibody, a human antibody or a humanized antibody. In one embodiment, the anti-PD-1 antibody or fragment thereof is a monoclonal antibody, scFv, Fab fragment, Fab' fragment, F(ab)' fragment, bispecific antibody, immunoconjugate, or a combination thereof.

In one embodiment, the present invention provides an isolated antibody or fragment thereof comprising one or more CDRs selected from the group consisting of SEQ ID NOs: 19-21, 24-26, 29-31, 34-36, 40-42, 45-47, 50-52, 55-57, 60-62, 65-67, 70-72, 75-77, 80-82, 85-87, 90-92, 95-97, 100-102, 105-107, 110-112, and 115-117.

In one embodiment, the antibody or fragment thereof comprises a light chain CDR1 sequence having at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 24, 34, 45, 55, 65, 75, 85, 95, 105, and 115.

In one embodiment, the antibody or fragment thereof comprises a light chain CDR2 sequence having at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 25, 35, 46, 56, 66, 76, 86, 96, 106, and 116.

In one embodiment, the antibody or fragment thereof comprises a light chain CDR3 sequence having at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 26, 36, 47, 57, 67, 77, 87, 97, 107, and 117.

In one embodiment, the antibody or fragment thereof comprises a heavy chain CDR1 sequence having at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 19, 29, 40, 50, 60, 70, 80, 90, 100, and 110.

In one embodiment, the antibody or fragment thereof comprises a heavy chain CDR2 sequence having at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 20, 30, 41, 51, 61, 71, 81, 91, 101, and 111.

In one embodiment, the antibody or fragment thereof comprises a heavy chain CDR3 sequence having at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 21, 31, 42, 52, 62, 72, 82, 92, 102, and 112.

In one embodiment, the antibody or fragment thereof comprises a light chain CDR1 consisting of an amino acid sequence selected from the group consisting of SEQ ID NOs: 24, 34, 45, 55, 65, 75, 85, 95, 105, and 115; a light chain CDR2 consisting of an amino acid sequence selected from the group consisting of SEQ ID NOs: 25, 35, 46, 56, 66, 76, 86, 96, 106, and 116; a light chain CDR3 consisting of an amino acid sequences selected from the group consisting of SEQ ID NOs: 26, 36, 47, 57, 67, 77, 87, 97, 107, and 117; a heavy chain CDR1 consisting of an amino acid sequence selected from the group consisting of SEQ ID NOs: 19, 29, 40, 50, 60, 70, 80, 90, 100, and 110; a heavy chain CDR2 consisting of an amino acid sequence selected from the group consisting of SEQ ID NOs: 20, 30, 41, 51, 61, 71, 81, 91, 101, and 111 and a heavy chain CDR3 consisting of an amino acid sequence selected from the group consisting of SEQ ID NOs: 21, 31, 42, 52, 62, 72, 82, 92, 102, and 112.

In one embodiment, the antibody or fragment thereof binds PD-1 and comprises a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 24, 25, and 26, respectively; and a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 19, 20, and 21, respectively. In a further embodiment, the antibody or antibody fragment thereof comprises a light chain CDR1, CDR2, and CDR3 according to SEQ ID NOs: 24, 25, and 26, respectively, and a heavy chain CDR1, CDR2, and CDR3 according to SEQ ID NOs: 19, 20, and 21, respectively.

In one embodiment, the antibody or fragment thereof binds PD-1 and comprises a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 34, 35, and 36, respectively; and a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 29, 30, and 31, respectively. In a further embodiment, the antibody or antibody fragment thereof comprises a light chain CDR1, CDR2, and CDR3 according to SEQ ID NOs: 34, 35, and 36, respectively, and a heavy chain CDR1, CDR2, and CDR3 according to SEQ ID NOs: 29, 30, and 31, respectively.

In one embodiment, the antibody or fragment thereof binds PD-1 and comprises a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 45, 46, and 47, respectively; and a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 40, 41, and 42, respectively. In a further embodiment, the antibody or antibody fragment thereof comprises a light chain CDR1, CDR2, and CDR3 according to SEQ ID NOs: 45, 46, and 47, respectively, and a heavy chain CDR1, CDR2, and CDR3 according to SEQ ID NOs: 40, 41, and 42, respectively.

In one embodiment, the antibody or fragment thereof binds PD-1 and comprises a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 55, 56, and 57, respectively; and a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 50, 51, and 52, respectively. In a further embodiment, the antibody or antibody fragment thereof comprises a light chain CDR1, CDR2, and CDR3 according to SEQ ID NOs: 55, 56, and 57, respectively, and a heavy chain CDR1, CDR2, and CDR3 according to SEQ ID NOs: 50, 51, and 52, respectively.

In one embodiment, the antibody or fragment thereof binds PD-1 and comprises a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 65, 66, and 67, respectively; and a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 60, 61, and 62, respectively. In a further embodiment, the antibody or antibody fragment thereof comprises a light chain CDR1, CDR2, and CDR3 according to SEQ ID NOs: 65, 66, and 67, respectively, and a heavy chain CDR1, CDR2, and CDR3 according to SEQ ID NOs: 60, 61, and 62, respectively.

In one embodiment, the antibody or fragment thereof binds PD-1 and comprises a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 75, 76, and 77, respectively; and a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 70, 71, and 72, respectively. In a further embodiment, the antibody or antibody fragment thereof comprises a light chain CDR1, CDR2, and CDR3 according to SEQ ID NOs: 75, 76, and 77, respectively, and a heavy chain CDR1, CDR2, and CDR3 according to SEQ ID NOs: 70, 71, and 72, respectively.

In one embodiment, the antibody or fragment thereof binds PD-1 and comprises a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 85, 86, and 87, respectively; and a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 80, 81, and 82, respectively. In a further embodiment, the antibody or antibody fragment thereof comprises a light chain CDR1, CDR2, and CDR3 according to SEQ ID NOs: 85, 86, and 87, respectively, and a heavy chain CDR1, CDR2, and CDR3 according to SEQ ID NOs: 80, 81, and 82, respectively.

In one embodiment, the antibody or fragment thereof binds PD-1 and comprises a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 95, 96, and 97, respectively; and a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 90, 91, and 92, respectively. In a further embodiment, the antibody or antibody fragment thereof comprises a light chain CDR1, CDR2, and CDR3 according to SEQ ID NOs: 95, 96, and 97, respectively, and a heavy chain CDR1, CDR2, and CDR3 according to SEQ ID NOs: 90, 91, and 92, respectively.

In one embodiment, the antibody or fragment thereof binds PD-1 and comprises a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 105, 106, and 107, respectively; and a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 100, 101, and 102, respectively. In a further embodiment, the antibody or antibody fragment thereof comprises a light chain CDR1, CDR2, and CDR3 according to SEQ ID NOs: 105, 106, and 107, respectively, and a heavy chain CDR1, CDR2, and CDR3 according to SEQ ID NOs: 100, 101, and 102, respectively.

In one embodiment, the antibody or fragment thereof binds PD-1 and comprises a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 115, 116, and 117, respectively; and a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 110, 111, and 112, respectively. In a further embodiment, the antibody or antibody fragment thereof comprises a light chain CDR1, CDR2, and CDR3 according to SEQ ID NOs: 115, 116, 117, respectively, and a heavy chain CDR1, CDR2, and CDR3 according to SEQ ID NOs: 110, 111, and 112, respectively.

In one embodiment, the antibody or fragment thereof binds PD-1 and comprises a light chain variable region comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 23, 33, 44, 54, 64, 74, 84, 94, 104, 114, 133, 143, and 152; and a heavy chain variable region comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 18, 28, 39, 49, 59, 69, 79, 89, 99, 109, 131, and 141. In a further embodiment, the isolated antibody or fragment thereof binds PD-1 and comprises a light chain variable region comprising, consisting essentially of, or consisting of an amino acid sequence selected from the group consisting of SEQ ID NOs: 23, 33, 44, 54, 64, 74, 84, 94, 104, 114, 133, 143, and 152; and a heavy chain variable region comprising, consisting essentially of, or consisting of an amino acid sequence selected from the group consisting of SEQ ID NOs: 18, 28, 39, 49, 59, 69, 79, 89, 99, 109, 131, and 141.

In one embodiment, the invention provides anti-PD-1 antibodies that comprise a variable light chain of an antibody selected from the group consisting of 10D1, 4C10, 7D3, 13F1, 15H5, 14A6, 22A5, 6E1, 5A8, 7A4, and 7A4D and a variable heavy chain of an antibody selected from the group consisting of 10D1, 4C10, 7D3, 13F1, 15H5, 14A6, 22A5, 6E1, 5A8, and 7A4. Thus, in one embodiment, the invention provides an antibody or fragment thereof comprising a light chain variable region comprising SEQ ID NO: 23 and a heavy chain variable region comprising SEQ ID NO: 18; a light chain variable region comprising SEQ ID NO: 33 and a heavy chain variable region comprising SEQ ID NO: 28; a light chain variable region comprising SEQ ID NO: 44 and a heavy chain variable region comprising SEQ ID NO: 39; a light chain variable region comprising SEQ ID NO: 54 and a heavy chain variable region comprising SEQ ID NO: 49; a light chain variable region comprising SEQ ID NO: 64 and a heavy chain variable region comprising SEQ ID NO: 59; a light chain variable region comprising SEQ ID NO: 74 and a heavy chain variable region comprising SEQ ID NO: 69; a light chain variable region comprising SEQ ID NO: 84 and a heavy chain variable region comprising SEQ ID NO: 79; a light chain variable region comprising SEQ ID NO: 94 and a heavy chain variable region comprising SEQ ID NO: 89; a light chain variable region comprising SEQ ID NO: 104 and a heavy chain variable region comprising SEQ ID NO: 99; a light chain variable region comprising SEQ ID NO: 114 and a heavy chain variable region comprising SEQ ID NO: 109; a light chain variable region comprising SEQ ID NO: 133 and a heavy chain variable region comprising SEQ ID NO: 131; a light chain variable region comprising SEQ ID NO: 143 and a heavy chain variable region comprising SEQ ID NO: 141; or a light chain variable region comprising SEQ ID NO: 152 and a heavy chain variable region comprising SEQ ID NO: 131.

In one embodiment, the present invention provides a chimeric anti-PD-1 antibody, wherein the antibody comprises a heavy chain having an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs; 119, 121, 125, and 127; and a light chain having an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 123 and 129.

In one embodiment, the present invention provides a humanized anti-PD-1 antibody, wherein the antibody comprises a heavy chain variable region having an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 131 and 141. In another embodiment, the present invention provides a humanized anti-PD-1 antibody, wherein the antibody comprises a light chain variable region having an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 133, 143 and 152.

In another embodiment, the present invention provides a humanized anti-PD-1 antibody, wherein the antibody comprises a heavy chain variable region having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to SEQ ID NO: 131 and a light chain variable region having least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to SEQ ID NO: 133 or 152. In another embodiment, the present invention provides a humanized anti-PD-1 antibody, wherein the antibody comprises a heavy chain variable region having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to SEQ ID NO: 141 and a light chain variable region having least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to SEQ ID NO: 143.

In one embodiment, the present invention provides a humanized anti-PD-1 antibody, wherein the antibody comprises a full heavy chain having an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 135, 137, 145, and 147. In another embodiment, the present invention provides a humanized anti-PD-1 antibody, wherein the antibody comprises a full light chain having an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 139, 149, and 153.

In one embodiment, the present invention provides a humanized anti-PD-1 antibody, wherein the antibody comprises a heavy chain according to SEQ ID NO: 135 and a light chain according to SEQ ID NO: 139. In another embodiment, the present invention provides a humanized anti-PD-1 antibody, wherein the antibody comprises a heavy chain according to SEQ ID NO: 137 and a light chain according to SEQ ID NO: 139. In another embodiment, the present invention provides a humanized anti-PD-1 antibody, wherein the antibody comprises a heavy chain according to SEQ ID NO: 135 and a light chain according to SEQ ID NO: 153. In another embodiment, the present invention provides a humanized anti-PD-1 antibody, wherein the antibody comprises a heavy chain according to SEQ ID NO: 137 and a light chain according to SEQ ID NO: 153. In another embodiment, the present invention provides a humanized anti-PD-1 antibody, wherein the antibody comprises a heavy chain according to SEQ ID NO: 145 and a light chain according to SEQ ID NO: 149. In another embodiment, the present invention provides a humanized anti-PD-1 antibody, wherein the antibody comprises a heavy chain according to SEQ ID NO: 147 and a light chain according to SEQ ID NO: 149. In one embodiment, the present invention provides anti-PD-1 antibodies or fragments thereof that bind to the same epitope on PD-1 as any of the exemplary antibodies provided herein. In one embodiment, the antibodies or fragments thereof compete with any of the exemplary antibodies provided herein for binding to PD-1. Binding to PD-1 may be measured by ELISA, flow cytometry, surface plasmon resonance (SPR) assay, or any other method known in the art.

In one embodiment, the present invention provides anti-PD-1 antibodies and fragments thereof that bind to PD-1 with an affinity of about 1 nM to about 0.01 nM. In a further embodiment, the anti-PD-1 antibodies and fragments thereof provided herein bind to PD-1 with an affinity of from about 0.5 nM to about 0.1 nM. In another embodiment, the anti-PD-1 antibodies and fragments thereof provided herein bind to PD-1 with an affinity of about 1 nM or less. In a further embodiment, the anti-PD-1 antibodies and fragments thereof provided herein bind to PD-1 with an affinity of about 0.75 nM or less. In a further embodiment, the anti-PD-1 antibodies and fragments thereof provided herein bind to PD-1 with an affinity of about 0.5 nM or less. In a further embodiment, the anti-PD-1 antibodies and fragments thereof provided herein bind to PD-1 with an affinity of about 0.25 nM or less. In a further embodiment, the anti-PD-1 antibodies and fragments thereof provided herein bind to PD-1 with an affinity of about 0.2 nM or less. In a further embodiment, the anti-PD-1 antibodies and fragments thereof provided herein bind to PD-1 with an affinity of about 0.15 nM or less. In a further embodiment, the anti-PD-1 antibodies and fragments thereof provided herein bind to PD-1 with an affinity of about 0.1 nM or less. In a further embodiment, the anti-PD-1 antibodies and fragments thereof provided herein bind to PD-1 with an affinity of about 0.075 nM or less. In a further embodiment, the anti-PD-1 antibodies and fragments thereof provided herein bind to PD-1 with an affinity of about 0.05 nM or less. In a further embodiment, the anti-PD-1 antibodies and fragments thereof provided herein bind to PD-1 with an affinity of about 0.025 nM or less. In a further embodiment, the anti-PD-1 antibodies and fragments thereof provided herein bind to PD-1 with an affinity of about 0.02 nM or less. In a further embodiment, the anti-PD-1 antibodies and fragments thereof provided herein bind to PD-1 with an affinity of about 0.015 nM or less. In a further embodiment, the anti-PD-1 antibodies and fragments thereof provided herein bind to PD-1 with an affinity of about 0.01 nM or less. In a further embodiment, the anti-PD-1 antibodies and fragments thereof provided herein bind to PD-1 with an affinity of about 0.0075 or less. In a further embodiment, the anti-PD-1 antibodies and fragments thereof provided herein bind to PD-1 with an affinity of about 0.005 or less.

In one embodiment, the anti PD-1 antibodies and fragments thereof provided herein have a binding EC50 for PD-1 of about 1 ng/mL to about 2000 ng/mL. In a further embodiment, the anti PD-1 antibodies and fragments thereof provided herein have a binding EC50 for PD-1 of about 1 ng/mL to about 1500 ng/mL. In a further embodiment, the anti PD-1 antibodies and fragments thereof provided herein have a binding EC50 for PD-1 of about 1 ng/mL to about 1000 ng/mL. In a further embodiment, the anti PD-1 antibodies and fragments thereof provided herein have a binding EC50 for PD-1 of about 2 ng/mL to about 500 ng/mL. In a further embodiment, the anti PD-1 antibodies and fragments thereof provided herein have a binding EC50 for PD-1 of about 2 ng/mL to about 200 ng/mL. In a further embodiment, the anti PD-1 antibodies and fragments thereof provided herein have a binding EC50 for PD-1 of about 5 ng/mL to about 100 ng/mL. In a further embodiment, the anti PD-1 antibodies and fragments thereof provided herein have a binding EC50 for PD-1 of about 5 ng/mL to about 50 ng/mL. In one embodiment, the anti PD-1 antibodies and fragments thereof provided herein have a binding EC50 for PD-1 of about 500 ng/mL or less, about 400 ng/mL or less, about 300 ng/mL or less, about 250 ng/mL or less, about 200 ng/mL or less, about 150 ng/mL or less, about 100 ng/mL or less, about 75 ng/mL or less, about 60 ng/mL or less, about 50 ng/mL or less, about 40 ng/mL or less, or about 30 ng/mL or less.

In one embodiment, the anti PD-1 antibodies and fragments thereof provided herein inhibit PD-L1 binding with an IC50 of about of about 1 ng/mL to about 1000 ng/mL. In a further embodiment, the anti PD-1 antibodies and fragments thereof provided herein inhibit PD-L1 binding with an IC50 of about 2 ng/mL to about 800 ng/mL. In a further embodiment, the anti PD-1 antibodies and fragments thereof provided herein inhibit PD-L1 binding with an IC50 of about 5 ng/mL to about 500 ng/mL. In a further embodiment, the anti PD-1 antibodies and fragments thereof provided herein inhibit PD-L1 binding with an IC50 of about 5 ng/mL to about 100 ng/mL. In a further embodiment, the anti PD-1 antibodies and fragments thereof provided herein inhibit PD-L1 binding with an IC50 of about 10 ng/mL to about 50 ng/mL. In one embodiment, the anti PD-1 antibodies and fragments thereof provided herein inhibit PD-L1 binding with an IC50 of about 800 ng/mL or less, about 400 ng/mL or less, about 300 ng/mL or less, about 250 ng/mL or less, about 200 ng/mL or less, about 150 ng/mL or less, about 100 ng/mL or less, about 75 ng/mL or less, about 60 ng/mL or less, about 50 ng/mL or less, about 40 ng/mL or less, or about 30 ng/mL or less.

In one embodiment, the anti-PD-1 antibody provided herein is a humanized antibody having a light chain variable region amino acid sequence according to SEQ ID NO: 133 and a heavy chain variable region amino acid according to SEQ ID NO: 131; or having a light chain variable region amino acid sequence according to SEQ ID NO: 143 and a heavy chain variable region amino acid sequence according to SEQ ID NO: 141; or having a light chain variable region amino acid sequence according to SEQ ID NO: 152 and a heavy chain variable region amino acid sequence according to SEQ ID NO: 131; wherein the anti-PD-1 antibody has a PD-1 binding EC50 of about 200 ng/ml or less or about 150 ng/mL or less or about 100 ng/mL or less or about 80 ng/ml or less or about 60 ng/mL or less, as measured by ELISA or FACS. In another embodiment, the anti-PD-1 antibody provided herein is a humanized antibody having a light chain variable region amino acid sequence according to SEQ ID NO: 133 and a heavy chain variable region amino acid according to SEQ ID NO: 131; or having a light chain variable region amino acid sequence according to SEQ ID NO: 143 and a heavy chain variable region amino acid sequence according to SEQ ID NO: 141; or having a light chain variable region amino acid sequence according to SEQ ID NO: 152 and a heavy chain variable region amino acid sequence according to SEQ ID NO: 131; wherein the anti-PD-1 antibody has a PD-L1 blockage IC50 of about 1000 ng/mL or less, or about 800 ng/mL or less, or about 600 ng/mL or less, or about 500 ng/mL or less, or about 400 ng/mL or less, or about 300 ng/mL or less, or about 200 ng/mL or less, or about 100 ng/mL or less, or about 60 ng/mL or less, or about 30 ng/mL or less, or about 25 ng/mL or less, or about 20 ng/mL or less, or about 10 ng/mL or less, as measured by ELISA or FACS. In another embodiment, the anti-PD-1 antibody provided herein is a humanized antibody having a light chain variable region amino acid sequence according to SEQ ID NO: 133 and a heavy chain variable region amino acid according to SEQ ID NO: 131; or having a light chain variable region amino acid sequence according to SEQ ID NO: 143 and a heavy chain variable region amino acid sequence according to SEQ ID NO: 141; or having a light chain variable region amino acid sequence according to SEQ ID NO: 152 and a heavy chain variable region amino acid sequence according to SEQ ID NO: 131; wherein the anti-PD-1 antibody has an affinity for PD-1 of about 1 nM or less, or about 0.5 nM or less, or about 0.1 nM or less, or about 0.05 nM or less. In a particular embodiment, the humanized anti-PD-1 antibody has an affinity for PD-1 of about 0.1 nM.

In one embodiment, the anti-PD-1 antibodies and fragments thereof provided bind to PD-1 on T cells, disrupting the PD-1/PD-L1 interaction and resulting in an increase in T cell activation. In a further embodiment, the antibodies and fragments thereof bind PD-1 and result in an increase in T cell proliferation and/or cytokine production. In a yet further embodiment, the antibodies and fragments thereof bind PD-1 and result in an increase of one or more cytokines selected from the group consisting of IL-2, IFNγ, TNF, IL-1, IL-4, IL-5, IL-6, IL-12, IL-13, IL-17, and GM-CSF. Thus, in one aspect, the present invention provides methods for modulating an immune response comprising contacting T cells with the anti-PD-1 antibody or fragment thereof. In one embodiment, the modulation of an immune response by the anti-PD-1 antibodies and fragments provided herein may be measured in a mixed lymphocyte (MLR) reaction. In one embodiment, the anti-PD-1 antibodies provided herein increase the level of cytokine production from lymphocytes in an MLR. In a further embodiment, the anti-PD-1 antibodies increase the level of IL-2 production and/or IFNγ production in an MLR. In a yet further embodiment, the anti-PD-1 antibodies increase the level of IL-2 production and IFNγ production in an MLR. In one embodiment, the anti-PD-1 antibodies enhance memory T cell responses. In a further embodiment, the anti-PD-1 antibodies enhance memory T cell responses as measured by an increase in IFNγ production from memory T cells.

In one embodiment, the anti-PD-1 antibodies and fragments thereof provided herein inhibit regulatory T cell function. In a further embodiment, the anti-PD-1 antibodies and fragments thereof inhibit the suppression of effector T cells by regulatory T cells. In another embodiment, the anti-PD-1 antibodies and fragments thereof restore the effector functions of T cells in the presence of regulatory T cells. In a further embodiment, the anti-PD-1 antibodies and fragments thereof restore the ability of effector T cells to proliferate and/or produce cytokines in the presence of regulatory T cells. Thus, in one embodiment, the present invention provides a method for inhibiting the suppressive effects of regulatory T cells in vitro or in a subject in need thereof.

In one aspect, an isolated antibody or fragment thereof that binds to PD-1 is provided, wherein the antibody is produced by a hybridoma selected from the group consisting of the hybridomas herein termed 10D1, 4C10, 7D3, 13F1, 15H5, 14A6, 22A5, 6E1, 5A8, 7A4, and 7A4D. Thus, the present invention also encompasses the hybridomas 10D1, 4C10, 7D3, 13F1, 15H5, 14A6, 22A5, 6E1, 5A8, 7A4, and 7A4D, as well as any hybridoma producing an antibody disclosed herein. The present invention also provides isolated polynucleotides encoding the antibodies and fragments thereof provided herein. Expression vectors comprising the isolated polynucleotides, and host cells comprising such expression vectors, are also encompassed in the invention.

In one embodiment, the present invention provides anti-PD-1 antibody immunoconjugates. Thus, the present invention provides an antibody or fragment thereof that binds to PD-1 and that is linked or conjugated to a therapeutic agent. Therapeutic agents that may be linked or conjugated to the anti-PD-1 antibody may include, but are not limited to, cytotoxic drugs, radioactive isotopes, immunomodulators, or antibodies.

In one aspect, the present invention provides compositions comprising one or more anti-PD-1 antibody or fragment thereof provided herein, and a pharmaceutically acceptable carrier.

In one aspect, the present invention provides methods for modulating an immune response in a subject, the method comprising administering to the subject a therapeutically effective amount of an anti-PD-1 antibody or fragment thereof provided herein. In one embodiment, the present invention provides methods for treating or preventing a disease or disorder in a subject in need thereof, comprising administering to the subject a therapeutically effective amount of an anti-PD-1 antibody or fragment thereof provided herein.

In one embodiment, the present invention provides a method for enhancing anti-tumor responses in a subject in need thereof, comprising administering to the subject a therapeutically effective amount of an anti-PD-1 antibody or fragment of the invention. In another embodiment, the present invention provides a method for reducing tumors or inhibiting the growth of tumor cells in a subject in need thereof, comprising administering to the subject a therapeutically effective amount of an anti-PD-1 antibody or fragment of the invention. In another embodiment, the present invention provides a method for treating cancer in a subject in need thereof, comprising administering to the subject a therapeutically effective amount of an anti-PD-1 antibody or fragment of the invention. In a further embodiment, the cancer is selected from the group consisting of lymphoma, leukemia, melanoma, glioma, breast cancer, lung cancer, colon cancer, bone cancer, ovarian cancer, bladder cancer, kidney cancer, liver cancer, stomach cancer, rectal cancer, testicular cancer, salivary cancer, thyroid cancer, thymic cancer, epithelial cancer, head or neck cancer, gastric cancer, pancreatic cancer, or a combination thereof.

In one embodiment, the present invention provides a method for treating an infectious disease in a subject in need thereof, comprising administering to the subject a therapeutically effective amount of an anti-PD-1 antibody or fragment of the invention. In a further embodiment, the infectious disease is selected from the group consisting of candidiasis, candidemia, aspergillosis, streptococcal pneumonia, streptococcal skin and oropharyngeal conditions, gram negative sepsis, tuberculosis, mononucleosis, influenza, respiratory illness caused by Respiratory Syncytial Virus, malaria, schistosomiasis, and trypanosomiasis.

BRIEF DESCRIPTION OF THE FIGURES

FIGS. 1A and 1B are a graphs showing the blockage of PD-1 ligand PD-L1 and PD-L2 binding to PD-1 by murine anti-PD-1 antibodies as measured by FACS. FIG. 1A shows the blockage of PD-L1's binding by murine anti-PD-1 antibodies and FIG. 1B shows the blockage of PD-L2's binding by murine anti-PD-1 antibodies. The top panels of FIG. 1A and FIG. 1B show the MFI over a range of antibody concentrations. The blockage IC50 for the anti-PD-1 antibodies are shown in the bottom panels of FIG. 1A and FIG. 1B.

FIG. 6 shows the binding EC50 of humanized 13F1 (FIG. 6A) and humanized 7A4 (FIG. 6B) anti-PD-1 antibodies as measured by ELISA. The top panel of FIG. 6A shows the absorbance over a range of concentrations of chimeric 13F1, humanized 13F1-hIgG1 (h13F1-IgG1), humanized 13F1-hIgG4 (h13F1-IgG4), or control hIgG4. The bottom panel of FIG. 6A shows the calculated EC50 of each of the test antibodies. The top panel of FIG. 6B shows the absorbance over a range of concentrations of chimeric 7A4-hIgG1, chimeric 7A4-hIgG4, humanized 784-hIgG1 (h7A4hIgG1), humanized 7A4-hIgG4 (h7A4hIgG4), or control hIgG4. The bottom panel of FIG. 6B shows the calculated EC50 of each of the test antibodies.

FIG. 7 shows the binding EC50 of humanized 13F1 (FIG. 7A) and humanized 7A4 (FIG. 7B) anti-PD-1 antibodies as measured by FACS. The top panel of FIG. 7A shows the mean fluorescence intensity (MFI) over a range of concentrations of control hIgG4, chimeric 13F1-hIgG4, humanized 13F1-hIgG1 (h13F1-hIgG1), or humanized 13F1-hIgG4 (h13F1-hIgG4). The bottom panel of FIG. 7A shows the calculated EC50 of each of the test antibodies. The top panel of FIG. 7B shows the MFI over a range of concentrations of control hIgG4, chimeric 7A4-hIgG4, chimeric 7A4-chimeric-IgG1, humanized 7A4-IgG4 (h7A4-hIgG4), or humanized 7A4-IgG1 (h7A4-hIgG1). The bottom panel of FIG. 7B shows the calculated EC50 of each of the test antibodies.

FIG. 8 shows the blockage of PD-L1 binding by humanized 13F1 (FIG. 8A) and humanized 7A4 (FIG. 8B) anti-PD-1 antibodies as measured by ELISA. FIG. 8A shows the absorbance over a range of concentrations of control hIgG4, chimeric 13F1, humanized 13F1-hIgG1, or humanized 13F1-hIgG4. FIG. 8B shows the absorbance over a range of concentrations of control hIgG4, chimeric 7A4-hIgG1, chimeric 7A4-hIgG4, humanized 784-hIgG1 or humanized 7A4-hIgG4. FIG. 8C shows the calculated PD-L1 blockage IC50 of the chimeric and humanized 13F1 and 7A4 antibodies.

FIG. 17B indicates the blockage IC50 of PD-L1's binding to 293T-PD1 cells by 7A4D-hIgG4 antibody.

DETAILED DESCRIPTION

Figure 2:
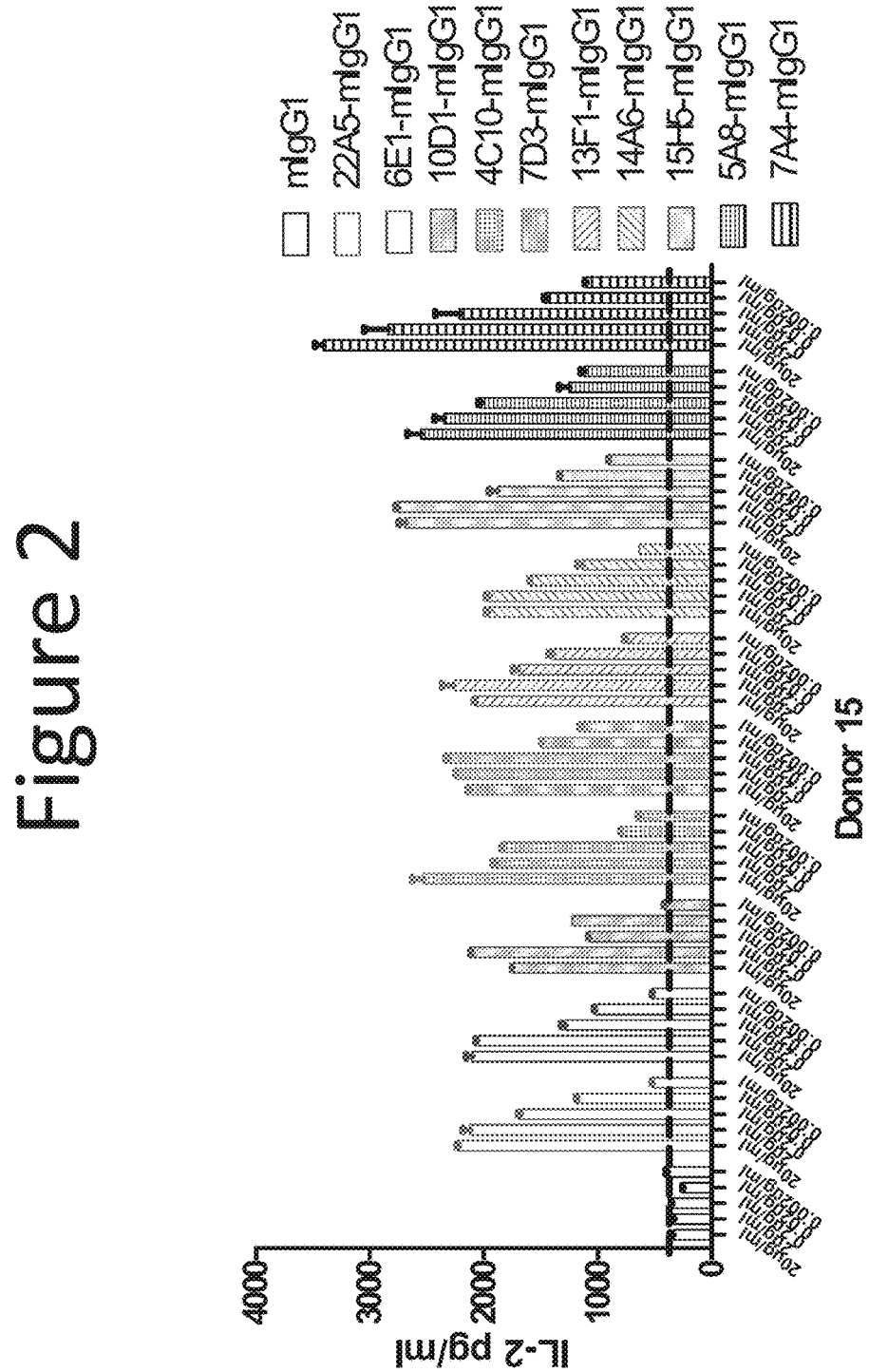
FIG. 2 is a graph showing IL-2 (pg/mL) production in an MLR in response to different concentrations of murine anti-PD-1 antibodies. The anti-PD-1 antibodies tested were, from left to right, control mIgG1, 22A5-mIgG1, 6E1-mIgG1, 10D1-mIgG1, 4C10-mIgG1, 7D3-mIgG1, 13F1-mIgG1, 14A6-mIgG1, 15H5-mIgG1, 5A8-mIgG1, and 7A4-mIgG1. As shown on the x-axis, each antibody was tested at 20 µg/mL, 2 µg/mL, 0.2 µg/mL, 0.02 µg/mL, and 0.002 µg/mL.

Programmed death receptor 1 (PD-1) is a checkpoint receptor of immune system. It is primarily expressed on activated T and B cells, but also occurs on monocytes and CD4-CD8-double negative T cells and NK-T cells under thymic development (Agata et al., supra; Okazaki et al. (2002) Curr. Opin. Immunol. 14: 391779-82; Bennett et al. (2003) J Immunol 170:711-8). PD-1 has two ligands, PD-L1 and PD-L2. The interaction of PD-1 with either of the two ligands has been shown to attenuate T-cell responses in vitro and in vivo, which can, however, be reversed by inhibiting the local interaction of PD-1 with PD-L1, and the effect is additive when the interaction of PD-1 with PD-L2 is blocked as well (Iwai et al. (2002) Proc. Nat'l. Acad Sci. USA 99: 12293-7; Brown et al. (2003) J. Immunol. 170:1257-66).

PD-1 has been found to have a correlation with cancer growth and development due to its role in protecting tumor cells from efficient immune destruction. Its ligand, PD-L1, has been revealed to have significant expression on a number of mouse and human tumors, which is postulated to mediate immune evasion (Iwai, Y. et al., Proc. Natl. Acad. Sci. USA. 99: 12293-12297 (2002); Strome S. E. et al., Cancer Res., 63:6501-6505 (2003); Dong et al. (2002) Nat. Med. 8:787-9). In humans, expression of PD-1 (on tumor infiltrating lymphocytes) and/or PD-L1 (on tumor cells) has been found in a number of primary tumor biopsies as assessed by immunohistochemistry. Such tissues include cancers of the lung, liver, ovary, cervix, skin, colon, glioma, bladder, breast, kidney, esophagus, stomach, oral squamous cell, urothelial cell, and pancreas as well as tumors of the head and neck (Brown J. A. et al., J. Immunol. 170: 1257-1266 (2003); Dong H. et al., Nat. Med. 8: 793-800 (2002); Wintterle et al., Cancer Res. 63:7462-7467 (2003); Strome S. E. et al., Cancer Res., 63: 6501-6505 (2003); Thompson R. H. et al., Cancer Res. 66: 3381-5(2006); Thompson et al., Clin. Cancer Res. 13: 1757-61(2007); Nomi T. et al., Clin. Cancer Res. 13: 2151-7. (2007)). More strikingly, PD-1 ligand expression on tumor cells has been correlated to poor prognosis of cancer patients across multiple tumor types (reviewed in OkaZaki and Honjo, Int. Immunol. 19: 813-824 (2007)).

While the interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54: 3 07-3 14; Konishi et al. (2004) Clin. Cancer Res. 10:5094-100), blockade of the PD-1/PD-L1 interaction was accordingly shown to enhance tumor-specific T-cell immunity and be helpful in clearance of tumor cells by the immune system. In a murine model of aggressive pancreatic cancer, for example, Nomi T., et al. (Clin. Cancer Res. 13: 2151-2157, 2007) demonstrated the therapeutic efficacy of PD-1/PD-L1 blockade. Administration of either PD-1 or PD-L1 directed antibody significantly inhibited tumor growth. Antibody blockade effectively promoted tumor reactive CD8+ T cell infiltration into the tumor resulting in the up-regulation of anti-tumor effectors including IFN-γ, granzyme B and perforin. Additionally, the authors showed that PD-1 blockade can be effectively combined with chemotherapy to yield a synergistic effect. In another study, using a model of squamous cell carcinoma in mice, antibody blockade of PD-1 or PD-L1 significantly inhibited tumor growth (Tsushima F. et al., Oral Oncol. 42:268-274 (2006)).

Furthermore, transfection of a murine mastocytoma line with PD-L1 led to decreased lysis of the tumor cells when co-cultured with a tumor-specific CTL clone. Lysis was restored when anti-PD-L1 mAb was added (Iwai Y. et al., Proc. Natl. Acad. Sci. USA. 99: 12293-12297 (2002)). In vivo, blocking the PD1/PD-L1 interaction was shown to increase the efficacy of adoptive T cell transfer therapy in a mouse tumor model (Strome S. E. et al., Cancer Res. 63:6501-6505 (2003)). Further evidence for the role of PD-1 in cancer treatment comes from experiments performed with PD-1 knockout mice. PD-L1 expressing myeloma cells grew only in Wild-type animals (resulting in tumor growth and associated animal death), but not in PD-1 deficient mice (Iwai Y., et al., Proc. Natl. Acad. Sci. USA. 99: 12293-12297 (2002)), In human studies, R. M. Wong et al. (Int. Immunol. 19:1223-1234 (2007)) showed that PD-1 blockade using a fully human anti-PD-1 antibody augmented the absolute numbers of tumor-specific CD8+ T cells (CTLs) in ex vivo stimulation assays using vaccine antigens and cells from vaccinated individuals. In a similar study, antibody blockade of PD-L1 resulted in enhanced cytolytic activity of tumor-associated antigen-specific cytotoxic T cells and increased cytokine production by tumor specific TH cells (Blank C. et al., Int. J. Cancer 119: 317-327 (2006)). The same authors showed that PD-L1 blockade augments tumor-specific T cell responses in vitro when used in combination with anti-CTLA-4 blockade. Overall, the PD-1/PD-L1 pathway is a target for the development of antibody therapeutics for cancer treatment. Anti-PD-1 antibodies may also be useful in chronic viral infection. Memory CD8+ T cells generated after an acute viral infection are highly functional and constitute an important component of protective immunity. In contrast, chronic infections are often characterized by varying degrees of functional impairment (exhaustion) of virus-specific T-cell responses, and this defect is a principal reason for the inability of the host to eliminate the persisting pathogen. Although functional effector T cells are initially generated during the early stages of infection, they gradually lose function during the course of a chronic infection. Barber et al. (Barber et al., Nature 439: 682-687 (2006)) showed that mice infected with a laboratory strain of LCMV developed chronic infection resulting in high levels of virus in the blood and other tissues. These mice initially developed a robust T cell response, but eventually succumbed to the infection upon T cell exhaustion. The authors found that the decline in number and function of the effector T cells in chronically infected mice could be reversed by injecting an antibody that blocked the interaction between PD-1 and PD-L1.

In one aspect, the present invention provides antibodies or antigen binding fragments thereof that bind to programmed cell death 1 (PD-1). PD-1. In one embodiment, the antibodies or fragments thereof bind to human PD-1. In another embodiment, the antibodies or fragments thereof bind to human and to cynomolgous PD-1. In another embodiment, the antibodies or fragments thereof block the interaction of PD-1 on T cells with its ligand PD-L1. In one aspect, the present invention provides methods of making and using the anti-PD-1 antibodies or fragments thereof, and compositions comprising anti-PD-1 antibodies or fragments thereof, including pharmaceutical compositions.

As used herein, the term "antibody" refers to a binding protein having at least one antigen binding domain. The antibodies and fragments thereof of the present invention may be whole antibodies or any fragment thereof. Thus, the antibodies and fragments of the invention include monoclonal antibodies or fragments thereof and antibody variants or fragments thereof, as well as immunoconjugates. Examples of antibody fragments include Fab fragments, Fab' fragments, F(ab)' fragments, Fv fragments, isolated CDR regions, single chain Fv molecules (scFv), and other antibody fragments known in the art. Antibodies and fragments thereof may also include recombinant polypeptides, fusion proteins, and bi-specific antibodies. The anti-PD-1 antibodies and fragments thereof disclosed herein may be of an IgG1, IgG2, IgG3, or IgG4 isotype. The term "isotype" refers to the antibody class encoded by the heavy chain constant region genes. In one embodiment, the anti-PD-1 antibodies and fragments thereof disclosed herein are of an IgG1 or an IgG4 isotype. The PD-1 antibodies and fragments thereof of the present invention may be derived from any species including, but not limited to, mouse, rat, rabbit, primate, llama, and human. The PD-1 antibodies and fragments thereof may be chimeric, humanized, or fully human antibodies. In one embodiment, the anti-PD-1 antibodies are murine antibodies. In another embodiment, the anti-PD1 antibodies are chimeric antibodies. In a further embodiment, the chimeric antibodies are mouse-human chimeric antibodies. In another embodiment, the antibodies are derived from mice and are humanized.

A "chimeric antibody" is an antibody having at least a portion of the heavy chain variable region and at least a portion of the light chain variable region derived from one species; and at least a portion of a constant region derived from another species. For example, in one embodiment, a chimeric antibody may comprise murine variable regions and a human constant region.

A "humanized antibody" is an antibody containing complementarity determining regions (CDRs) that are derived from a non-human antibody; and framework regions as well as constant regions that are derived from a human antibody. For example, the anti-PD-1 antibodies provided herein may comprise CDRs derived from one or more murine antibodies and human framework and constant regions. Thus, in one embodiment, the humanized antibody provided herein binds to the same epitope on PD-1 as the murine antibody from which the antibody's CDRs are derived. Exemplary humanized antibodies are provided herein. Additional anti-PD-1 antibodies comprising the heavy and light chain CDRs provided herein, or variants thereof, may be generated using any human framework sequence, and are also encompassed in the present invention. In one embodiment, framework sequences suitable for use in the present invention include those framework sequences that are structurally similar to the framework sequences provided herein. Further modifications in the framework regions may be made to improve the properties of the antibodies provided herein. Such further framework modifications may include chemical modifications; point mutations to reduce immunogenicity or remove T cell epitopes; or back mutation to the residue in the original germline sequence.

In some embodiments, such framework modifications include those corresponding to the mutations exemplified herein, including backmutations to the germline sequence. For example, in one embodiment, one or more amino acids in the human framework regions of the VH and/or VL of the humanized antibodies provided herein are back mutated to the corresponding amino acid in the parent murine antibody. As an example, as for VH and VL of 7A4 and 13F1, several sites of framework amino acid of the aforementioned template human antibody were back mutated to the corresponding amino acid sequences in mouse 7A4 and 13F1 antibody. In one embodiment, the amino acid at positions 40 and/or 45 and/or 70 and/or 72 of the light chain variable region is back mutated to the corresponding amino acid found at that position in the mouse 7A4 or 13F1 light chain variable region. In another embodiment, the amino acid at positions 2 and/or 26 and/or 46 and/or 48 and/or 49 and/or 67 and/or 70 and/or 71 of the heavy chain variable region is back mutated to the corresponding amino acid found at that position in the mouse 7A4 or 13F1 heavy chain variable region. In one embodiment, the humanized 7A4 antibody comprises a light chain variable region wherein the amino acid at position 40 is mutated from Tyr (Y) to Phe (F) and the amino acid at position 72 is mutated from Gly (G) to Arg (R); and a heavy chain variable region wherein the amino acid at position 2 is mutated from Val (V) to Ile (I), the amino acid at position 46 is mutated from Glu (E) to Lys (K), and the amino acid at position 70 is mutated from Phe (F) to Ile (I). In one embodiment, the humanized 13F1 antibody comprises a light chain variable region wherein the amino acid at position 45 is mutated from Leu (L) to Pro (P) and the amino acid at position 70 is mutated from Phe (F) to Tyr (Y); and a heavy chain variable region wherein the amino acid at position 26 is mutated from Gly (G) to Tyr (Y), the amino acid at position 48 is mutated from Ile (I) to Met (M), the amino acid at position 49 is mutated from Gly (G) to Ala (A), the amino acid at position 67 is mutated from Val (V) to Ile (I), and the amino acid at position 71 is mutated from Val (V) to Arg (R). Additional or alternate back mutations may be made in the framework regions of the humanized antibodies provided herein in order to improve the properties of the antibodies.

The present invention also encompasses humanized antibodies that bind to PD-1 and comprise framework modifications corresponding to the exemplary modifications described herein with respect to any suitable framework sequence, as well as other framework modifications that otherwise improve the properties of the antibodies. For example, in some embodiments, the antibodies provided herein comprise one or more mutations to remove one or more deamidation sites or one or more oxidation sites. For example, in one embodiment, the antibodies provided herein comprise a mutation of one or more asparagine residues to remove one or more deamidation sites; and/or mutation of one or more methionine residues to remove one or more oxidation sites.

In other embodiments, the antibodies provided herein comprise one or more mutations to improve stability, improve solubility, alter glycosylation, and/or reduce immunogenicity, such as, for example, by targeted amino acid changes that reduce deamidation or oxidation, reduce isomerization, optimize the hydrophobic core and/or charge cluster residues, remove hydrophobic surface residues, optimize residues involved in the interface between the variable heavy and variable light chains, and/or modify the isoelectric point.

As used herein, the term "derived" when used to refer to a molecule or polypeptide relative to a reference antibody or other binding protein, means a molecule or polypeptide that is capable of binding with specificity to the same epitope as the reference antibody or other binding protein.

The antibodies and antigen-binding fragments thereof disclosed herein are specific for PD-1. In one embodiment, the antibodies and fragments thereof are specific for human PD-1. In one embodiment, the antibodies and fragments provided herein bind to human or primate PD-1 but not to PD-1 from any other mammal. In a further embodiment, the antibodies and fragments thereof do not bind to mouse PD-1. The terms "human PD-1," "hPD-1", and "huPD-1" and the like are used interchangeably herein and refer to human PD-1 and variants or isoforms of human PD-1. By "specific for" is meant that the antibodies and fragments thereof bind PD-1 receptor with greater affinity than any other target. In one embodiment, the PD-1 antibodies and fragments provided herein are specific for PD-1 and do not cross react with CTLA4, ICOS, or CD28. As used herein, the term "EC50" refers to the effective concentration, 50% maximal response of the antibody. As used herein, the term "IC50" refers to the inhibitory concentration, 50% maximal response of the antibody. Both EC50 and IC50 may be measured by ELISA or FACS analysis, or any other method known in the art.

In one embodiment, the anti-PD1 antibodies and fragments or variants thereof have an affinity (KD) for PD-1 in the range of about 0.001 nM to about 100 nM, about 0.002 nM to about 50 nM, about 0.005 nM to about 5 nM, about 0.01 nM to about 1 nM, or about 0.05 nM to about 0.1 nM. In one embodiment, the antibodies and fragments thereof have an affinity (KD) for PD-1 of about 50 nM or less, about 25 nM or less, about 20 nM or less, about 15 nM or less, about 10 nM or less, about 8 nM or less, about 6 nM or less, about 4 nM or less, about 2 nM or less, about 1 nM or less, about 0.9 nM or less, about 0.8 nM or less, about 0.7 nM or less, about 0.6 nM or less, about 0.5 nM or less, about 0.4 nM or less, about 0.3 nM or less, about 0.2 nM or less, about 0.1 nM or less, about 0.09 nM or less, about 0.08 nM or less, about 0.07 nM or less, about 0.06 nM or less, about 0.05 nM or less, about 0.04 nM or less, about 0.03 nM or less, about 0.02 nM or less, about 0.01 nM or less, about 0.009 nM or less, about 0.008 nM or less, about 0.007 nM or less, about 0.006 nM or less, about 0.005 nM or less, about 0.004 nM or less, about 0.003 nM or less, about 0.002 nM or less, or about 0.001 nM or less. In one embodiment, the antibodies and fragments thereof have an affinity (KD) for PD-1 of about 10 nM, about 9 nM, about 8 nM, about 7 nM, about 6 nM, about 5 nM, about 4 nM, about 3 nM, about 2 nM, about 1 nM, about 0.9 nM, about 0.8 nM, about 0.7 nM, about 0.6 nM, about 0.5 nM, about 0.4 nM, about 0.3 nM, about 0.2 nM, about 0.1 nM, about 0.09 nM, about 0.08 nM, about 0.07 nM, about 0.06 nM, about 0.05 nM, about 0.04 nM, about 0.03 nM, about 0.02 nM, about 0.01 nM, about 0.009 nM, about 0.008 nM, about 0.007 nM, about 0.006 nM, about 0.005 nM, about 0.004 nM, about 0.003 nM, about 0.002 nM, or about 0.001.

In one embodiment, the antibodies and fragments provided herein comprise a light chain and a heavy chain, each of which comprises three CDR regions. Exemplary light chain CDR sequences (LCDR1, LCDR2, and LCDR3) for PD-1 antibodies of the invention are provided below in Table 1. Exemplary heavy chain CDR sequences (HCDR1, HCDR2, and HCDR3) for PD-1 antibodies of the invention are provided below in Table 2. Exemplary variable regions and full antibody sequences for PD-1 antibodies of the invention are provided below in Table 3.

TABLE 1

Light Chain CDR sequences

| Name | LCDR | SEQ ID NO | Sequence |
|------|------|-----------|----------|
| 10D1 | 1 | 24 | RASQSISNNLH |
|      | 2 | 25 | YASQSIS |
|      | 3 | 26 | QQSNSWPLT |
| 4C10 | 1 | 34 | KASQSVSDDVA |
|      | 2 | 35 | YAFNRYT |
|      | 3 | 36 | QQDYRSPWT |
| 7D3  | 1 | 45 | RASQSISNDLH |
|      | 2 | 46 | YVSQSIS |
|      | 3 | 47 | QQSDSWPLT |
| 13F1 | 1 | 55 | RANSSVSSMH |
|      | 2 | 56 | AISNLAF |
|      | 3 | 57 | QQWSSRPPT |
| 15H5 | 1 | 65 | HASQSINVWLS |
|      | 2 | 66 | ASNLHT |
|      | 3 | 67 | QQGQSYPWT |

TABLE 1-continued

Light Chain CDR sequences

| Name | LCDR | SEQ ID NO | Sequence |
|---|---|---|---|
| 14A6 | 1 | 75 | RANSSVSSMH |
|  | 2 | 76 | AISNLAF |
|  | 3 | 77 | QQWNSRPPT |
| 22A5 | 1 | 85 | KASQDVDNAVA |
|  | 2 | 86 | WASTRHH |
|  | 3 | 87 | QQYSTFPYT |
| 6E1 | 1 | 95 | RASQSLSNNLH |
|  | 2 | 96 | YASQSIS |
|  | 3 | 97 | QQSNSWPLT |
| 5A8 | 1 | 105 | KASQSVSNDVA |
|  | 2 | 106 | YAFTRYI |
|  | 3 | 107 | QQDYSSPYT |
| 7A4 | 1 | 115 | RASESVDNYGYSFMN |
|  | 2 | 116 | RASNLES |
|  | 3 | 117 | QQSNADPT |

TABLE 2

Heavy chain CDR sequences

| Name | HCDR | SEQ ID NO | Sequence |
|---|---|---|---|
| 10D1 | 1 | 19 | SYGMS |
|  | 2 | 20 | TMSGGGRDIYYPDSMKG |
|  | 3 | 21 | QYYDDWFAY |
| 4C10 | 1 | 29 | TYGVH |
|  | 2 | 30 | VIWSGGSTDYNAAFIS |
|  | 3 | 31 | EKSVYGNYVGAMDY |

TABLE 2-continued

Heavy chain CDR sequences

| Name | HCDR | SEQ ID NO | Sequence |
|---|---|---|---|
| 7D3 | 1 | 40 | SYGMS |
|  | 2 | 41 | TISGGGRDIYYPDSVKG |
|  | 3 | 42 | QYYDDWFAY |
| 13F1 | 1 | 50 | SDYAWN |
|  | 2 | 51 | YISYSGYTSYNPSLKS |
|  | 3 | 52 | SLDYDYGTMDY |
| 15H5 | 1 | 60 | SYDMS |
|  | 2 | 61 | TISGGGSYTYYQDSVKG |
|  | 3 | 62 | PYGPYFDY |
| 14A6 | 1 | 70 | SDYAWN |
|  | 2 | 71 | YISYSGYTSYNPSLKS |
|  | 3 | 72 | SLDYDYGTMDY |
| 22A5 | 1 | 80 | YYDMS |
|  | 2 | 81 | TISGGGRNTYFIDSVKG |
|  | 3 | 82 | PYEGAVDF |
| 6E1 | 1 | 90 | SYGMS |
|  | 2 | 91 | TISGGGRDTYYLDSVKG |
|  | 3 | 92 | QYYDDWFAY |
| 5A8 | 1 | 100 | NNVVIG |
|  | 2 | 101 | DFYPGGYTNYNEKFKG |
|  | 3 | 102 | GYGTNYVVYFDV |
| 7A4 | 1 | 110 | NFGMN |
|  | 2 | 111 | WISGYTREPTYAADFKG |
|  | 3 | 112 | DVFDY |

TABLE 3

Light chain and heavy chain variable region sequences and full antibody sequences

| Name | Region[1] | SEQ ID NO | Sequence |
|---|---|---|---|
| 10D1 murine | Light chain variable | 23 | DIVLTQTPATLSVTPGDSVSLSCRASQSISNNLH WYQQKSHESPRLLIKYASQSISGIPSRFSGSGSGT DFTLNINSVETEDFGMYFCQQSNSWPLTFGAGT KLELKR |
| 10D1 murine | Heavy chain variable | 18 | EVKLVESGGGLVKPGGSLKLSCAASGFTFSSYG MSWLRQTPEKRLEWVATMSGGGRDIYYPDSMK GRFTISRDNAKNNLYLQMSSLRSEDTALYYCAR QYYDDWFAYWGQGTLVTVSA |
| 4C10 murine | Light chain variable | 33 | SIVMTQTPKFLLVSAGDRVTITCKASQSVSDDVA WYQQKPGQSPKLLIYYAFNRYTGVPDRFTGSGY GTDFTFTISTVQSEDLAVYFCQQDYRSPWTFGGG TKLEIKR |
| 4C10 murine | Heavy chain variable | 28 | QVQLKQSGPGLVQPSQNLSVTCTVSGFSLTTYG VHWVRQSPGKGLEWLGVIWSGGSTDYNAAFISR LTISKDNARSQVFFKMNSLQVNDTAMYYCAREK SVYGNYVGAMDYWGQGTSVTVSS |
| 7D3 murine | Light chain variable | 44 | DIVLTQSPATLSVTPGDSVSLSCRASQSISNDLH WYQQKSHESPRLLIKYVSQSISGIPSRFSGSGSGT DFTLSINSVETEDFGMYFCQQSDSWPLTFGAGTK LELKR |
| 7D3 murine | Heavy chain variable | 39 | EVKLVESGGGLVKPGGSLKLSCGASGFTFSSYG MSWVRQTPEKRLEWVATISGGGRDIYYPDSVKG RLTISRDNAKNNLYLQMSSLRSEDTALYYCVRQ YYDDWFAYWGQGTLVTVSA |

TABLE 3-continued

Light chain and heavy chain variable region sequences and full antibody sequences

| Name | Region[1] | SEQ ID NO | Sequence |
|---|---|---|---|
| 13F1 murine | Light chain variable | 54 | QIVLSQSPAILSASPGEKVTMTCRANSSVSSMHW YQQKPGSSPEPWIYAISNLAFGVPTRFSGSGSGT SYSLTISRVEAEDAATYFCQQWSSRPPTFGGGTK LEIKR |
| 13F1 murine | Heavy chain variable | 49 | DVQLQESGPGLVKPSQSLSLTCTVTGYSITSDYA WNWIRQFPGNQLEWMAYISYSGYTSYNPSLKSR ISITRDTSKNQFFLQLNSVTTEDTATYYCARSLD YDYGTMDYWGQGTSVTVSS |
| 15H5 murine | Light chain variable | 64 | DIQMNQSPSSLSASLGDTITITCHASQSINVWLS WYQQKPGNIPKLLIYRASNLHTGVPSRFSGSGSG TGFTLTISSLQPDDIATYYCQQGQSYPWTFGGGT KLEIKR |
| 15H5 murine | Heavy chain variable | 59 | EVKLVESGGGLVKPGGSLKLSCAASGFAFRSYD MSWVRQTPEKILEWVATISGGGSYTYYQDSVKG RFTISRDNARNTLYLQMSSLRSEDTALYYCASPY GPYFDYWGQGTTLTVSS |
| 14A6 murine | Light chain variable | 74 | QIVLSQSPAILSASPGEKVTMTCRANSSVSSMHW YQQKPGSSPEPWIYAISNLAFGVPARFSGSGSGT SYSLTISRVEAEDAATYFCQQWNSRPPTFGGGTK LEIKR |
| 14A6 murine | Heavy chain variable | 69 | DVQLQESGPGLVKPSQSLSLTCTVTGYSITSDYA WNWIRQFPGNQLEWMAYISYSGYTSYNPSLKSR ISITRDTSRNQFFLQLNSVTTEDTATYYCARSLD YDYGTMDYWGQGTSVTVSS |
| 22A5 murine | Light chain variable | 84 | DIVMTQSHKVMSTSVGDRVSITCKASQDVDNAV AWYQQNPGQSPKLLIKWASTRHHGVPDRFTGSG SGTDFTLTISTVQSEDLADFFCQQYSTFPYTFGG GTKLEIKR |
| 22A5 murine | Heavy chain variable | 79 | EVKLVESGGGLVKPGGSLKLSCSASGFSFSYYD MSWVRQTPEKGLEWVATISGGGRNTYFIDSVKG RFTISRDNVKNNLYLLMSSLRSEDTALYYCASPY EGAVDFWGQGTSVTVSS |
| 6E1 murine | Light chain variable | 94 | DIVLTQTPATLSVTPGDSVSLSCRASQSLSNNLH WYQQKSHESPRLLIKYASQSISGIPSRFSGSGSGT DFTLSINSVETEDFGMYFCQQSNSWPLTFGAGTK LEMKR |
| 6E1 murine | Heavy chain variable | 89 | EVKLVESGGGLVKPGGSLKLSCAASGFTFSSYG MSWVRQTPEKRLEWVATISGGGRDTYYLDSVKG RFTISRDNAKNNLYLQMSSLRSEDTALYYCVRQ YYDDWFAYWGQGTLVSNSA |
| 5A8 murine | Light chain variable | 104 | NIVMTQTPKILFISAGDRVTITCKASQSVSNDVA WYQQKPGQSPKLLIYYAFTRYIGVPDRFTGSGY GTDFTFTISTVQAEDLAVYFCQQDYSSPYTFGGG TKLEIKR |
| 5A8 murine | Heavy chain variable | 99 | QVQLQQSGDELVRPGTSVKMSCKAAGYTFTNN WIGWVKQRPGHGLEWIGDFYPGGGYTNYNEKF KGKATLTADTSSSTAYMQLSSLTSEDSAIYYCAR GYGTNYWYFDVWGAGTTVTVSS |
| 7A4 murine | Light chain variable | 114 | DIVLTQSPASLAVSLGQRATISCRASESVDNYGY SFMNWFQQKPGQPPKLLIYRASNLESGIPARFSG SGSRTNFTLTINPVEADDVATYFCQQSNADPTFG GGTNLEIKRA |
| 7A4 murine | Heavy chain variable | 109 | QIHLVQSGPELKKPGETVKISCKASGYTFTNFGM NWVKQAPGKGLKWMGWISGYTREPTYAADFKG RFAISLETSASTAYLQINDLKNEDMATYFCARDV FDYWGQGTTLTVSS |

TABLE 3-continued

Light chain and heavy chain variable region sequences and full antibody sequences

| Name | Region[1] | SEQ ID NO | Sequence |
|---|---|---|---|
| 7A4 chimeric | Full length heavy chain IgG1 | 119 | QIHLVQSGPELKKPGETVKISCKASGYTFTNFGMNWVKQAPGKGLKWMGW ISGYTREPTYAADFKGRFAISLETSASTAYLQINDLKNEDMATYFCARDV FDYWGQGTTLTVSSASTKGPSVFPLAPSSKSTSGGTAALGCLVKDYFPEP VTVSWNSGALTSGVHTFPAVLQSSGLYSLSSVVTVPSSSLGTQTYICNVN HKPSNTKVDKKVEPKSCDKTHTCPPCPAPELLGGPSVFLFPPKPKDTLMI SRTPEVTCVVVAVSHEDPEVKFNWYVDGVEVHNAKTKPREEQYASTYRVV SVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| 7A4 chimeric | Full length heavy chain IgG4 | 121 | QIHLVQSGPELKKPGETVKISCKASGYTFTNFGMNWVKQAPGKGLKWMGW ISGYTREPTYAADFKGRFAISLETSASTAYLQINDLKNEDMATYFCARDV FDYWGQGTTLTVSSASTKGPSVFPLAPCSRSTSESTAALGCLVKDYFPEP VTVSWNSGALTSGVHTFPAVLQSSGLYSLSSVVTVPSSSLGTKTYTCNVD HKPSNTKVDKRVESKYGPPCPPCPAPEAAGGPSVFLFPPKPKDTLMISRT PEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQE EMTKNQVSLTCLVKGFYPSDIAVEWESNGQPENNYKTTPPVLDSDGSEEL YSRLTVDKSRWQEGNVFSCSVMHEALHNHYTQKSLSLSLG |
| 7A4 chimeric | Full length light chain | 123 | DIVLTQSPASLAVSLGQRATISCRASESVDNYGYSFMNWFQQKPGQPPKL LIYRASNLESGIPARFSGSGSRTNFTLTINPVEADDVATYFCQQSNADPT FGGGTNLEIKRTVAAPSVFIFPPSDEQLKSGTASVVCLLNNFYPREAKVQ WKVDNALQSGNSQESVTEQDSKDSTYSLSSTLTLSKADYEKHKVYACEVT HQGLSSPVTKSFNRGEC |
| 13F1 chimeric | Full length heavy chain IgG1 | 125 | DVQLQESGPGLVKPSQSLSLTCTVTGYSITSDYAWNWIRQFPGNQLEWMA YISYSGYTSYNPSLKSRISITRDTSKNQFFLQLNSVTTEDTATYYCARSL DYDYGTMDYWGQGTSVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVAVSHEDPEVKFNWYVDGVEVHNAKTKPREEQYA STYRVVSVLTVLHQDWLNGKEYKCKVSNKALPAPIEKTISKAKGQPREPQ VYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 13F1 chimeric | Full length heavy chain IgG4 | 127 | DVQLQESGPGLVKPSQSLSLTCTVTGYSITSDYAWNWIRQFPGNQLEWMA YISYSGYTSYNPSLKSRISITRDTSKNQFFLQLNSVTTEDTATYYCARSL DYDYGTMDYWGQGTSVTVSSASTKGPSVFPLAPCSRSTSESTAALGCLVK DYFPEPVTVSWNSGALTSGVHTFPAVLQSSGLYSLSSVVTVPSSSLGTKT YTCNVDHKPSNTKVDKRVESKYGPPCPPCPAPEAAGGPSVFLFPPKPKDT LMISRTPEVTCVVVDVSQEDPEVQFNWYVDGVEVHNAKTKPREEQFNSTY RVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDS DGSFFLYSRLTVDKSRWQEG NVFSCSVMHEALHNHYTQKSLSLSLG |
| 13F1 chimeric | Full length light chain | 129 | QIVLSQSPAILSASPGEKVTMTCRANSSVSSMHWYQQKPGSSPEPWIYAI SNLAFGVPTRFSGSGSGTSYSLTISRVEAEDAATYFCQQWSSRPPTFGGG TKLEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGL SSPVTKSFNRGEC |
| 7A4 humanized | Heavy chain variable | 131 | QIQLVQSGSELKKPGASVKVSCKASGYTFTNFGMNWVRQAPGQGLKWMGW ISGYTREPTYAADFKGRFVISLDTSVSTAYLQISSLKAEDTAVYYCARDV FDYWGQGTLVTVSS |
| 7A4 humanized | Light chain variable | 133 | DIVLTQSPASLAVSPGQRATITCRASESVDNYGYSFMNWFQQKPGQPPKL LIYRASNLESGVPARFSGSGSRTDFTLTINPVEANDTANYYCQQSNADPT FGQGTKLEIK |
| 13F1 humanized | Heavy chain variable | 141 | QVQLQESGPGLVKPSQTLSLTCTVSGYSISSDYAWNWIRQPPGKGLEWMA YISYSGYTSYNPSLKSRITISRDTSKNQFSLKLSSVTAADTAVYYCARSL DYDYGTMDYWGQGTLVTVSS |
| 13F1 humanized | Light chain variable | 143 | EIVLTQSPATLSLSPGERATLSCRANSSVSSMHWYQQKPGQSPEPWIYAI SNLAFGVPARFSGSGSGTDYTLTISSLEPEDFAVYYCQQWSSRPPTFGQG TKLEIK |

TABLE 3-continued

Light chain and heavy chain variable region sequences and full antibody sequences

| Name | Region[1] | SEQ ID NO | Sequence |
|---|---|---|---|
| 7A4 humanized-IgG1 (D265A) | Full heavy chain | 135 | QIQLVQSGSELKKPGASVKVSCKASGYTFTNFGMNWVRQAPGQGLKWMGW ISGYTREPTYAADFKGRFVISLDTSVSTAYLQISSLKAEDTAVYYCARDV FDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVN HKPSNTKVDKKVEPKSCDKTHTCPPCPAPELLGGPSVFLFPPKPKDTLMI SRTPEVTCVVVAVSHEDPEVKFNWYVDGVEVHNAKTKPREEQYNSTYRVV SVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| 7A4 humanized-IgG4 (F234A/ L235A) | Full heavy chain | 137 | QIQLVQSGSELKKPGASVKVSCKASGYTFTNFGMNWVRQAPGQGLKWMGW ISGYTREPTYAADFKGRFVISLDTSVSTAYLQISSLKAEDTAVYYCARDV FDYWGQGTLVTVSSASTKGPSVFPLAPCSRSTSESTAALGCLVKDYFPEP VTVSWNSGALTSGVHTFPAVLQSSGLYSLSSVVTVPSSSLGTKTYTCNVD HKPSNTKVDKRVESKYGPPCPPCPAPEAAGGPSVFLFPPKPKDTLMISRT PEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQE EMTKNQVSLTCLVKGFYPSDIAVEWESNGQPENNYKTTPPVLDSDGSFFL YSRLTVDKSRWQEGNVFSCSVMHEALHNHYTQKSLSLSLG |
| 7A4 humanized | Full light chain | 139 | DIVLTQSPASLAVSPGQRATITCRASESVDNYGYSFMNWFQQKPGQPPKL LIYRASNLESGVPARFSGSGSRTDFTLTINPVEANDTANYYCQQSNADPT FGQGTKLEIKRTVAAPSVFIFPPSDEQLKSGTASVVCLLNNFYPREAKVQ WKVDNALQSGNSQESVTEQDSKDSTYSLSSTLTLSKADYEKHKVYACEVT HQGLSSPVTKSFNRGEC |
| 13F1 humanized-IgG1 (D265A) | Full heavy chain | 145 | QVQLQESGPGLVKPSQTLSLTCTVSGYSISSDYAWNWIRQPPGKGLEWMA YISYSGYTSYNPSLKSRITISRDTSKNQFSLKLSSVTAADTAVYYCARSL DYDYGTMDYWGQGTLVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVAVSHEDPEVKFNWYVDGVEVHNAKTKPREEQYN STYRVVSVLTVLHQDWLNGKEYKCKVSNKALPAPIEKTISKAKGQPREPQ VYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 13F1 humanized-IgG4 (F234A/ L235A) | Full heavy chain | 147 | QVQLQESGPGLVKPSQTLSLTCTVSGYSISSDYAWNWIRQPPGKGLEWMA YISYSGYTSYNPSLKSRITISRDTSKNQFSLKLSSVTAADTAVYYCARSL DYDYGTMDYWGQGTLVTVSSASTKGPSVFPLAPCSRSTSESTAALGCLVK DYFPEPVTVSWNSGALTSGVHTFPAVLQSSGLYSLSSVVTVPSSSLGTKT YTCNVDHKPSNTKVDKRVESKYGPPCPPCPAPEAAGGPSVFLFPPKPKDT LMISRTPEVTCVVVDVSQEDPEVQFNWYVDGVEVHNAKTKPREEQFNSTY RVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLG |
| 13F1 humanized | Full light chain | 149 | EIVLTQSPATLSLSPGERATLSCRANSSVSSMHWYQQKPGQSPEPWIYAI SNLAFGVPARFSGSGSGTDYTLTISSLEPEDFAVYYCQQWSSRPPTFGQG TKLEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGL SSPVTKSFNRGEC |
| Human IgG1 | D265A mutation constant region | 150 | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVAVS HEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK |
| Human IgG4 constant region | F234A and L235A double mutation | 151 | ASTKGPSVFPLAPCSRSTSESTAALGCLVKDYFPEPVTVSWNSGALTSGV HTFPAVLQSSGLYSLSSVVTVPSSSLGTKTYTCNVDHKPSNTKVDKRVES KYGPPCPPCPAPEAAGGPSVFLFPPKPKDTLMISRTPEVTCVVVDVSQED PEVQFNWYVDGVEVHNAKTKPREEQFNSTYRVVSVLTVLHQDWLNGKEYK CKVSNKGLPSSIEKTISKAKGQPREPQVYTLPPSQEEMTKNQVSLTCLVK GFYPSDIAVEWESNGQPENNYKTTPPVLDSDGSFFLYSRLTVDKSRWQEG NVFSCSVMHEALHNHYTQKSLSLSLG |
| 7A4D humanized | Light chain variable | 152 | DIVLTQSPASLAVSPGQRATITCRASESVDNYGYSFMNWFQQKPGQPPKL LIYRASNLESGVPARFSGSGSRTDFTLTINPVEADDTANYYCQQSNADPT FGQGTKLEIK |

TABLE 3-continued

Light chain and heavy chain variable region sequences and full antibody sequences

| Name | Region[1] | SEQ ID NO | Sequence |
|---|---|---|---|
| 7A4D humanized | Full light chain | 153 | DIVLTQSPASLAVSPGQRATITCRASESVDNYGYSFMNWFQQKPGQPPKL LIYRASNLESGVPARFSGSGSRTDFTLTINPVEADDTANYYCQQSNADPT FGQGTKLEIKRTVAAPSVFIFPPSDEQLKSGTASVVCLLNNFYPREAKVQ WKVDNALQSGNSQESVTEQDSKDSTYSLSSTLTLSKADYEKHKVYACEVT HQGLSSPVTKSFNRGEC |

In one embodiment, the invention provides anti-PD-1 antibodies that comprise the light chain CDRs and heavy chain CDRs of antibodies 10D1, 4C10, 7D3, 13F1, 15H5, 14A6, 22A5, 6E1, 5A8, and/or 7A4. The person of skill in the art will understand that the heavy and light chain CDRs of the antibodies provided herein may be independently selected, or mixed and matched, to form an antibody or binding fragment thereof comprising any light chain CDR1, CDR2, and CDR3; and any heavy chain CDR1, CDR2, and CDR3 from the antibodies provided herein. Thus, the invention provides anti-PD-1 antibodies that comprise a light chain CDR1 comprising an amino acid sequence selected from the group consisting of SEQ ID NOs: 24, 34, 45, 55, 65, 75, 85, 95, 105, and 115; a light chain CDR2 comprising an amino acid sequence selected from the group consisting of SEQ ID NOs: 25, 35, 46, 56, 66, 76, 86, 96, 106, and 116; a light chain CDR3 comprising an amino acid sequence selected from the group consisting of SEQ ID NOs: 26, 36, 47, 57, 67, 77, 87, 97, 107, and 117; a heavy chain CDR1 comprising an amino acid sequence selected from the group consisting of SEQ ID NOs: 19, 29, 40, 50, 60, 70, 80, 90, 100, and 110; a heavy chain CDR2 comprising an amino acid sequence selected from the group consisting of SEQ ID NOs: 20, 30, 41, 51, 61, 71, 81, 91, 101, and 111; and a heavy chain CDR3 comprising an amino acid sequence selected from the group consisting of SEQ ID NOs: 21, 31, 42, 52, 62, 72, 82, 92, 102, and 112. In one embodiment, the present invention provides anti-PD-1 antibodies comprising heavy and light chain CDR regions comprising amino acid sequences having at least 75%, at least 80%, at least at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% homology to the corresponding light or heavy chain CDR1, CDR2, or CDR3 provided herein. In one embodiment, the present invention provides anti-PD-1 antibodies comprising heavy and light chain CDR regions comprising amino acid sequences having 1, 2, 3, 4, 5, or 6 amino acid substitutions, deletions, or insertions relative to the corresponding light or heavy chain CDR1, CDR2, or CDR3 provided herein.

In one embodiment, the invention provides anti-PD-1 antibodies that comprise a variable light chain of an antibody selected from the group consisting of 10D1, 4C10, 7D3, 13F1, 15H5, 14A6, 22A5, 6E1, 5A8, 7A4 and 7A4D and a variable heavy chain of an antibody selected from the group consisting of 10D1, 4C10, 7D3, 13F1, 15H5, 14A6, 22A5, 6E1, 5A8, and 7A4. In one embodiment, the antibodies and fragments provided herein comprise a light chain variable region comprising an amino acid sequence that is at least 75%, at least 80%, at least at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% homology to a light chain variable region according to SEQ ID NOs: 23, 33, 44, 54, 64, 74, 84, 94, 104, 114, 133, 143 and 152. In one embodiment, the antibodies and fragments provided herein comprise a light chain variable region comprising an amino acid sequence according to SEQ ID NO: 23, 33, 44, 54, 64, 74, 84, 94, 104, 114, 133, 143, 152, or a variant thereof, wherein the variant comprises 1, 2, 3, 4, 5, 6, 7, 8, 9, or 10 amino acid substitutions or deletions, or a combination thereof. In a further embodiment, the amino acid substitutions are conservative substitutions. In another embodiment, the amino acid substitutions improve the properties of the antibodies as provided herein, for example, by removing a deamidation site. For example, in one embodiment, an asparagine (Asn; N) residue is mutated. In a further embodiment, the Asn is mutated to aspartic acid (Asp; D). In a yet further embodiment, the Asn at position 85 in framework region 3 of the light chain variable region is mutated to Asp. In one embodiment, the present disclosure provides humanized antibody 7A4D, which comprises the same amino acid sequence as humanized antibody 7A4 except with a mutation in framework 3 (position 85) of the light chain to remove the deamidation site.

In one embodiment, the antibodies and fragments provided herein comprise a heavy chain variable region comprising an amino acid sequence that is at least 75%, at least 80%, at least at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% homology to a light chain variable region according to SEQ ID NOs: 18, 28, 39, 49, 59, 69, 79, 89, 99, 109, 131, and 141, or 84. In one embodiment, the antibodies and fragments provided herein comprise a heavy chain variable region comprising an amino acid sequence according to SEQ ID NO: 18, 28, 39, 49, 59, 69, 79, 89, 99, 109, 131, 141, or a variant thereof, wherein the variant comprises 1, 2, 3, 4, 5, 6, 7, 8, 9, 10, or more amino acid substitutions, insertions, or deletions, or a combination thereof. In a further embodiment, the amino acid substitutions are conservative substitutions. In another embodiment, the amino acid substitutions improve the properties of the antibodies as provided herein, for example, by removing a deamidation site. For example, in one embodiment, an asparagine (Asn; N) residue is mutated. In a further embodiment, the Asn is mutated to aspartic acid (Asp; D).

The anti-PD-1 antibodies disclosed herein having one or more amino acid substitution, insertion, deletion, or combination thereof in the CDR or variable light or heavy chain region retain the biological activity of the corresponding anti-PD-1 antibody that does not have an amino acid substitution, insertion, or deletion. Thus, the variant anti-PD-1 antibodies provided herein retain binding to PD-1. Percent homology, as used herein, refers to the number of identical amino acid sequences shared by two reference sequences, divided by the total number of amino acid positions, multiplied by 100.

In some embodiments, the anti-PD-1 antibodies provided herein comprise conservative amino acid substitutions. The person of skill in the art will recognize that a conservative amino acid substitution is a substitution of one amino acid with another amino acid that has a similar structural or chemical properties, such as, for example, a similar side chain. Exemplary conservative substitutions are described in the art, for example, in Watson et al., *Molecular Biology of the Gene*, The Bengamin/Cummings Publication Company, 4$^{th}$ Ed. (1987).

The skilled person will understand that the variable light and variable heavy chains may be independently selected, or mixed and matched, from the antibodies provided herein. Thus, the present invention provides anti-PD-1 antibodies comprising a light chain variable region having at least 80% homology to an amino acid sequence selected from the group consisting of SEQ ID NOs: 23, 33, 44, 54, 64, 74, 84, 94, 104, 114, 133, 143, and 152; and a heavy chain variable region having at least 80% homology to an amino acid sequence selected from the group consisting of SEQ ID NOs: 18, 28, 39, 49, 59, 69, 79, 89, 99, 109, 131, and 141.

In one embodiment, the present invention provides antibodies that bind to the same epitope as any one of the exemplary antibodies disclosed herein. Thus, in one embodiment, the present invention provides antibodies that compete for binding to PD-1 with the exemplary antibodies provided herein.

The anti-PD-1 antibodies and fragments thereof provided herein may further comprise Fc region modifications to alter effector functions. Fc modifications may be amino acid insertions, deletions, or substitutions, or may be chemical modifications. For example, Fc region modifications may be made to increase or decrease complement binding, to increase or decrease antibody-dependent cellular cytotoxicity, or to increase or decrease the half life of the antibody. Some Fc modifications increase or decrease the affinity of the antibody for an Fcγ receptor such as FcγRT, FcγRII, FcγRIII, or FcRn. Various Fc modifications have been described in the art, for example, in Shields et al., *J Biol. Chem* 276; 6591 (2001); Tai et al. *Blood* 119; 2074 (2012); Spiekermann et al. *J Exp. Med* 196; 303 (2002); Moore et al. *mAbs* 2:2; 181 (2010); Medzihradsky *Methods in Molecular Biology* 446; 293 (2008); Mannan et al. *Drug Metabolism and Disposition* 35; 86 (2007); and Idusogie et al. *J Immunol* 164; 4178 (2000). In some embodiments, Fc region glycosylation patters are altered. In other embodiments, the Fc region is modified by pegylation (e.g., by reacting the antibody or fragment thereof with polyethylene glycol (PEG).

In one embodiment, the antibodies or fragments thereof provided herein are immunoconjugates comprising an anti-PD-1 antibody or fragment thereof and further comprising an agent selected from the group including an additional therapeutic agent, a cytotoxic agent, an immunoadhesion molecule, and an imaging agent. In some embodiments, the imaging agent is selected from the group consisting of a radiolabel, an enzyme, a fluorescent label, a luminescent label, a bioluminescent label, a magnetic label, and biotin. In some embodiments, the imaging agent is a radiolabel selected from the group consisting of: $^{3}$H, $^{14}$C, $^{35}$S, $^{62}$, $^{64}$Cu, $^{89}$Zr, $^{90}$Y, $^{99}$TC, $^{111}$In, $^{125}$I, $^{131}$I, $^{177}$Lu, $^{166}$Ho, and $^{153}$Sm. In some embodiments, the therapeutic agent or cytotoxic agent is selected from the group including a chemotherapeutic agent, an immunosuppressive agent, an immuno-stimulatory agent, an anti-metabolite, an alkylating agent, an antibiotic, a growth factor, a cytokine, an anti-angiogenic agent, an anti-mitotic agent, an anthracycline, a toxin, and an apoptotic agent. In some embodiments, the binding protein is conjugated directly to the agent. In other embodiments, the binding protein is conjugated to the agent via a linker. Suitable linkers include, but are not limited to, amino acid and polypeptide linkers disclosed herein. Linkers may be cleavable or non-cleavable.

In one embodiment, the present invention provides bispecific or multispecific antibodies specific for PD-1 and at least one other antigen or epitope. The anti-PD-1 antibodies and fragments thereof provided herein may be tested for binding to PD-1 using the binding assays provided herein, or any other binding assay known in the art.

Unless otherwise stated, the practice of the present invention employs conventional molecular biology, cell biology, biochemistry, and immunology techniques that are well known in the art and described, for example, in Methods in Molecular Biology, Humana Press; Molecular Cloning: A Laboratory Manual, second edition (Sambrook et al., 1989), Current Protocols in Immunology (J. E. Coliganet al., eds., 1991); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Phage display: a laboratory manual (C. Barbas III et al, Cold Spring Harbor Laboratory Press, 2001); and Using antibodies: a laboratory manual (E. Harlow and D. Lane (Cold Spring Harbor Laboratory Press, 1999).

In one aspect the present invention provides methods for treating a subject for a disease or condition responsive to enhancing, stimulating, or eliciting an immune response. As used herein, the terms "treatment" or "treating" refers to both therapeutic treatment and prophylactic or preventive measures. Subjects in need of treatment include those subjects that already have the disease or condition, as well as those that may develop the disease or condition and in whom the object is to prevent, delay, or diminish the disease or condition. As used herein, the term "subject" denotes a mammal, such as a rodent, a feline, a canine, and a primate. Preferably, a subject according to the invention is a human.

The term "therapeutically effective amount," as used herein, refers to the amount of a compound or composition that is necessary to provide a therapeutic and/or preventative benefit to the subject.

In one aspect, the antibodies and antigen binding fragments thereof are useful in the treatment of solid or non-solid tumors. Thus, in one aspect, the present invention provides methods for treatment of cancer. "Cancer" as used herein refers to the physiological condition in mammals that is typically characterized by unregulated cell growth. Examples of cancer include but are not limited to carcinoma, lymphoma, blastoma, sarcoma (including liposarcoma, osteogenic sarcoma, angiosarcoma, endotheliosarcoma, leiomyosarcoma, chordoma, lymphangiosarcoma, lymphangioendotheliosarcoma, rhabdomyosarcoma, fibrosarcoma, myxosarcoma, chondrosarcoma), neuroendocrine tumors, mesothelioma, synovioma, schwanoma, meningioma, adenocarcinoma, melanoma, and leukemia or lymphoid malignancies. More particular examples of such cancers include squamous cell cancer (e.g. epithelial squamous cell cancer), Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, B-cell acute lymphoblastic leukemia/lymphoma, T-cell acute lymphoblastic leukemia/lymphoma, lung cancer including small-cell lung cancer, non-small cell lung cancer, adenocarcinoma of the lung and squamous carcinoma of the lung, small cell lung carcinoma, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, Ewing's tumor, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, myelodysplastic disease, heavy chain disease, neuroendocrine tumors, Schwanoma, and other carcinomas, as well as head and neck cancer.

In one embodiment, the antibodies and fragments thereof provided herein are useful in the treatment of diseases caused by infectious agents. Infectious agents include, but are not limited to, bacterial, mycological, parasitic, and viral agents. Examples of such infectious agents include the following: staphylococcus, methicillin-resistant staphylococcus aureus, Escherichia coli, streptococcaceae, neisseriaaceae, cocci, enterobacteriaceae, enterococcus, vancomycin-resistant enterococcus, cryptococcus, histoplasmosis, aspergillus, pseudomonadaceae, vibrionaceae, campylobacter, pasteurellaceae, bordetella, francisella, brucella, legionellaceae, bacteroidaceae, gram-negativebacilli, clostridium, corynebacterium, propionibacterium, gram-positive bacilli, anthrax, actinomyces, nocardia, mycobacterium, treponema, borrelia, leptospira, mycoplasma, ureaplasma, rickettsia, chlamydiae, candida, systemic mycoses, opportunistic mycoses, protozoa, nematodes, trematodes, cestodes, adenoviruses, herpesviruses (including, for example, herpes simplex virus and Epstein Barr virus, and herpes zoster virus), poxviruses, papovaviruses, hepatitis viruses, (including, for example, hepatitis B virus and hepatitis C virus), papilloma viruses, orthomyxoviruses (including, for example, influenza A, influenza B, and influenza C), paramyxoviruses, coronaviruses, picornaviruses, reoviruses, togaviruses, flaviviruses, bunyaviridae, rhabdoviruses, rotavirus, respiratory syncitial virus, human immunodeficiency virus and retroviruses. Exemplary infectious diseases include but are not limited to candidiasis, candidemia, aspergillosis, streptococcal pneumonia, streptococcal skin and oropharyngeal conditions, gram negative sepsis, tuberculosis, mononucleosis, influenza, respiratory illness caused by Respiratory Syncytial Virus, malaria, schistosomiasis, and trypanosomiasis.

In one embodiment, the antibodies and fragments thereof provided herein are useful in the treatment of diseases mediated by T-helper type 2 (Th2) T cells, such as, for example, asthma, allergy, or graft versus host disease.

In one embodiment, the antibodies and fragments thereof provided herein are useful in for the stimulation of an immune response in a subject in need thereof. For example, in one embodiment, the anti-PD-1 antibodies and fragments thereof may be administered in conjunction with an antigen of interest for the purpose of eliciting an immune response to said antigen. An antigen of interest may be an antigen associated with a pathogen such as a virus or bacterium. Thus, in one embodiment, the present invention provides a vaccine comprising an anti-PD-1 antibody and an antigen, wherein the vaccine elicits an antigen-specific immune response.

In one embodiment, the anti-PD-1 antibodies provided herein modulate regulatory T cell function. CD4+ CD25+ regulatory T cells are lymphocytes that suppress or reduce the effects of effector T cell functions. The terms "regulatory T cell" and "Treg" are used interchangeably herein. In one embodiment, the anti-PD-1 antibodies provided herein prevent or reverse the inhibitory effects of regulatory T cells on effector T cell cytokine production. For example, in one embodiment, the anti-PD-1 antibodies provided herein restore the capacity for IFNγ production to effector T cells in contact with regulatory T cells.

In one embodiment, the antibodies and fragments thereof disclosed herein may be administered to the subject by at least one route selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intracapsular, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intratympanic, intrauterine, intravesical, intravitreal, bolus, subconjunctival, vaginal, rectal, buccal, sublingual, intranasal, intratumoral, and transdermal.

In one embodiment, the antibodies and fragments thereof disclosed herein may be administered to a subject in need thereof in combination with one or more additional therapeutic agent. In one embodiment, the antibodies and fragments thereof may be administered to a subject before, during, and/or after administration to the subject of the additional therapeutic agent. In one embodiment, the additional therapeutic agent is a chemotherapeutic agent, radiotherapeutic agent, cytokine, antibody or fragment thereof, or any other additional therapeutic that is indicated for the disease to be treated. In one embodiment, the anti-PD-1 antibody and the additional therapeutic agent exhibit therapeutic synergy when administered together, whether concurrently or sequentially. In one embodiment, the anti-PD-1 antibody and the additional therapeutic agent are administered in separate formulations. In another embodiment, the anti-PD-1 antibody and the additional therapeutic agent are administered in the same formulation. In one embodiment, the anti-PD-1 antibodies and fragments provided herein enhance the immune modulating effect of the one or more additional therapeutic agent. In another embodiment, the one or more additional therapeutic agent enhances the effect of the anti-PD-1 antibody or fragment thereof.

The present invention provides isolated antibodies and antigen binding fragments thereof, and nucleic acids encoding such antibodies and fragments, as well as compositions comprising such isolated antibodies, fragments, and nucleic acids. The term "isolated" refers to a compound of interest (e.g., an antibody or nucleic acid) that has been separated from its natural environment. The present invention further provides pharmaceutical compositions comprising the isolated antibodies or fragments thereof, or nucleic acids encoding such antibodies or fragments, and further comprising one or more pharmaceutically acceptable carrier. Pharmaceutically acceptable carriers include, for example, excipients, diluents, encapsulating materials, fillers, buffers, or other agents.

The use of the singular includes the plural unless specifically stated otherwise. The word "a" or "an" means "at least one" unless specifically stated otherwise. The use of "or" means "and/or" unless stated otherwise. The meaning of the phrase "at least one" is equivalent to the meaning of the phrase "one or more." Furthermore, the use of the term "including," as well as other forms, such as "includes" and "included," is not limiting. Also, terms such as "element" or "component" encompass both elements or components comprising one unit and elements or components comprising more than one unit unless specifically stated otherwise.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of non-critical parameters that could be changed or modified to yield essentially similar results.

EXAMPLES

Example 1—Mouse Immunization and Production of Mouse Antibodies Against Human PD-1

To generate antibodies against the human PD-1, cDNAs encoding the open reading frame of the extracellular domain of hPD-1 fused with a histidine tag (hPD-1-HisTag, SEQ ID NO:1), mouse Fc (hPD-L1-mFc, SEQ ID NO:13), and human Fc tag (hPD-1-hFc, SEQ ID NO:5) were obtained by PCR and subcloned into expression vector pcDNA3.1 (In-vitrogen CAT#:V-790), respectively. After transient expression in freestyle 293 cells, hPD-1-HisTag was purified with NTA column (GE healthcare), hPD-1-mFc and hPD-1-hFc were purified with Protein G column (GE healthcare).

To immunize mice necessary for generating hybridoma cell lines, 100 µg of human PD-1-mouse Fc fusion protein or and a complete Freund's adjuvant in the same amount were mixed, and the mixture was administered via an subcutaneous injection to each of five 6 to 7-week-old BALB/c mice. After two weeks, the antigen (half the previously injected amount) was mixed with an incomplete Freund's adjuvant using the same method as described above, and the mixture was administered to each mouse via subcutaneous injection. After one week, final boosting was performed, and blood was collected from the tail of each mouse after three days to obtain serum. Then, serum was diluted at 1/1000 with PBS, and an ELISA was performed to analyze whether the titer of the antibody recognizing human PD-1-mFc increased. Afterwards, mice in which a sufficient amount of the antibody was obtained were selected, and a cell fusion process was performed on the selected mice.

Three days before a cell fusion experiment, a mixture of 50 µg of PBS and human PD-1-mFc fusion protein was administered via an intraperitoneal injection to each mouse. Each immunized mouse was anesthetized, and its spleen located on the left side of the body was then extracted and ground with a mesh to isolate cells, which were mixed with a culture medium (RPMI1640) to prepare a spleen cell suspension. The suspension was centrifuged to collect a cell layer. The obtained $1\times10^8$ of spleen cells were mixed with $1.5\times10^{-7}$ of myeloma cells (Sp2/0), and the mixture was centrifuged to precipitate the cells. The precipitate was slowly dispersed and treated with PEG Hybri-Max (Sigma Inc., CAT#:7181). The mixed cells were distributed into 96-well plates at 0.1 ml per well and incubated at 37° C., 5% $CO_2$ incubator. On day 1, the cells were fed by the addition of an additional 0.1 ml media containing serum and HAT plus 2× methotrexate for each well. On day 3 and day 7, 0.1 ml of medium from each well was replaced with 0.1 ml of fresh HT medium. The screening typically occurred between days 9-14.

Example 2—Selection of the Hybridoma Cells that Produce Monoclonal Antibodies Against Human PD-1 Protein Based on ELISA and FACS Analyses ELISA binding analysis was conducted based on human PD-1-hFc Protein. 96-well plates (Costar, Cat No: 9018) were coated with 100 µL of 2 µg/ml PD1-hFc (CrownBio) in coating buffer (PBS, Hyclone, Cat No: SH30256.01B) overnight at 4° C. The wells were aspirated and non-specific binding sites were blocked by adding 200 µL of blocking buffer with 1% (w/v) of bovine serum albumin (BSA, Roche, Cat No: 738328) and incubating for 1 hour at 37° C. After the plates are washed three times with wash buffer (PBS with 0.05% (v/v) Tween20 (Sigma, Cat No: P1379), 100 µL/well of a suitable dilutions of hybridoma supernatant in blocking buffer were added and incubated at room temperature for 1 hour. The plates were washed and incubated with 100 µL/well of Goat anti-Mouse IgG (H+L) (Thermo, Cat No: 31432) in blocking buffer for 60 min. After the plates were washed, 100 µL/well of substrate solution (TMB (eBioscience, Cat No: 00-4201-56) was added and the plates were incubated for 2 min at room temperature. 100 µL/well of stop solution (2N H2SO4) was added to stop the reaction. The colorimetric signals were developed and read at 450 nm using a Auto Plate SpectraMax Plus (Supplier: Molecular Devices; Model: MNR0643; Software: SoftMax Pro v5.4). Through this method, hybridoma cell lines that produce antibodies highly specifically binding to the human PD-1 protein were repeatedly selected.

ELISA based ligand blockage analysis was conducted via blocking biotinylated human PD-L1-mFcs from binding to human PD-1-hFc. PD-1-mFc antigen (CrownBio) was suspended in PBS (Hyclone, Cat No: SH30256.01B) buffer (2 ug/ml, 100 ul/well) and coated on the 96 well plate (costar, Cat No.:9018) 4° C. overnight. Plates were washed 3 times using washing buffer: PBS+0.05% Tween 20(Sigma, Cat No.:P1379). 200 ul of blocking buffer (PBS+1% BSA (Roche, Cat No.:738328)), was added to each well, incubated at 37° C. for 1 hour, and washed 3 times. Various concentrations (suitable dilutions of hybridoma supernatant in PBS) of the anti-PD-1 Abs were added to the wells (100 μl/well) and incubated at 37° C. for 1 hour. Ligand was added (0.1 ug/ml PDL-1-mFc-biotin, 100 μl/well), incubated at 37° C. for 2 h, and washed 3 times. Secondary antibody (Avidin HRP eBioscience cat No.:E07418-1632, 1:500, 100 ul/well) was added, incubated at 37° C. for 0.5 hour, and washed 3 times. TMB (Sigma, Cat No.: T0440, 100 ul/well) was added, and incubated for 3 min at RT. To stop the reaction, 2N H2SO4 (100 ul/well), was added. The colorimetric signals were developed and read at 450 nm using a Auto Plate SpectraMax Plus (Supplier: Molecular Devices; Model: MNR0643; Software: SoftMax Pro v5.4).

Cell binding analysis of antibodies was performed based on hPD-1-293T cell line. $2 \times 10^5$ 293T-PD-1 cells were used for each reaction by putting them into each well of 96-well culture plates. The cells were incubated with the indicated antibody (20 ug/ml with the dilution of 1/3) at 4° C. for 1 h. Cells were washed three times with FACS buffer. A secondary antibody (PE Goat anti-mouse: 1:200; PE mouse anti-human: 1:10) was added to the cells at 100 ul/well, and incubated at 4° C. for 40 min. Cells were washed three times with FACS buffer and analyzed by FACS Array.

FACS based ligand blockage analysis was conducted to determine the anti-PD-1 hybridoma antibodies in the blockage of biotinylated human PD-L1 and PD-L2 binding to hPD-1-293T cells using a flow cytometry assay. PD-1 expressing 293T cells were suspended in FACS buffer (PBS with 3% fetal calf serum). Various concentrations of the testing hybridoma antibodies were added to the cell suspension and incubated at 4° C. for 60 minutes in 96 well plates. Biotin-labeled PD-L1 protein or Biotin-labeled PD-L2 protein was added into the wells and incubated at 4° C. for 60 minutes. Plates were washed 3 times, and mouse anti-biotin PE antibody (Biolgend, cat#409004) was added. Flow cytometric analyses were performed using a FACS Array. The results of the study are depicted in FIG. 1A (PD-L1) and FIG. 1B (PD-L2). The anti-PD-1 monoclonal antibodies blocked binding of PD-L1 or PD-L2 to 293T cells transfected with human PD-1, as measured by the mean fluorescent intensity (MFI) of staining. These data demonstrated that the anti-PD-1 antibodies block binding of ligand PD-L1 and PD-L2 to cell surface PD-1.

Example 3—Subcloning to Obtain Monoclonal Antibody Clones and Purification of Anti-hPD-1 Antibodies Subcloning is based on the procedure of limited dilution, and is designed to obtain individual hybridoma clones producing monoclonal antibodies. Each of the hybridomas was subjected to multiple rounds (4 rounds) of limiting dilution. For each round of subcloning, the clones were tested by ELISA and FACS based blockage analyses.

Antibody purification was conducted for a total of twenty two anti-hPD-1 hybridoma antibodies. The hybridoma cells were cultured in Dulbecco's Modified Eagle's medium (GIBCO; Invitrogen Corporation, Carlsbad, Calif.) containing 10% fetal calf serum, 1% penicillin/streptomycin, 2% L-glutamine, and 1% adjusted NaHCO$_3$ solution. The selected hybridoma cells were then adapted in serum free culture medium and the antibody was purified from the supernatant using Protein-G column (GE healthcare). After washing with PBS, bound antibodies were eluted using 0.1 M Glycine pH3.0, followed by pH neutralization using 2.0 M Tris. Ultra-15 centrifugal concentrators (Amicon) were used for buffer exchanging and antibody concentrating.

Example 4—Characterization of the Purified Murine Anti-hPD-1 Antibodies in Binding and Ligand Blockage Activities Based on ELISA and FACS Analyses The purified hybridoma antibodies were characterized further based on ELISA and FACS analyses. The methods used were similar to those described above in Example 2 except that in these cases, purified antibodies were measured in amount and concentration, and the results were used to calculate EC50 and IC50 values. The following tables, Tables 1-5, show the results of 10 antibodies.

TABLE 1

ELISA based binding EC50 of 10 murine anti-PD-1 antibodies

| ng/ml | 15H5 | 22A5 | 14A6 | 6E1 | 7D3 | 10D1 | 4C10 | 13F1 | 5A8 | 7A4 |
|---|---|---|---|---|---|---|---|---|---|---|
| EC50 | 13.35 | 19.38 | 7.07 | 15.67 | 24.36 | 17.18 | 13.25 | 17.33 | 11.25 | 9.32 |

TABLE 2

ELISA based blockage IC50 of 10 murine anti-PD-1 antibodies

| ng/ml | 15H5 | 22A5 | 14A6 | 6E1 | 7D3 | 10D1 | 4C10 | 13F1 | 5A8 | 7A4 |
|---|---|---|---|---|---|---|---|---|---|---|
| IC50 | 873.2 | 1114.8 | 923 | 961.2 | 982.0 | 1409 | 1464.3 | 701.0 | 1128.7 | 698.8 |

TABLE 3

FACS based binding EC50 of 10 murine anti-PD-1 antibodies

| ng/ml | 15H5 | 22A5 | 14A6 | 6.00E+01 | 7D3 | 10D1 | 4C10 | 13F1 | 5A8 | 7A4 |
|---|---|---|---|---|---|---|---|---|---|---|
| EC50 | 45.37 | 77.45 | NA | 49.09 | 52.66 | NA | 108.9 | 30.79 | NA | 38.93 |

TABLE 4

FACS based PD-L1 blockage IC50 of 10 murine anti-PD-1 antibodies selected.

| ng/ml | 15H5 | 22A5 | 14A6 | 6E1 | 7D3 | 10D1 | 4C10 | 13F1 | 5A8 | 7A4 |
|---|---|---|---|---|---|---|---|---|---|---|
| IC50 | 35.64 | 56.22 | 21.13 | 26.85 | 38 | 36.9 | 83.32 | 19.86 | 28.22 | 28.85 |

TABLE 5

FACS based PD-L2 blockage IC50 of 10 murine anti-PD-1 antibodies selected

| ng/ml | 15H5 | 22A5 | 14A6 | 6E1 | 7D3 | 10D1 | 4C10 | 13F1 | 5A8 | 7A4 |
|---|---|---|---|---|---|---|---|---|---|---|
| IC50 | 63.04 | 210.1 | 91.98 | 113.7 | 140.5 | 150 | 250.7 | 52.93 | 18.84 | 4.45 |

Example 5—Biacore Analysis of the Murine Anti-PD-1 Antibodies

To further characterize the binding characteristics of the antibodies, 10 hybridoma antibodies were profiled using Biacore (Biacore 3000, GE) to elucidate binding kinetics and calculate equilibrium binding constants. This assay was performed by capture method, using the mouse antibody capture kit (BR-1008-38, GE). After diluting anti-mouse Fc mab to 25 μg/ml in pH 5.0 immobilization buffer, immobilization was conducted with the parameters shown in Table 6 at a flow rate of 5 μl/min. The kinetic runs were done by 1) injecting ligand for typical 0.5-1 min at flow rate of 10 μl/min.; 2) injecting analytes of choice for typical 3 min followed by dissociation in running buffer (1× PBS-P20) for typical 5-10 min at flow rate of 30 μl/min.; and 3) injecting regeneration solution 10 mM Glycine pH1.7 for typical 1-2 min at flow rate of 10 μl/min.

TABLE 6

Biacore parameters.

| Event | Injection | Conditions |
|---|---|---|
| Activation | EDC/NHS (1:1 Mix) | 7 minutes |
| Immobilization | Diluted Anti-human Fc mAb | 4 minutes to achieve ~7000 RU Immobilization level |
| Deactivation | Ethanolamine-HCl | 7 minutes |

The results of the study are shown in Table 7. Each of the anti-human PD1 antibodies exhibited an association rate (ka) in the range of 1.11E+05 1/Ms to 8.40E+05 1/Ms; a dissociation rate (kd) in the range of 2.83E-05 1/s to 7.55E-05 1/s; an equilibrium association constant (KA) in the range of 1.60E+10 1/M to 5.44E+10 1/M; and an affinity (KD) in the range of 1.84E-11 M to 6.23E-11 M (0.0184 nM to 0.0623 nM).

TABLE 7

KD values of anti-PD-1 hybridoma antibodies.

| | ka (1/Ms) | kd (1/s) | KA (1/M) | KD (M) |
|---|---|---|---|---|
| 10D1 | 8.40E+05 | 5.24E-05 | 1.60E+10 | 6.23E-11 |
| 14A6 | 1.51E+06 | 4.52E-05 | 3.33E+10 | 3.00E-11 |
| 22A5 | 1.49E+06 | 2.88E-05 | 5.17E+10 | 1.93E-11 |
| 4C10 | 7.91E+05 | 2.63E-05 | 3.01E+10 | 3.32E-11 |
| 7A4 | 1.96E+06 | 4.82E-05 | 4.06E+10 | 2.46E-11 |
| 6E1 | 1.11E+06 | 2.83E-05 | 3.92E+10 | 2.55E-11 |
| 13F1 | 1.41E+06 | 3.92E-05 | 3.60E+10 | 2.78E-11 |
| 15H5 | 2.00E+06 | 3.67E-05 | 5.44E+10 | 1.84E-11 |
| 5A8 | 1.29E+06 | 7.55E-05 | 1.70E+10 | 5.87E-11 |
| 7D3 | 1.14E+06 | 2.83E-05 | 4.02E+10 | 2.49E-11 |

Example 6—Cross-Reactivity Among Species and Among Similar Molecules

To assess the species cross-reactivity of the antibodies, the mouse and cynomolgus macaque PD-1 receptors were cloned by PCR and stably transfected 293T-PD-1 cells were generated. The antibodies were tested for binding to the cynomolgus receptor using protein based ELISA. The results of the study showed that the antibodies bind with equal affinity to human and cynomolgus PD-1 and block binding of hPD-L1/Fc and hPD-L2/Fc to cynomolgous PD-1 with similar efficacy as compared to human PD-1. None of the antibodies selected bound mouse PD-1 with detectable affinity in any of the assays used. None cross reacts with human CTLA4, ICOS and CD28 (see Table 8).

Figure 3:
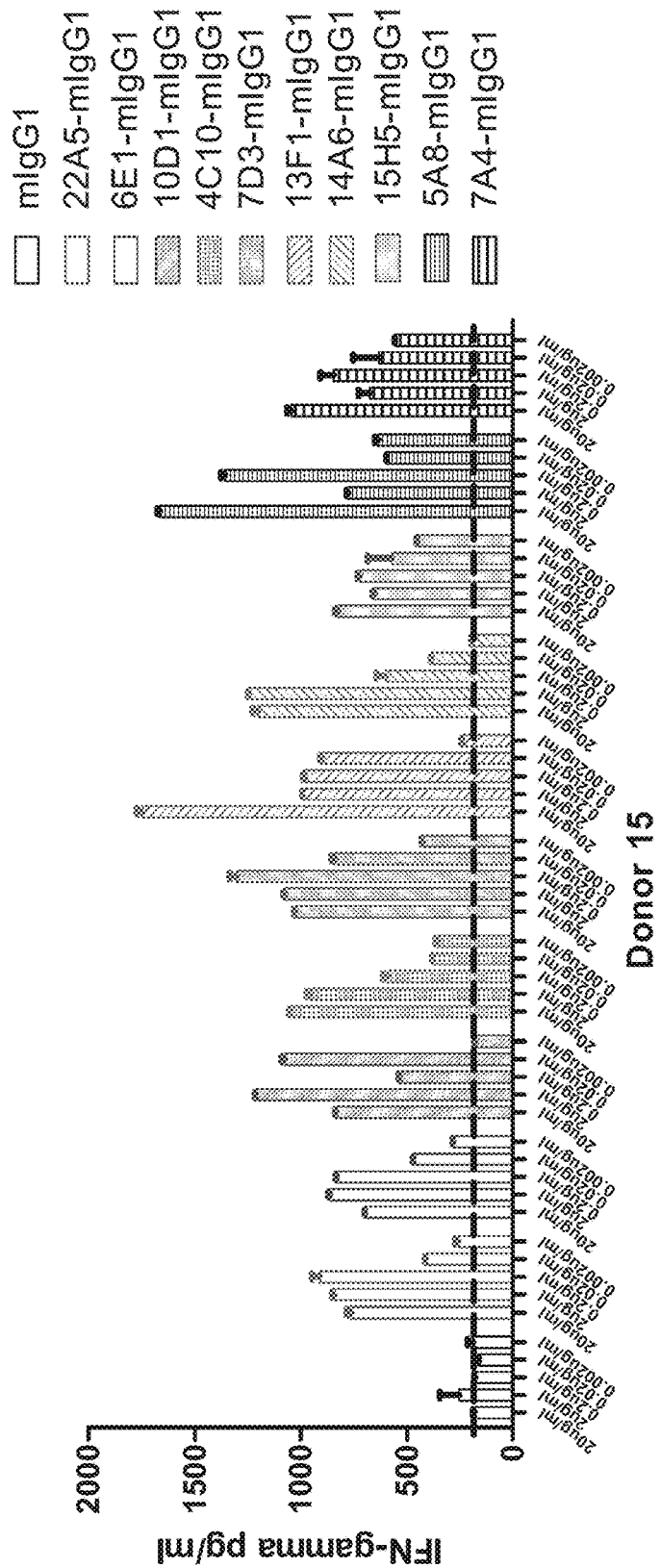
FIG. 3 is a graph showing IFN-γ (pg/mL) production in an MLR in response to different concentrations of murine anti-PD-1 antibodies. The anti-PD-1 antibodies tested were, from left to right, control mIgG1, 22A5-mIgG1, 6E1-mIgG1, 10D1-mIgG1, 4C10-mIgG1, 7D3-mIgG1, 13F1-mIgG1, 14A6-mIgG1, 15H5-mIgG1, 5A8-mIgG1, and 7A4-mIgG1. As shown on the x-axis, each antibody was tested at 20 µg/mL, 2 µg/mL, 0.2 µg/mL, 0.02 µg/mL, and 0.002 µg/mL.

Example 7—Effect of the Anti-PD-1 Hybridoma Antibodies on Cytokine Production in a Mixed Lymphocyte Reaction A mixed lymphocyte reaction was used to demonstrate the effect of blocking the PD-1 pathway on lymphocyte effector cells. T cells in the assay were tested for proliferation, IFN-γ secretion and IL-2 secretion in the presence or absence of a murine anti-human PD-1 monoclonal antibody. In the assay, human CD4+ T-cells were purified from PBMC using a CD4+ negative selection (Miltenyi Biotech, cat#130-091-155). Mature Dendritic cells (DC) were derived from purified monocytes (Miltenyi, Mo-DC Generation Toolbox, cat#130-093-568) culture with Mo-DC Differentiation Medium for 7 days; then, DC maturation was induced with Mo-Dc Maturation for 2 days. Each culture contained $10^5$ purified T-cells and $10^4$ allogeneic dendritic cells in a total volume of 200 μl. Anti-PD-1 monoclonal antibody 4C10, 5A8, 6E1, 7D3, 7A4, 10D1, 13F1, 14A6, 15H5, or 22A5 was added to each culture at different antibody concentrations. Either no antibody or an isotype control antibody was used as a negative control. The cells were cultured for 5 days at 37° C. On 5 day, 50 µl of medium was collected for measurement of IL-2 and IFN-γ. The levels of IFN-γ and IL-2 in the culture fluid were measured using an EIA hIFN-γ ELISA kit (R&D, cat#DY285) and IL-2 ELISA kit (eBioscience) The results of the study are provided in FIG. 2 (IL-2 secretion) and FIG. 3 (IFN-γ secretion) and show that the anti-human PD-1 monoclonal antibodies promoted T-cell proliferation, IFN-γ secretion and IL-2 secretion in a concentration dependent manner. In contrast, cultures containing the isotype control antibody did not show an increase in T cell proliferation, IFN-γ or IL-2 secretion.

Example 8—Features of 10 Murine Anti-hPD-1 Antibodies

Characteristics of 10 anti-PD1 monoclonal antibodies that were purified and characterized are summarized in Table 8. These antibodies bound tightly to PD-1 (with dissociation constants in the 20 uM to 3 nM range) and were capable of blocking the interaction with both PD-L1 and PD-L2 with varying IC50 values. Each of the antibodies induced IL2 and IFNγ production. None of the 10 antibodies crossreacted with CTLA4, ICOS, or CD28. Each of the antibodies bound cynomolgous PD-1. Each of the antibodies, when added in solution acted as receptor antagonists, ultimately enhanced T cell responses (see Example 5).

bromide. DNA fragments having the expected sizes (approximately 400 bp for the heavy chain and the light chain) were excised from the gel and purified.3 µl of purified PCR product were cloned into the pMD-18T vector (Takara, CAT#:D101A) and transformed into One Shot® TOP10 Chemically Competent E. coli (Invitrogen, CAT#:C4040-03). Clones were screened by colony PCR using universal M13 forward and reverse primers, and 10 positive clones from each reaction were chosen for DNA sequencing in both directions using M13 forward and M13 reverse primers.

The variable region sequences of antibodies 4C10 (SEQ ID NOs: 28, 33), 5A8 (SEQ ID NOs: 99, 104), 6E1 (SEQ ID NOs: 89, 94), 7D3 (SEQ ID NOs: 39, 44), 7A4 (SEQ ID NOs: 109, 114), 10D1 (SEQ ID NOs: 18, 23), 13F1 (SEQ ID NOs: 49, 54), 14A6 (SEQ ID NOs:69, 74), 15H5 (SEQ ID NOs: 59, 64) and 22A5 (SEQ ID NOs: 79, 84) were amplified from the corresponding hybridoma clones. These antibodies showed desired functions, such as blocking PD-1 binding to PD-L1 and enhanced T cell activation and cytokine release.

Construction and Expression of Chimeric 7A4 and 13F1 Antibody

7A4 and 13F1 chimeric light chains (SEQ ID NOs: 123 and 129, respectively) were constructed by linking the PCR-cloned cDNAs of mouse VL regions to human kappa and IgG1, respectively. 7A4 and 13F1 chimeric IgG1 heavy

TABLE 8

Summary of characterized features of 10 Murine anti-hPD-1 antibodies.

| No. | Selected Abs | KD (Biacore) | ELISA Binding EC50 (ng/ml) | FACS at 20 ug/ml | Blockage ELISA EC50 (ug/ml) | PD-L1 Blockage FACS EC50 (ng/ml) | PD-L2 Blockage FACS EC50 (ng/ml) | Tcell activation IL2 | Tcell activation IFN-g | Interaction with CTLA4, ICOS CD28 | Interaction with cyno-PD-1 |
|---|---|---|---|---|---|---|---|---|---|---|---|
| 1 | 15H5 | 1.84E−11 | 13.35 | +++ | 873.2 | 35.64 | 63.04 | +++ | ++ | − | +++ |
| 2 | 22A5 | 1.93E−11 | 19.38 | +++ | 1114.8 | 56.22 | 210.10 | +++ | ++ | − | +++ |
| 3 | 14A6 | 3.00E−11 | 7.07 | +++ | 923 | 21.13 | 91.98 | +++ | +++ | − | +++ |
| 4 | 6E1 | 2.55E−11 | 15.67 | +++ | 961.2 | 26.85 | 113.70 | +++ | ++ | − | +++ |
| 5 | 7D3 | 2.49E−11 | 24.36 | +++ | 982 | 38 | 140.50 | ++ | +++ | − | +++ |
| 6 | 10D1 | 6.23E−11 | 17.18 | +++ | 1409 | 36.9 | 150.00 | +++ | +++ | − | +++ |
| 7 | 4C10 | 3.32E−11 | 13.25 | +++ | 1464.3 | 83.32 | 250.70 | +++ | +++ | − | +++ |
| 8 | 13F1 | 2.78E−11 | 17.33 | +++ | 701 | 19.86 | 52.93 | +++ | ++++ | − | +++ |
| 9 | 5A8 | 5.87E−11 | 11.25 | +++ | 1128.7 | 28.22 | 18.84 | +++ | +++ | − | +++ |
| 10 | 7A4 | NA | 9.32 | +++ | 698.8 | 28.85 | 4.45 | ++++ | +++ | − | +++ |

Example 9—Anti-PD-1 Antibody cDNA Sequences Cloning and Humanization

Cloning of Immunoglobulin cDNAs

Total RNA isolated from the hybridoma cell line producing hPD-1 antibody by RNeasy Mini Kit (Qiagen, CAT#: 74104) was used as the template to synthesize first-strand cDNA with SuperScript® II Reverse Transcriptase (Life Technology, CAT#.18064-14) according to the manufacturer's instructions. The cDNA product was then subjected to PCR in a 50 µl volume reaction mixture using degenerate mouse IgG primers (Kettleborough Calif., et al, European Journal of Immunology 23: 206-211 (1993), Strebe N, et al, Antibody Engineering 1:3-14 (2010)). The reaction was carried out in a S1000™ Thermal Cycler (Bio-Rad, CAT#: 184-2000) with 30 cycles of: 94° C., 1.5 minutes for denaturation; 50° C., 1 minutes for annealing; and 72° C., 1 minute for synthesis. At the end of the 30th cycle, the reaction mixture was incubated another 7 minutes at 72° C. for extension.

The PCR mixture was subjected to electrophoresis in a 1% agarose/Tris-Borate gel containing 0.5 µg/ml ethidium chains (SEQ ID NOs: 119 and 125, respectively) were constructed by linking the PCR-cloned cDNAs of mouse VH regions to human IgG1 constant region. 7A4 and 13F1 chimeric IgG4 heavy chains (SEQ ID NOs: 121 and 127, respectively) were constructed by linking the PCR-cloned cDNAs of mouse VH regions to human IgG4 constant region The 5'ends of the mouse cDNA sequences were modified using PCR primers designed to add a leader sequence to both light chain and heavy chain.

Freestyle 293 cells (200 mL at 10⁶/mL) were transfected with 100 µg of each of the chimeric heavy and light chain expression plasmids and cultured for 6 days. The chimeric antibody in the supernatant was then purified with Protein-G column (GE healthcare). Binding of the chimeric antibodies to PD-1 was measured by ELISA and Biacore as described above in Examples 2 and 5, and was shown to bind to PD-1 with comparable affinity to that of the murine parent antibody. Table 9 shows the binding EC50 of each of the chimeric anti-PD-1 antibodies as measured by ELISA. Table 10 shows the PD-L1 blockage IC50 of each of the chimeric anti-PD-1 antibodies as measured by ELISA. Table 11 shows the binding EC50 of each of the chimeric anti-PD-1 antibodies as measured by FACS. Table 12 shows the PD-L1 blockage IC50 of each of the chimeric anti-PD-1 antibodies as measured by FACS.

TABLE 9

ELISA based binding EC50 of chimeric anti-PD-1 antibodies

| ng/ml | 15H5 hIgG4 | 22A5 hIgG4 | 14A6 hIgG4 | 6E1 hIgG4 | 7D3 hIgG4 | 10D1 hIgG4 | 4C10 hIgG4 | 13F1 hIgG4 | 7A4 hIgG4 |
|---|---|---|---|---|---|---|---|---|---|
| EC50(ug/ml) | 81.8 | 41.3 | 64.6 | 32.54 | 51.7 | 58.8 | 94.56 | 58.73 | 62 |

TABLE 10

ELISA based blockage IC50 of chimeric anti-PD-1 antibodies

| ng/ml | 15H5 hIgG4 | 22A5 hIgG4 | 14A6 hIgG4 | 6E1 hIgG4 | 7D3 hIgG4 | 10D1 hIgG4 | 4C10 hIgG4 | 13F1 hIgG4 | 7A4 hIgG4 |
|---|---|---|---|---|---|---|---|---|---|
| IC50 | 1367.0 | 1010.9 | 823.4 | 868.6 | 948.1 | 1034.5 | 977.6 | 856.2 | 871.1 |

TABLE 11

FACS based binding EC50 of chimeric anti-PD-1 antibodies

| ng/ml | 15H5 hIgG4 | 22A5 hIgG4 | 14A6 hIgG4 | 6E1 hIgG4 | 7D3 hIgG4 | 10D1 hIgG4 | 4C10 hIgG4 | 13F1 hIgG4 | 7A4 hIgG4 |
|---|---|---|---|---|---|---|---|---|---|
| EC50 | 243.6 | 145.3 | 103.4 | 143.1 | 130.9 | 218.8 | 220.6 | 113.1 | 91.6 |

TABLE 12

FACS based PD-L1 blockage IC50 of chimeric anti-PD-1 antibodies

| ng/ml | 15H5 hIgG4 | 22A5 hIgG4 | 14A6 hIgG4 | 6E1 hIgG4 | 7D3 hIgG4 | 10D1 hIgG4 | 4C10 hIgG4 | 13F1 hIgG4 | 7A4 hIgG4 |
|---|---|---|---|---|---|---|---|---|---|
| IC50 | 100.5 | 84.26 | 61.37 | 54.01 | NA | 40.33 | 129 | 52.13 | 70.55 |

Figure 4:
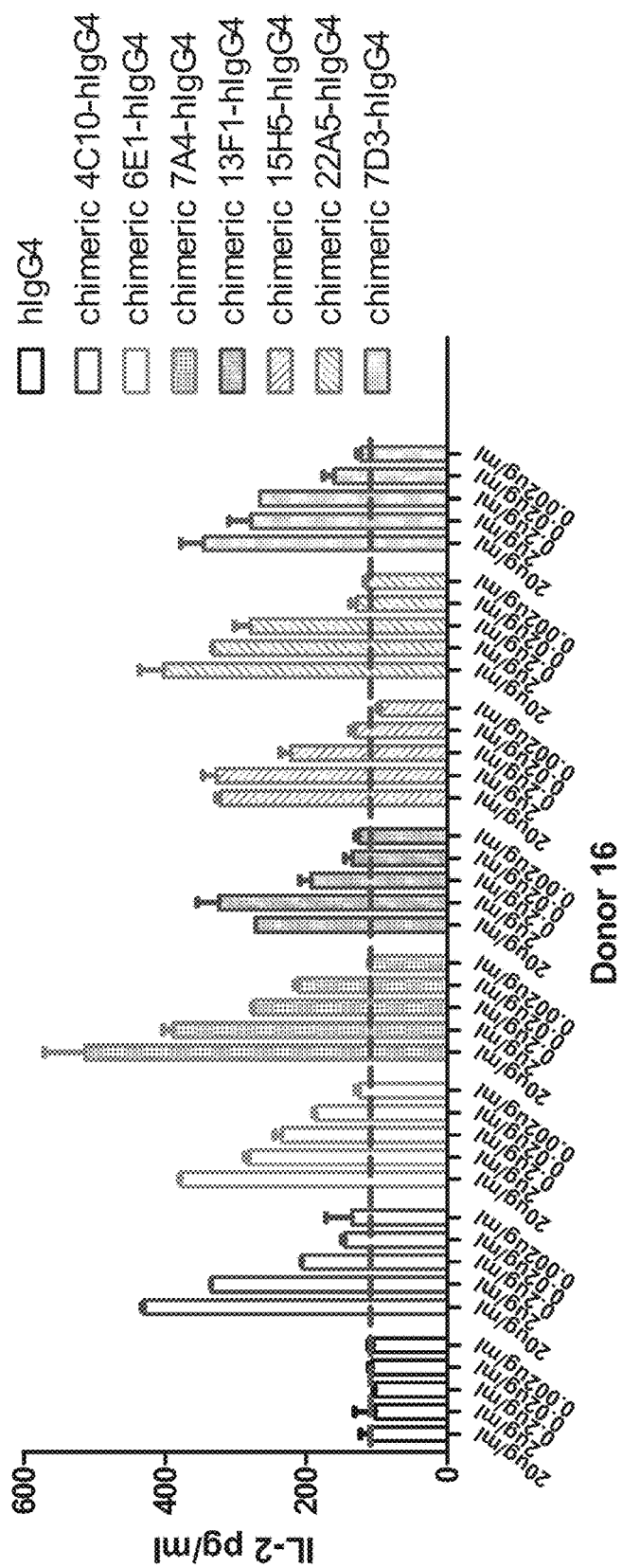
FIG. 4 is a graph showing IL-2 (pg/mL) production in an MLR in response to different concentrations of chimeric anti-PD-1 antibodies. The chimeric anti-PD-1 antibodies tested were, from left to right, control hIgG4, chimeric 4C10-hIgG4, chimeric 6E1-hIgG4, chimeric 7A4-hIgG4, chimeric 13F1-hIgG4, chimeric 15H5-hIgG4, chimeric 22A5-hIgG4, and chimeric 7D3-hIgG4. As shown on the x-axis, each antibody was tested at 20 µg/mL, 2 µg/mL, 0.2 µg/mL, 0.02 µg/mL, and 0.002 µg/mL.
Figure 5:
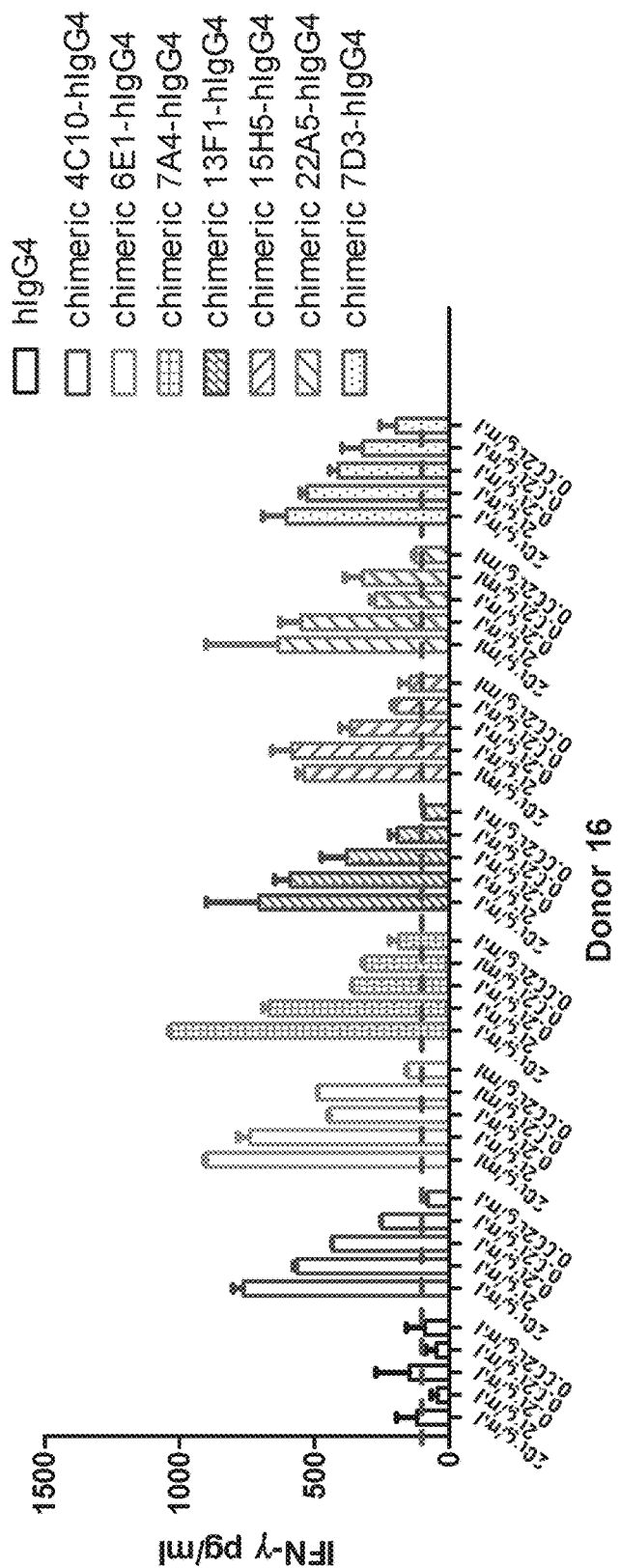
FIG. 5 is a graph showing IFN-γ (pg/mL) production in an MLR in response to different concentrations of chimeric anti-PD-1 antibodies. The chimeric anti-PD-1 antibodies tested were, from left to right, control hIgG4, chimeric 4C10-hIgG4, chimeric 6E1-hIgG4, chimeric 7A4-hIgG4, chimeric 13F1-hIgG4, chimeric 15H5-hIgG4, chimeric 22A5-hIgG4, and chimeric 7D3-hIgG4. As shown on the x-axis, each antibody was tested at 20 µg/mL, 2 µg/mL, 0.2 µg/mL, 0.02 µg/mL, and 0.002 µg/mL.

Mixed lympohcyte reactions as described above in Example 7 were used to determine the effect of the chimeric anti-PD-1 antibodies on IL-2 secretion (FIG. 4) and IFN-γ secretion (FIG. 5) from T cells. Each of the chimeric anti-PD-1 monoclonal antibodies promoted IL-2 secretion and IFNγ secretion in a concentration dependent manner in the MLR assay. In contrast, the isotype control antibody (hIgG4) did not elicit IL-2 secretion or IFNγ secretion at any concentration tested.

Antibody Humanization Design

7A4 and 13F1 antibody were humanized using a CDR grafting approach (U.S. Pat. No. 5,225,539, incorporated herein by reference in its entirety). The light chain and heavy chain variable chain sequences of the murine antibody 7A4 and 13F1 were compared to those available in the Research Collaboratory for Structural Bioinformatics (RCSB) protein databank by searching the NCBI database, http://www.ncbi.nlm.nih.gov/igblast/igblast.cgi. The model of 7A4 and 13F1 were generated respectively based on the VH and VL structure with the highest sequence homology.

The template human antibodies to be grafted with the complementary determining regions (CDRs) in the VH and VL of mouse 7A4 and 13F1 antibody were selected from human antibody germlines having an amino acid sequence with high homology with the mouse 7A4 and 13F1 antibody by searching the IMGT/Domain Gap Align 3D structure database, http://www.imgt.org/3Dstructure-DB/cgi/DomainGapAlign.cgi. For 7A4, the template human VH selected was a combination of IGHV2-5*10 and IGHJ4*01, and template human VL selected was a combination of IGKV1-33*01 and IGKJ2*01. For 13F1, the template human VH selected was a combination of IGHV3-21*04 and IGHJ4*01, and template human VL selected was a combination of IGKV7-3*01 and IGKJ2*01.

CDR amino acid sequences of the aforementioned template human antibodies were substituted by the amino acid sequence of CDRs of mouse 7A4 and 13F1 antibody. In addition, the frameworks of the above-mentioned template human antibody VH and VL were grafted with the necessary amino acid sequences from VH and VL of mouse 7A4 and 13F1 antibody to give a functional humanized antibody. As for VH and VL of 7A4 and 13F1, several sites of framework amino acid of the aforementioned template human antibody were back mutated to the corresponding amino acid sequences in mouse 7A4 and 13F1 antibody. For the light chain variable region of humanized 7A4 antibody, the amino acid at position 40 was mutated from Tyr (Y) to Phe (F) and the amino acid at position 72 was mutated from Gly (G) to Arg (R); and for the heavy chain variable region of humanized 7A4 antibody, the amino acid at position 2 was mutated from Val (V) to Ile (I), the amino acid at position 46 was mutated from Glu (E) to Lys (K), and the amino acid at position 70 was mutated from Phe (F) to Ile (I). For the light chain variable region of humanized 13F1 antibody, the amino acid at position 45 was mutated from Leu (L) to Pro (P) and the amino acid at position 70 was mutated from Phe (F) to Tyr (Y); and for the heavy chain variable region of humanized 13F1 antibody, the amino acid at position 26 was mutated from Gly (G) to Tyr (Y), the amino acid at position 48 was mutated from Ile (I) to Met (M), the amino acid at position 49 was mutated from Gly (G) to Ala (A), the amino acid at position 67 was mutated from Val (V) to Ile (I), and the amino acid at position 71 was mutated from Val (V) to Arg (R).

The amino acid sequences of the variable light and variable heavy chains of humanized 13F1 antibody were designated SEQ ID NOs: 143 and 141, respectively. The base sequences of DNAs encoding the amino acid sequences were designed (SEQ ID NO: 140 and 142, respectively). The amino acid sequences of the variable light and variable heavy chains of humanized 7A4 antibody were designated SEQ ID NOs: 133 and 131, respectively. The base sequences of DNAs encoding the amino acid sequences were designed (SEQ ID NO: 130 and 132, respectively).

IgG1 and IgG4 versions of the humanized 7A4 and 13F1 antibodies were produced (h13F1-IgG1, h13F1-IgG4, h7A4-IgG1 and h7A4-IgG4). The IgG1 constant region carries D265A mutation (Clynes R, et al, Nature Medicine 6: 443-446 (2000)) while IgG4 constant region has F234A and L235A double mutation (Xu D, et al, Cellular Immunology 200: 16-26 (2000)). The constant region sequences are disclosed in SEQ ID NOS: 150 and 151. The full light and heavy chain amino acid sequences for h13F1-IgG1 (SEQ ID NOs: 149 and 145), h13F1-IgG4 (SEQ ID NOs: 149 and 147), h7A4-IgG1 (SEQ ID NOs: 139 and 135), and h7A4-IgG4 (SEQ ID NOs: 139 and 137) are provided above in Table 3. To remove the potential deamidation site in the light chain of 7A4, Asn85 is mutated to Asp (h7A4D). The light chain variable region (SEQ ID NO: 152) and full light amino acid sequences (SEQ ID NO: 153) are also provided above in Table 3.

Construction and Expression of Humanized 7A4, 7A4D and 13F1 Antibodies

DNA encoding humanized 7A4, 7A4D and 13F1 antibody light chain and heavy chain was synthesized and cloned to the expression vector pcDNA3.1 (Invitrogen, CAT: #V-790). Freestyle 293 cells (200 mL at $10^6$/mL) were transfected with 100 µg of each of the humanized heavy and light chain expression plasmids and cultured for 6 days. The humanized antibody in the supernatant was then purified with Protein-G column (GE healthcare).

Example 10—Characterization of Humanized Anti-PD-1 Antibodies in Binding Activity and Specificity, and Ligand (PD-L1) Blockage Activity After generation and purification of humanized 13F1-hIgG1, 13F1-hIgG4, 7A4-IgG1 and 7A4-hIgG4 antibodies, the binding and specificity of the antibodies were determined based on ELISA-based binding and PD-1 blockage analyses, as well as FACS-based binding and PD-L1 blockage analyses. The methods used were similar to those described above in Examples 2 and 4.

In the ELISA-based binding assays, humanized 13F1 antibodies hu-13F1-hIgG1 and hu-13F1-hIgG4 exhibited similar binding to PD-1 compared to the chimeric antibody 13F1-chimeric (FIG. 6A, top panel); and humanized 7A4 antibodies hu-7A4-D265A-hIgG1 and 7A4-huIgG4 exhibited similar binding to PD-1 compared to the chimeric 7A4 antibodies (FIG. 6B, top panel). In contrast, the isotype control hIgG4 antibody did not exhibit PD-1 binding. The bottom panels of FIG. 6A and FIG. 6B show the EC50 for each of the antibodies tested, calculated from the ELISA binding data, and demonstrates that the humanized 13F1 and 7A4 antibodies exhibited PD-1 binding.

Similarly, in the FACS-based binding assays, humanized 13F1 antibodies hu-13F1-hIgG1 and hu-13F1-hIgG4 (FIG. 7A, top panel) and humanized 7A4 antibodies hu-7A4-D265A-hIgG1 and 7A4-huIgG4 (FIG. 7B, top panel) exhibited binding to PD-1. The EC50 calculated from the FACS binding data for humanized 13F1 and 7A4 antibodies are shown in FIG. 7A and FIG. 7B, respectively.

FIG. 8 shows the results of the ELISA-based ligand blocking assays for humanized 13F1 and humanized 7A4 antibodies. As shown in FIG. 8A and FIG. 8B, the humanized 13F1 and 7A4 antibodies, respectively, exhibited similar ligand blockage activity relative to the corresponding chimeric antibody. Quantification of the IC50 for each of the humanized and chimeric antibodies is shown in FIG. 8C.

Figure 9:
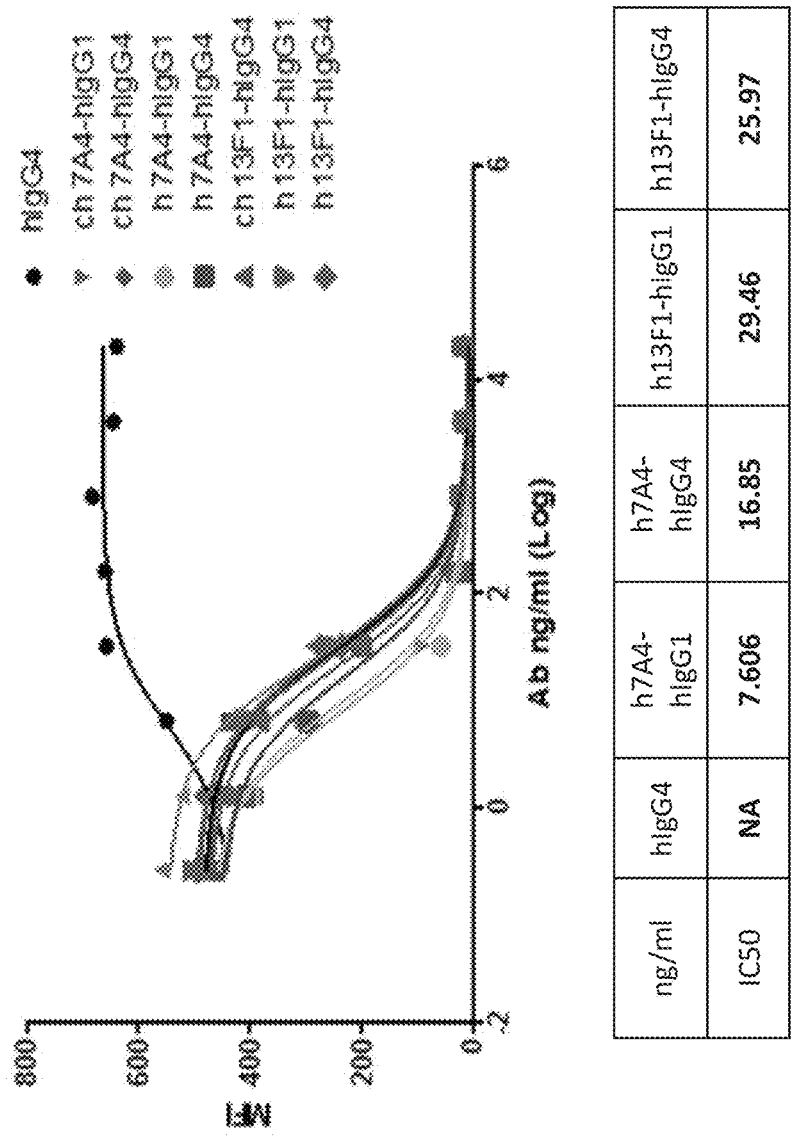
FIG. 9 shows the blockage of PD-L1 binding by humanized 13F1 and 7A4 antibodies as measured by FACS. The top panel of FIG. 9 shows the MFI over a range of antibody concentrations. The blockage IC50 for the humanized antibodies are shown in the bottom panel of FIG. 9.

FIG. 9 shows that each of the humanized 13F1 and humanized 7A4 antibodies blocked PD-L1 binding as measured by FACS-based ligand blockage assay. The bottom panel of FIG. 9 provides the IC50 for each of the humanized antibodies.

Figure 10:
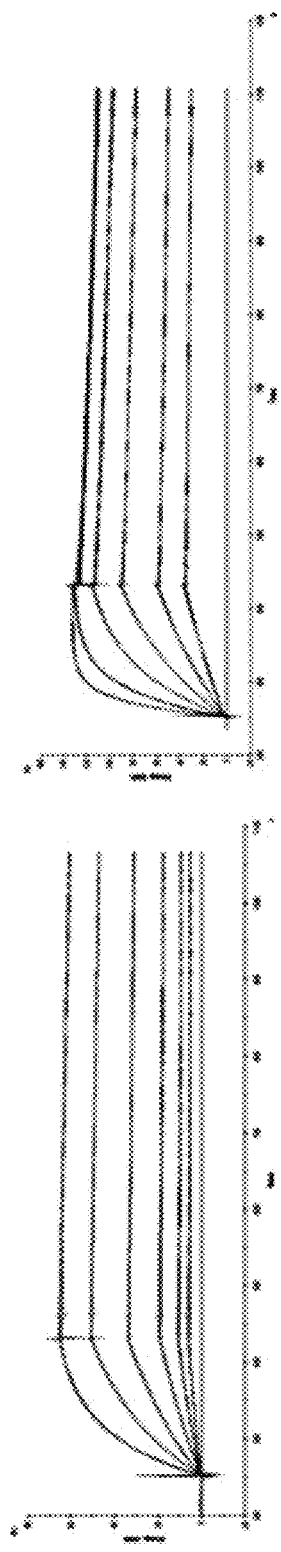
FIG. 10 shows the binding data for PD-1 humanized monoclonal antibodies h13F1 (top left panel) and h7A4 (top right panel), as measured by Biacore assay. The bottom panel provides the quantified binding data as measured by Biacore assay.
Figure 17:
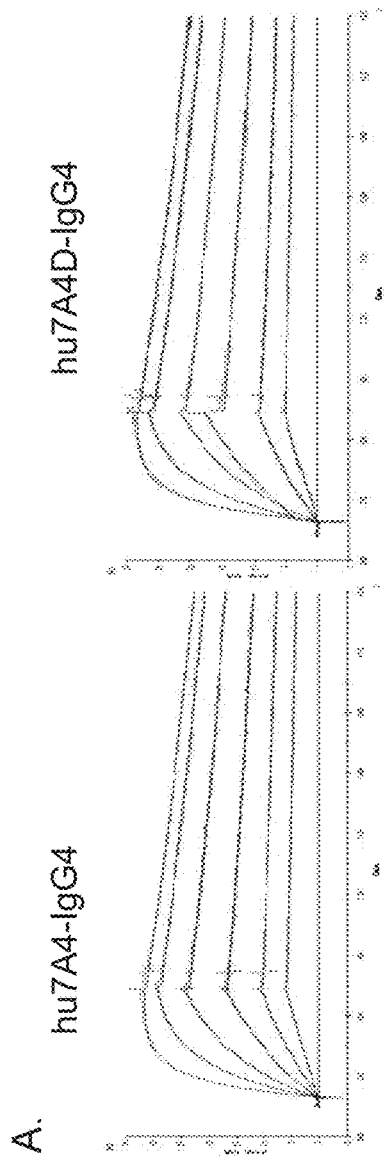
FIGS. 17A and 17B show the data of Biacore based binding (FIG. 17A) and FACS based blockage (FIG. 17B) for PD-1 humanized monoclonal antibodies h7A4 and h7A4D. For FIG. 17A, top left indicates h7A4 and top right indicates 7A4D, and the bottom panel of FIG. 17A provides the quantified binding data as measured by Biacore analysis.

Example 11—Biacore Kinetic Analysis of the Humanized 13F1, 7A4 and 7A4D Anti-PD-1 Antibodies To characterize the binding characteristics of the humanized antibodies, the binding kinetics between PD-1 and PD-1 antibodies were measured by Biacore3000 and recorded with a data collection rate of 1 Hz. The polyclonal rabbit anti-mouse IgG (GE, BR-1008-38) was diluted with 10 mM pH 5.0 sodium acetate and immobilized onto reference and experiment flow cells of a CM5 biosensor chip to around 15000 RU using an amine coupling kit (GE, BR10050). In the beginning of each cycle, diluted test antibody (1.5 µg/mL) was injected over experiment flow cell for 1 minute to be captured. PD-1 analyte series were prepared by diluting the stocks with running buffer to 100 nM followed by 2× serial dilution in the same buffer down to 0.78 nM. Analytes were injected in series over the reference and experiment flow cells for 3 minutes at a flow rate of 30 µL/minute. Then running buffer (PBS with 0.05% P20) was allowed to flow over for 10 minutes at a flow rate of 30 µL/minute. At the end of each cycle, the biosensor surface was regenerated with 3 minutes injection of 10 mM pH1.7 Glycine-HC1 buffer at a flow rate of 10 µL/minute. For each analyte sample injection (i.e. each cycle), binding responses obtained from the experimental biosensor surface were double referenced by subtracting simultaneously recorded responses from the reference surface followed by additional subtraction of responses from a single referenced running buffer sample. The association and dissociation rate constants (ka and kd) were determined simultaneously by fitting double-referenced sensorgrams of the entire titration series to Langmuir model (1:1) using Biaevaluation 4.0 software. The dissociation constant, KD, was calculated from the determined rate constants by the relation KD=kd/ka. As shown in FIGS. 10 and 17A, the humanized anti-PD-1 antibodies 13F1, 7A4, and 7A4D bound human PD-1 with high affinity. The Biocore binding curves are shown in FIGS. 10 and 17A, top panel, and the quantified binding data are summarized in FIGS. 10 and 17A, bottom panel. FIG. 17B indicates the blockage IC50 of PD-L1's binding to 293T-PD1 cells by 7A4D-hIgG4 antibody.

Example 12—Effect of Humanized Anti-PD-1 Antibodies on Cytokine Production in a Mixed Lymphocyte Reaction (MLR)

Figure 11:
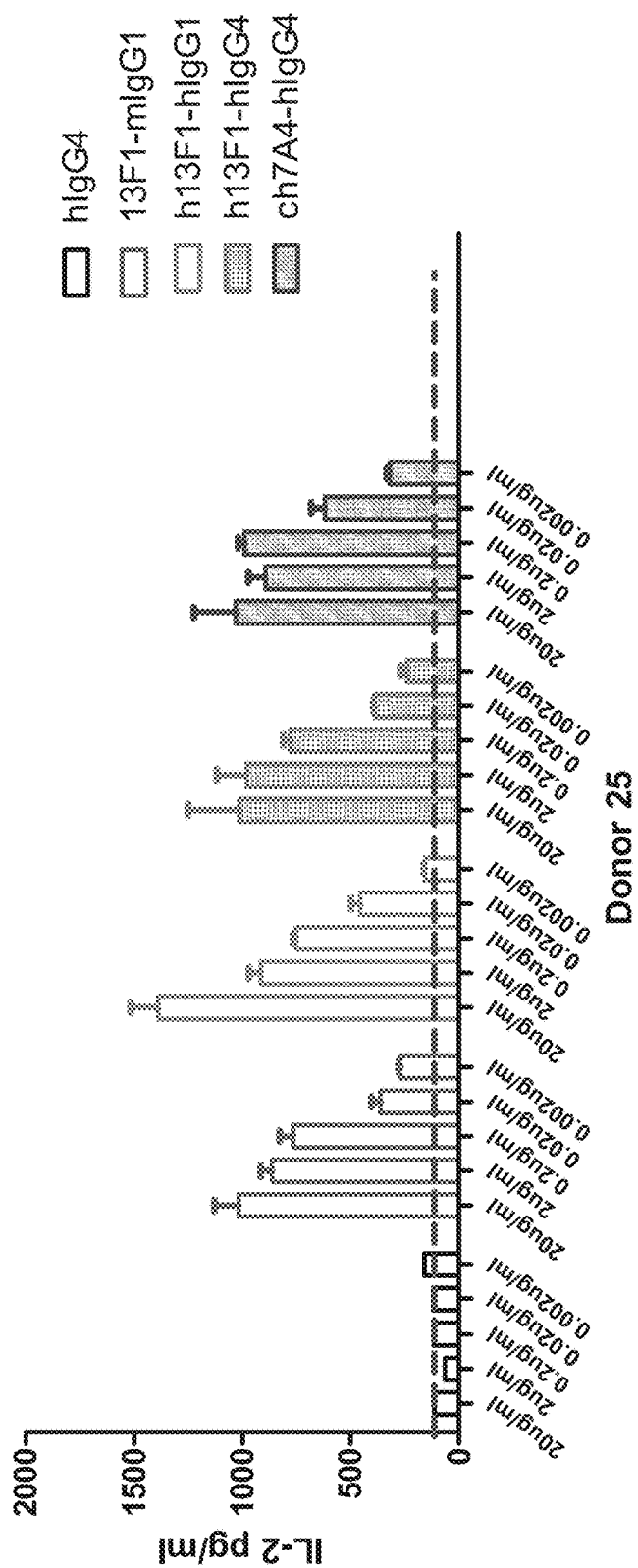
FIG. 11 is a graph showing IL-2 production (pg/mL) in an MLR reaction in the presence of control hIgG4, murine 13F1-mIgG1 (13F1-mIgG1), humanized 13F1-hIgG1, humanized 13F1-hIgG4, or chimeric 7A4-hIgG4 at the following concentrations: 20 µg/mL, 2 µg/mL, 0.2 µg/mL, 0.02 µg/mL, and 0.002 µg/mL.
Figure 12:
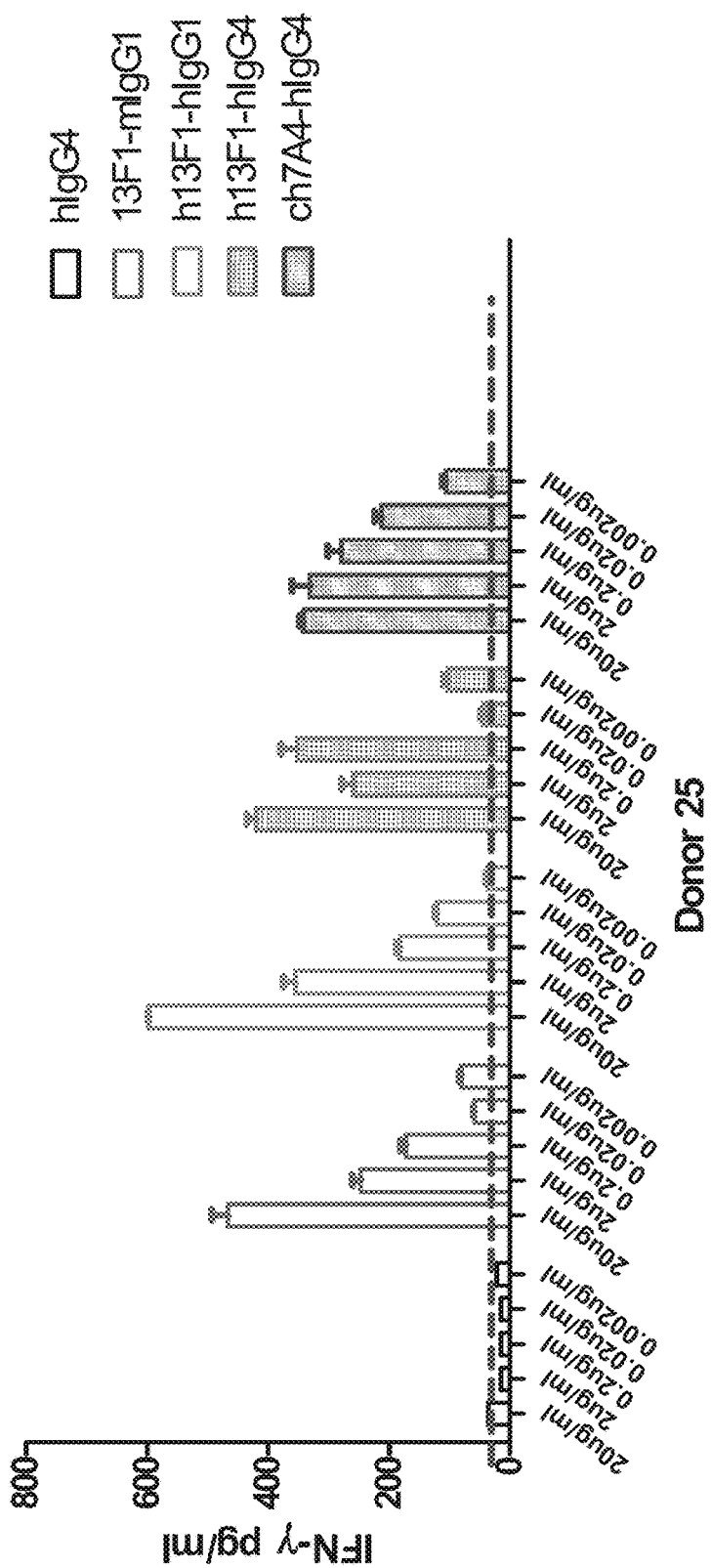
FIG. 12 is a graph showing IFN-γ production (pg/mL) in an MLR reaction in the presence of control hIgG4, murine 13F1-mIgG1 (13F1-mIgG1), humanized 13F1-hIgG1, humanized 13F1-hIgG4, or chimeric 7A4-hIgG4 at the following concentrations: 20 µg/mL, 2 µg/mL, 0.2 µg/mL, 0.02 µg/mL, and 0.002 µg/mL.
Figure 13:
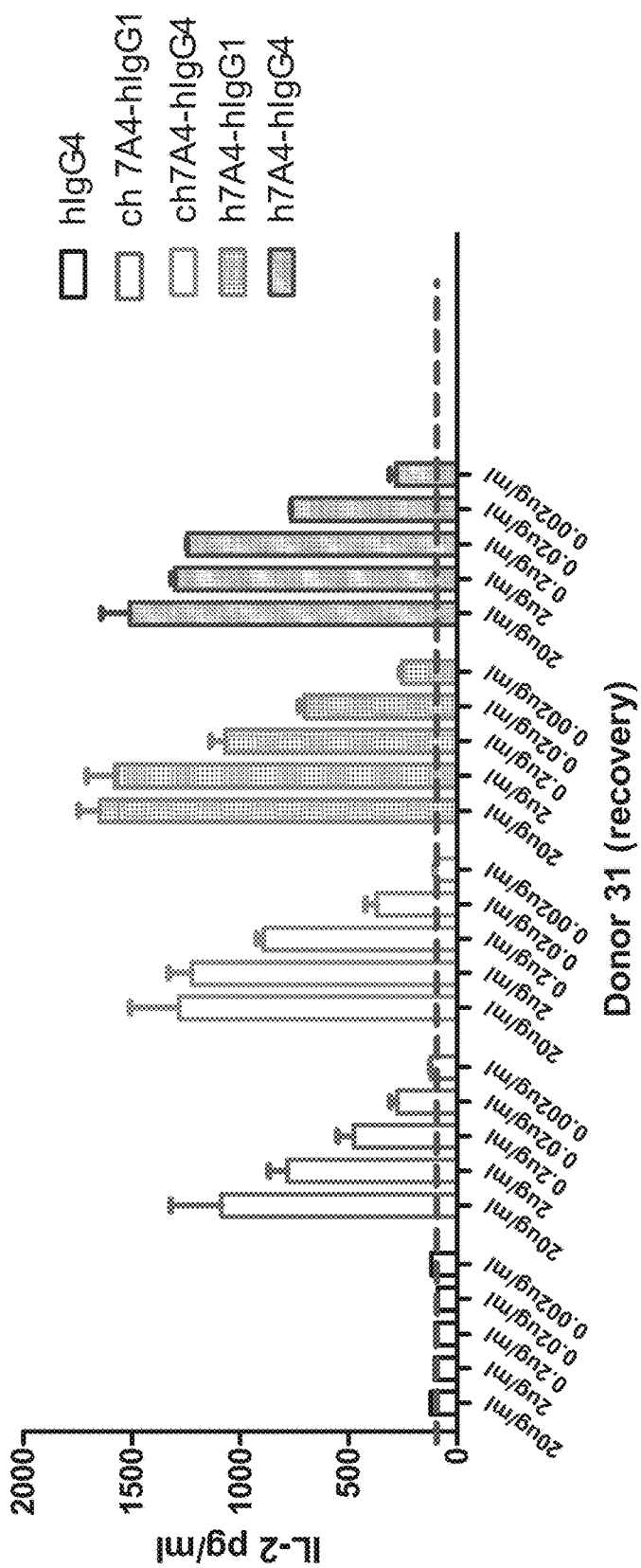
FIG. 13 is a graph showing IL-2 production (pg/mL) in an MLR reaction in the presence of control hIgG4, chimeric 7A4-hIgG1, chimeric 7A4-hIgG4, humanized 7A4-hIgG1, or humanized 7A4-hIgG4 at the following concentrations: 20 µg/mL, 2 µg/mL, 0.2 µg/mL, 0.02 µg/mL, and 0.002 µg/mL.
Figure 14:
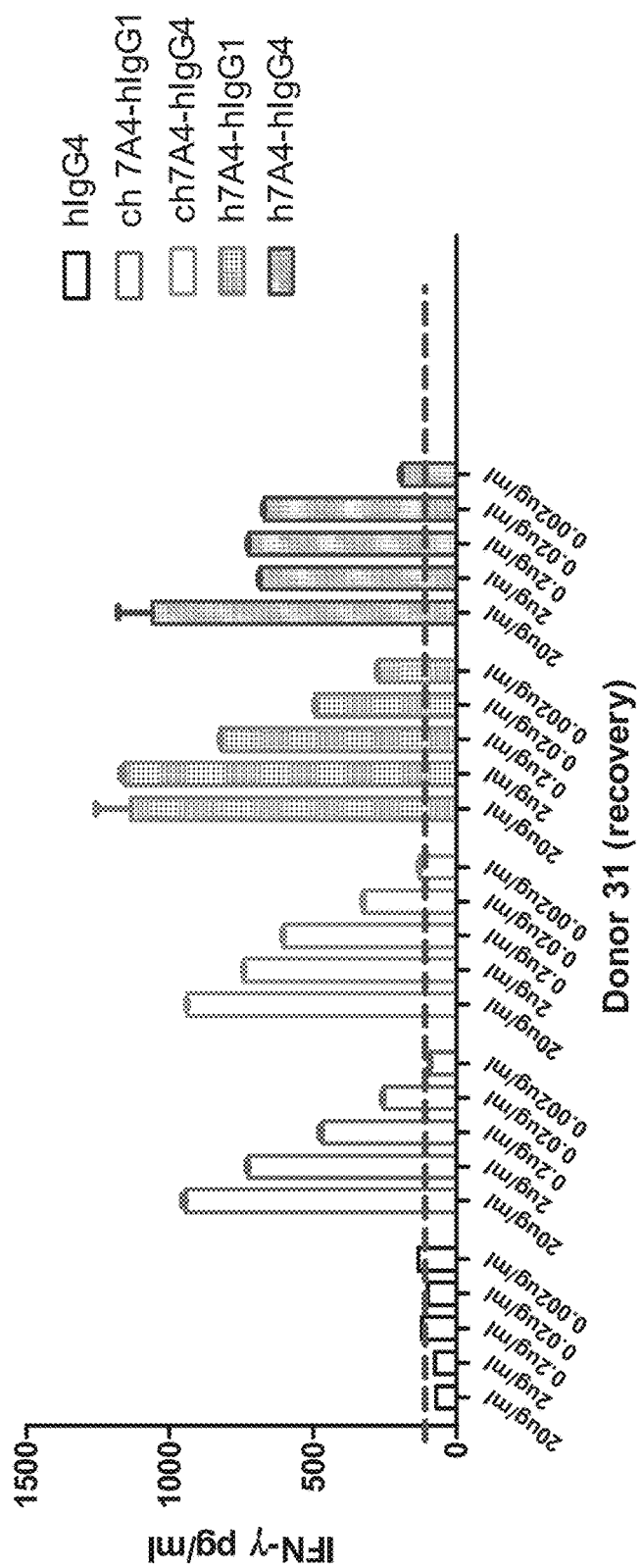
FIG. 14 is a graph showing IFN-γ production (pg/mL) in an MLR reaction in the presence of control hIgG4, chimeric 7A4-hIgG1, chimeric 7A4-hIgG4, humanized 7A4-hIgG1, or humanized 7A4-hIgG4 at the following concentrations: 20 µg/mL, 2 µg/mL, 0.2 µg/mL, 0.02 µg/mL, and 0.002 µg/mL.
Figure 18:
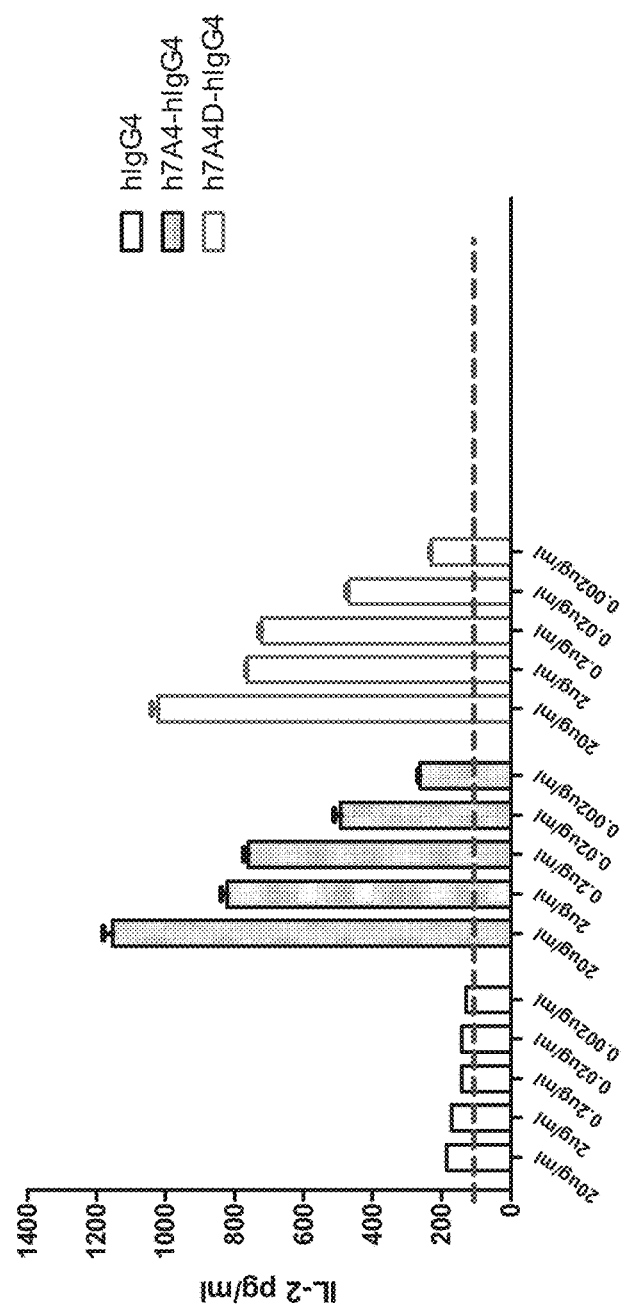
FIG. 18 is a graph showing IL-2 production (pg/mL) in an MLR reaction in the presence of control hIgG4, humanized 7A4-hIgG4, or humanized 7A4D-hIgG4 at the following concentrations: 20 µg/mL, 2 µg/mL, 0.2 µg/mL, 0.02 µg/mL, and 0.002 µg/mL.
Figure 19:
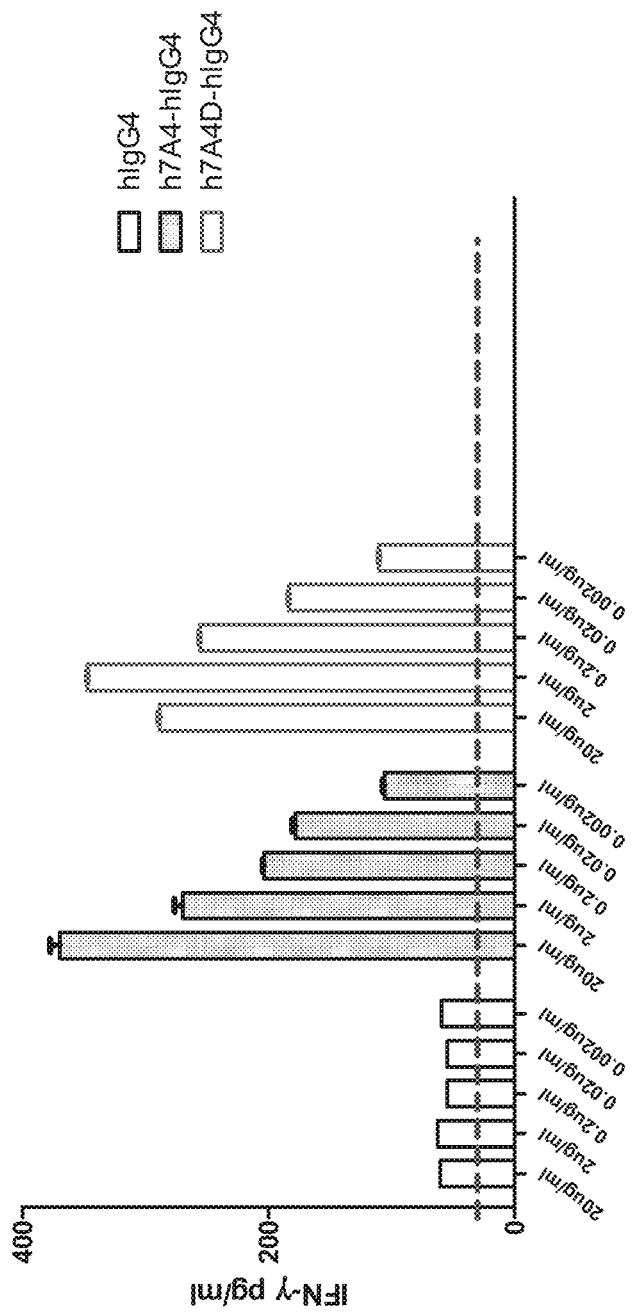
FIG. 19 is a graph showing IFN-γ production (pg/mL) in an MLR reaction in the presence of control hIgG4, humanized 7A4-hIgG4, or humanized 7A4D-hIgG4 at the following concentrations: 20 µg/mL, 2 µg/mL, 0.2 µg/mL, 0.02 µg/mL, and 0.002 µg/mL.

Mixed Lymphocyte Reactions (MLR) were employed to demonstrate the ability of the humanized antibodies to block the PD-1 pathway in lymphocyte effector cells. T cells in the assay were tested for IFNγ and IL-2 secretion in the presence or absence of anti-PD-1 antibodies. Human CD4$^+$ T-cells were purified from human PBMC using a CD4 negative selection isolation kit (Mitenyi Biotech, cat#130-091-155). Immature dendritic cells (DC) were derived from monocytes isolated from human PBMC using the Mo-DC Generation Toolbox (Miltenyi, cat#130-093-568). The cells were cultured with Mo-DC Differentiation Medium for 7 days, and were then induced to be mature DC with Mo-Dc Maturation medium for 2 days. To set up the MLR, $10^5$ purified T-cells and $10^4$ allogeneic mature DC cells in a total volume of 200 μl were added to each well. The testing antibody was assayed at a range of concentrations from 20 μg/ml to 0.002 μg/ml. Either no antibody or an isotype control antibody (hIgG4) was used as a negative control. The cells were cultured for 5 days at 37° C. On day $6^{th}$, the levels of IFN-γ and IL-2 in the culture medium were measured using the IL-2 ELISA kit (eBioscience) and hIFN-γ ELISA kit (R&D, cat#DY285). For humanized 13F1 antibodies, the results are shown in FIG. 11 (IL-2 production) and FIG. 12 (IFNγ production). Each of the humanized 13F1 antibodies promoted IL-2 and IFNγ production in a concentration dependent manner. Similarly, humanized 7A4 and 7A4D antibodies promoted IL-2 (FIGS. 13 and 18) and IFNγ (FIGS. 14 and 19) production in a concentration dependent manner. Cultures containing the isotype control antibody did not show increase in IFN-γ and IL-2 secretion. Thus, the results of the study showed that the humanized PD-1 antibodies block the PD-1 pathway, stimulating T cell immune responses.

Figure 15:
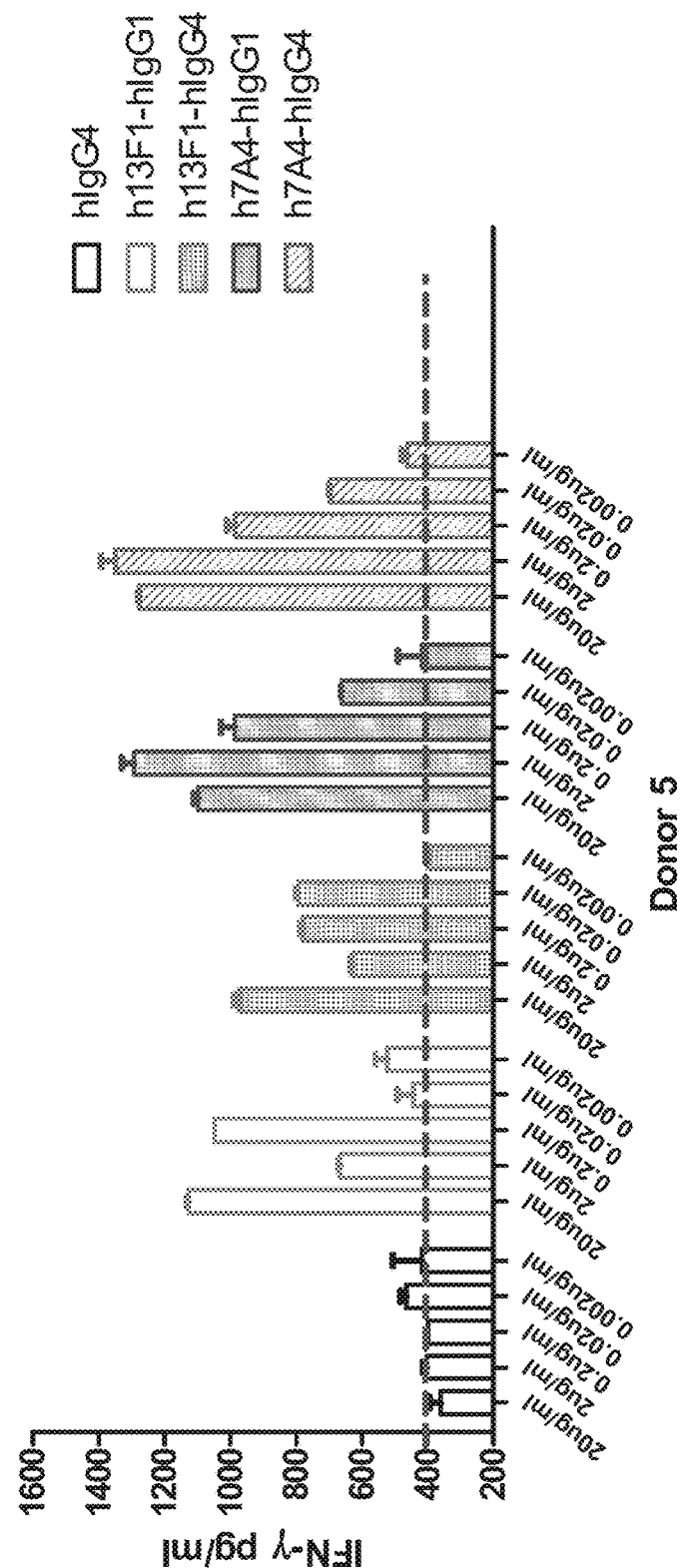
FIG. 15 shows the effect of humanized anti-PD-1 antibodies on memory T cell responses recalled by tetanus toxin, as measured by IFN-γ production (pg/mL). Negative control hIgG4, humanized 13F1-hIgG1, humanized 13F1-hIgG4, humanized 7A4-hIgG1, and humanized 7A4-hIgG4 antibodies were tested at the following concentrations: 20 µg/mL, 2 µg/mL, 0.2 µg/mL, 0.02 µg/mL, and 0.002 µg/mL.

Example 13—Human Recall T Cell Response to Tetanus Toxoid Challenge is Enhanced by Humanized Anti-PD-1 Antibody To investigate whether the antigen-specific T cell receptor triggering was modulated by blocking PD-1/PD-L1 pathway with anti-PD-1 antibodies, the human T-cell recall assay was employed using tetanus toxoid (TT) antigen to stimulate pre-existing memory T cells in the blood of healthy TT immunized donors. To this end, fresh PBMC recently collected (samples collected within less than 1 year) from TT immunized donors were plated into 96-well round bottom plates (costar, cat#3799) at $4\times10^5$ cells/well using RPMI1640 (Invitrogen, cat# A10491-01) supplemented with 80 U/ml penicillin, 80 g/ml streptomycin and 30% autologous serum. Humanized 13F1 or 7A4 antibodies were added at various concentrations, and stimulated with 0.1 ug/ml SEB and 1 ug/ml TT (Astarte Biologies). After co-culture for 7 days at 37° C., 5% $CO_2$, the supernatant was harvested and the concentration of IFN-γ was measured. The results of the study are shown in FIG. 15, and demonstrate that, compared to TT antigen alone, PD-L1 blockage with anti-PD-1 antibodies resulted in enhanced IFN-γ secretion by memory T cells.

Figure 16:
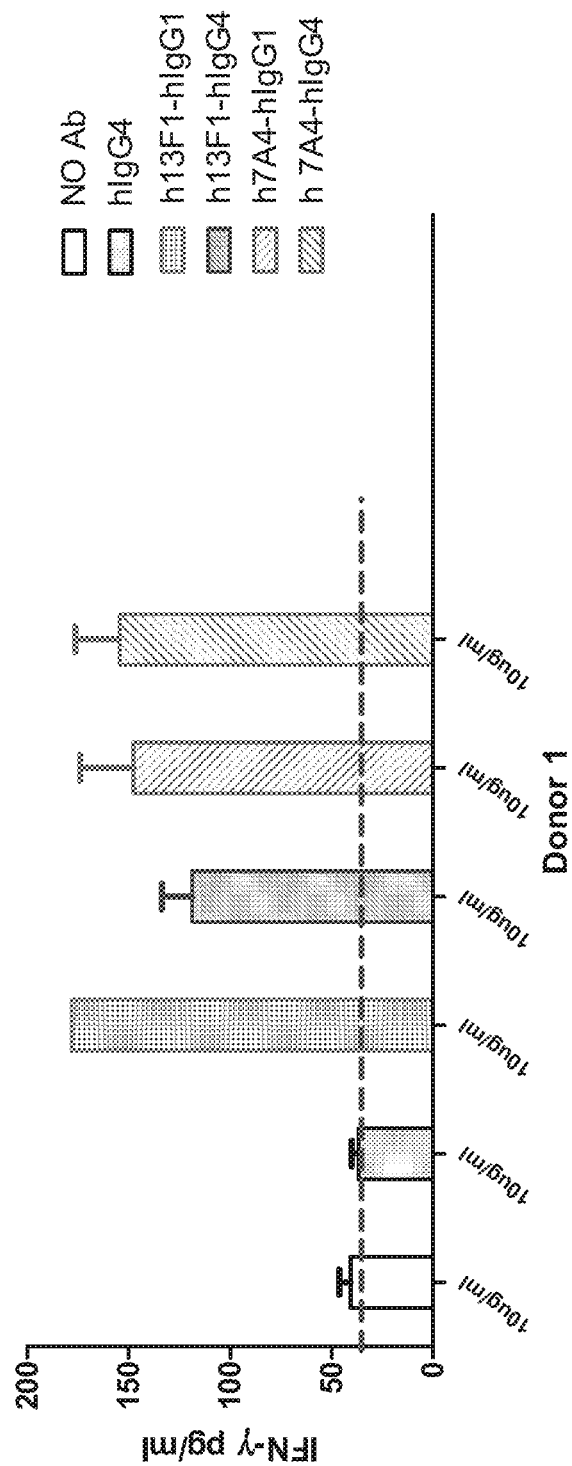
FIG. 16 shows IFN-γ production (pg/mL) from T cells in response to costimulation with autologous DCs and anti-CD3 antibody, in the presence of 10 µg/ml of humanized anti-PD-1 antibodies (h13F1-hIgG1, h13F1-hIgG4, h7A4-hIgG1, or h7A4-hIgG4), isotype control (hIgG4) antibody, or no antibody.

Example 14—Effect of Humanized Anti-PD-1 Antibody on Autologous T Cell Activation In this example, the effect of blocking PD-/PD-L1 pathway by humanized anti-PD-1 antibody on T cell activation was examined. Purified human CD4+ T cells (Mitenyi Biotech, cat#130-091-155) were activated with 1 μg/ml soluble anti-CD3 antibody (R&D, cat#MAB100) in the presence of autologous monocyte-derived dendritic cells (DCs). After three days of activation in the presence or absence of titrated anti-PD-1 antibody, culture medium was harvested and the concentration of IFNγ was measured with ELISA. The results are shown in FIG. 16 and indicate that PD-L1 blockage by anti-PD-1 antibody enhanced IFN-γ secretion by T cells.

The invention claimed is:

1. An isolated antibody or fragment thereof that binds to PD-1, wherein the antibody or fragment thereof comprises
(i) a light chain CDR1, CDR2, and CDR3 sequence comprising SEQ ID NO: 34, 35, and 36, respectively, and a heavy chain CDR1, CDR2, and CDR3 sequence comprising SEQ ID NO: 29, 30, and 31, respectively;
(ii) a light chain CDR1, CDR2, and CDR3 sequence comprising SEQ ID NO: 55, 56, and 57, respectively, and a heavy chain CDR1, CDR2, and CDR3 sequence comprising SEQ ID NO: 50, 51, and 52, respectively;
(iii) a light chain CDR1, CDR2, and CDR3 sequence comprising SEQ ID NO: 65, 66, and 67, respectively, and a heavy chain CDR1, CDR2, and CDR3 sequence comprising SEQ ID NO: 60, 61, and 62, respectively;
(iv) a light chain CDR1, CDR2, and CDR3 sequence comprising SEQ ID NO: 105, 106, and 107, respectively, and a heavy chain CDR1, CDR2, and CDR3 sequence comprising SEQ ID NO: 100, 101, and 102, respectively; or
(v) a light chain CDR1, CDR2, and CDR3 sequence comprising SEQ ID NO: 115, 116, and 117, respectively, and a heavy chain CDR1, CDR2, and CDR3 sequence comprising SEQ ID NO: 110, 111, and 112, respectively.

2. The antibody or fragment of claim 1, wherein the antibody or fragment thereof comprises a light chain CDR1, CDR2, and CDR3 comprising an amino acid sequence according to SEQ ID NOs: 34, 35, and 36, respectively; and a heavy chain CDR1, CDR2, and CDR3 comprising an amino acid sequence according to SEQ ID NOs: 29, 30, and 31, respectively.

3. The antibody or fragment of claim 1, wherein the antibody or fragment thereof comprises a light chain CDR1, CDR2, and CDR3 comprising an amino acid sequence according to SEQ ID NOs: 55, 56, and 57, respectively; and a heavy chain CDR1, CDR2, and CDR3 comprising an amino acid sequence according to SEQ ID NOs: 50, 51, and 52, respectively.

4. The antibody or fragment of claim 1, wherein the antibody or fragment thereof comprises a light chain CDR1, CDR2, and CDR3 comprising an amino acid sequence according to SEQ ID NOs: 65, 66, and 67, respectively; and a heavy chain CDR1, CDR2, and CDR3 comprising an amino acid sequence according to SEQ ID NOs: 60, 61, and 62, respectively.

5. The antibody or fragment of claim 1, wherein the antibody or fragment thereof comprises a light chain CDR1, CDR2, and CDR3 comprising an amino acid sequence according to SEQ ID NOs: 105, 106, and 107, respectively; and a heavy chain CDR1, CDR2, and CDR3 comprising an amino acid sequence according to SEQ ID NOs: 100, 101, and 102, respectively.

6. The antibody or fragment of claim 1, wherein the antibody or fragment thereof comprises a light chain CDR1, CDR2, and CDR3 comprising an amino acid sequence according to SEQ ID NOs: 115, 116, and 117, respectively; and a heavy chain CDR1, CDR2, and CDR3 comprising an amino acid sequence according to SEQ ID NOs: 110, 111, and 112, respectively.

7. The isolated antibody or fragment thereof of claim 1, wherein the antibody or fragment thereof is chimeric or humanized.

8. The isolated antibody or fragment of claim 1, wherein the antibody or fragment thereof comprises:
(i) a light chain variable region comprising SEQ ID NO: 33 and a heavy chain variable region comprising SEQ ID NO: 28;
(ii) a light chain variable region comprising SEQ ID NO: 54 and a heavy chain variable region comprising SEQ ID NO: 49;
(iii) a light chain variable region comprising SEQ ID NO: 64 and a heavy chain variable region comprising SEQ ID NO: 59;
(iv) a light chain variable region comprising SEQ ID NO: 104 and a heavy chain variable region comprising SEQ ID NO: 99;
(v) a light chain variable region comprising SEQ ID NO: 114 and a heavy chain variable region comprising SEQ ID NO: 109;
(vi) a light chain variable region comprising SEQ ID NO: 143 and a heavy chain variable region comprising SEQ ID NO: 141; or
(vii) a light chain variable region comprising SEQ ID NO: 152 and a heavy chain variable region comprising SEQ ID NO: 131.

9. The isolated antibody or fragment of claim 1, wherein the antibody or fragment thereof comprises a light chain variable region according to SEQ ID NO: 133 or 152 and a heavy chain variable region according to SEQ ID NO: 131.

10. The isolated antibody or fragment of claim 1, wherein the antibody or fragment thereof comprises a light chain variable region according to SEQ ID NO: 143 and a heavy chain variable region according to SEQ ID NO: 141.

11. The isolated antibody or fragment thereof of claim 1, wherein the antibody or fragment thereof is selected from the group consisting of a monoclonal antibody, an scFv, a Fab fragment, an Fab' fragment, and an F(ab)' fragment.

12. An antibody or fragment thereof according to claim 1, wherein the antibody or fragment thereof is linked or conjugated to a therapeutic agent.

13. The antibody or fragment thereof according to claim 12, wherein the therapeutic agent is a cytotoxic drug, a radioactive isotope, an immunomodulator, or an antibody.

14. The isolated antibody or fragment thereof according to claim 1, wherein the antibody or fragment thereof has an affinity for PD-1 of about 1 nM to about 0.01 nM.

15. The isolated antibody or fragment thereof according to claim 14, wherein the antibody or fragment thereof as an affinity for PD-1 of about 1 nM or less.

16. The isolated antibody or fragment thereof according to claim 14, wherein the antibody or fragment thereof as an affinity for PD-1 of about 0.1 nM or less.

17. The isolated antibody or fragment thereof according to claim 1, wherein the antibody has a binding EC50 of about 5 ng/mL to about 1000 ng/mL.

18. The isolated antibody or fragment thereof of claim 1, wherein the antibody blocks binding of PD-1 to PD-L1.

19. An isolated antibody or fragment thereof of claim 18, wherein the antibody or fragment thereof blocks the binding of PD-1 to PD-L1 or PD-L2 at an IC50 of about 5 ng/mL to about 1000 ng/mL.

20. The isolated antibody or fragment thereof of claim 1, wherein the antibody or fragment increases T cell activation as measured by inflammatory cytokine production.

21. The isolated antibody or fragment thereof according to claim 20, wherein the antibody or fragment thereof increases T cell production of IL-2 and IFNγ.

22. A composition comprising the antibody or fragment thereof according to claim 1 and a pharmaceutically acceptable carrier.

23. An isolated polynucleotide encoding the antibody or fragment thereof according to claim 1.

24. An expression vector comprising the isolated polynucleotide according to claim 23.

25. A host cell comprising the expression vector according to claim 24.

26. A method for increasing T cell activation, the method comprising contacting T cells with an antibody or fragment thereof according to claim 1.

\* \* \* \* \*

SEQUENCE LISTING

```
<160> NUMBER OF SEQ ID NOS: 153

<210> SEQ ID NO 1
<211> LENGTH: 450
<212> TYPE: DNA
<213> ORGANISM: Homo sapiens

<400> SEQUENCE: 1
ccaggatggt tcttagactc cccagacagg ccctggaacc cccccacctt ctccccagcc      60
ctgctcgtgg tgaccgaagg ggacaacgcc accttcacct gcagcttctc caacacatcg     120
gagagcttcg tgctaaactg gtaccgcatg agccccagca accagacgga caagctggcc     180
gccttccccg aggaccgcag ccagcccggc caggactgcc gcttccgtgt cacacaactg     240
cccaacgggc gtgacttcca catgagcgtg gtcagggccc ggcgcaatga cagcggcacc     300
tacctctgtg gggccatctc cctggccccc aaggcgcaga tcaaagagag cctgcgggca     360
gagctcaggg tgacagagag aagggcagaa gtgcccacag cccaccccag cccctcaccc     420
```

```
aggccagccg gccagttcca aaccctggtg                                       450
```

<210> SEQ ID NO 2
<211> LENGTH: 150
<212> TYPE: PRT
<213> ORGANISM: Homo sapiens

<400> SEQUENCE: 2

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150
```

<210> SEQ ID NO 3
<211> LENGTH: 1134
<212> TYPE: DNA
<213> ORGANISM: Homo sapiens

<400> SEQUENCE: 3

```
ccaggatggt tcttagactc cccagacagg ccctggaacc cccccaccct ctccccagcc    60
ctgctcgtgg tgaccgaagg ggacaacgcc accttcacct gcagcttctc caacacatcg   120
gagagcttcg tgctaaactg gtaccgcatg agccccagca accagacgga caagctggcc   180
gccttccccg aggaccgcag ccagcccggc caggactgcc gcttccgtgt cacacaactg   240
cccaacgggc gtgacttcca catgagcgtg gtcagggccc ggcgcaatga cagcggcacc   300
tacctctgtg gggccatctc cctggccccc aaggcgcaga tcaaagagag cctgcgggca   360
gagctcaggg tgacagagag aagggcagaa gtgcccacag cccaccccag ccctcaccc    420
aggccagccg gccagttcca aaccctggtg gtaccagat ctagaggctg caaaccctgt    480
atctgcacag tgcccgaggt gagctccgtt ttcatctttc cccccaagcc caaggacgtg    540
ctgaccatca cactcacacc caaggtcacc tgcgtggtcg tggacatctc caaggacgac    600
cccgaagtcc agttcagctg gttcgtggac gacgtggagg tgcacaccgc tcagacccaa    660
cccagagagg agcagtttaa ctccaccttc aggtccgtgt ccgagctccc catcatgcac    720
caggactggc tgaatggcaa ggagttcaag tgcagggtga actccgctgc tttccccgcc    780
cccattgaga agaccatctc caagaccaag ggaaggccca aggccccca ggtgtacacc     840
attccccctc ccaaggagca gatggccaag gacaaggtgt ccctgacctg tatgatcacc    900
```

```
gacttctttc ccgaggacat caccgtcgaa tggcagtgga acggccagcc cgccgagaac    960
tataagaaca cccaacccat catggacacc gacggcagct acttcgtgta tagcaagctc   1020
aacgtgcaga agagcaactg ggaagccgga aataccttca cctgctccgt cctgcacgag   1080
ggcctgcaca accaccatac cgaaaagagc ctgagccaca gccccggaaa gtaa         1134
```

<210> SEQ ID NO 4
<211> LENGTH: 377
<212> TYPE: PRT
<213> ORGANISM: Homo sapiens

<400> SEQUENCE: 4

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Thr Arg Ser Arg Gly Cys Lys Pro Cys
145                 150                 155                 160

Ile Cys Thr Val Pro Glu Val Ser Ser Val Phe Ile Phe Pro Pro Lys
                165                 170                 175

Pro Lys Asp Val Leu Thr Ile Thr Leu Thr Pro Lys Val Thr Cys Val
            180                 185                 190

Val Val Asp Ile Ser Lys Asp Asp Pro Glu Val Gln Phe Ser Trp Phe
        195                 200                 205

Val Asp Asp Val Glu Val His Thr Ala Gln Thr Gln Pro Arg Glu Glu
    210                 215                 220

Gln Phe Asn Ser Thr Phe Arg Ser Val Ser Glu Leu Pro Ile Met His
225                 230                 235                 240

Gln Asp Trp Leu Asn Gly Lys Glu Phe Lys Cys Arg Val Asn Ser Ala
                245                 250                 255

Ala Phe Pro Ala Pro Ile Glu Lys Thr Ile Ser Lys Thr Lys Gly Arg
            260                 265                 270

Pro Lys Ala Pro Gln Val Tyr Thr Ile Pro Pro Lys Glu Gln Met
        275                 280                 285

Ala Lys Asp Lys Val Ser Leu Thr Cys Met Ile Thr Asp Phe Phe Pro
    290                 295                 300

Glu Asp Ile Thr Val Glu Trp Gln Trp Asn Gly Gln Pro Ala Glu Asn
305                 310                 315                 320

Tyr Lys Asn Thr Gln Pro Ile Met Asp Thr Asp Gly Ser Tyr Phe Val
                325                 330                 335
```

```
Tyr Ser Lys Leu Asn Val Gln Lys Ser Asn Trp Glu Ala Gly Asn Thr
            340                 345                 350

Phe Thr Cys Ser Val Leu His Glu Gly Leu His Asn His His Thr Glu
            355                 360                 365

Lys Ser Leu Ser His Ser Pro Gly Lys
            370                 375

<210> SEQ ID NO 5
<211> LENGTH: 1164
<212> TYPE: DNA
<213> ORGANISM: Homo sapiens

<400> SEQUENCE: 5
ccaggatggt tcttagactc cccagacagg ccctggaacc cccccacctt ctccccagcc      60
ctgctcgtgg tgaccgaagg ggacaacgcc accttcacct gcagcttctc caacacatcg     120
gagagcttcg tgctaaactg gtaccgcatg agccccagca accagacgga caagctggcc     180
gccttccccg aggaccgcag ccagcccggc caggactgcc gcttccgtgt cacacaactg     240
cccaacgggc gtgacttcca catgagcgtg gtcagggccc ggcgcaatga cagcggcacc     300
tacctctgtg gggccatctc cctggccccc aaggcgcaga tcaaagagag cctgcgggca     360
gagctcaggg tgacagagag aagggcagaa gtgcccacag cccaccccag cccctcaccc     420
aggccagccg ccagttccaa accctggtg ggtaccagat ctagagagcc caaatcttct     480
gacaaaactc acacatgccc accgtgccca gcacctgaat tcgaggtgca ccgtcagtc     540 ttcctcttcc ccccaaaacc caaggacacc ctcatgatct cccggactcc tgaggtcaca     600
tgcgtggtgg tggacgtaag ccacgaagac cctgaggtca agttcaactg gtacgtggac     660
ggcgtggagg tgcataatgc caagacaaag ccgcgggagg agcagtacaa cagcacgtac     720
cgtgtggtca gcgtcctcac cgtcctgcac caggactggc tgaatggcaa ggagtacaag     780
tgcaaggtct ccaacaaagc cctcccaacc ccatcgaga aaaccatctc caaagccaaa      840
gggcagcccc gagaaccaca ggtgtacacc ctgcccccat cccgggatga gctgaccaag     900
aaccaggtca gcctgacctg cctggtcaaa ggcttctatc caagcgacat cgccgtggag     960
tgggagagca atgggcagcc ggagaacaac tacaagacca cgcctcccgt gctggactcc    1020
gacggctcct tcttcctcta cagcaagctc accgtggaca agagcaggtg gcagcagggg    1080
aacgtcttct catgctccgt gatgcatgag gctctgcaca accactacac gcagaagagc    1140
ctctccctgt ctccgggtaa atga                                            1164

<210> SEQ ID NO 6
<211> LENGTH: 387
<212> TYPE: PRT
<213> ORGANISM: Homo sapiens

<400> SEQUENCE: 6

Pro Gly Trp Phe Leu Asp Ser Pro Asp Arg Pro Trp Asn Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80
```

```
Pro Asn Gly Arg Asp Phe His Met Ser Val Val Arg Ala Arg Arg Asn
                85                  90                  95
Asp Ser Gly Thr Tyr Leu Cys Gly Ala Ile Ser Leu Ala Pro Lys Ala
            100                 105                 110
Gln Ile Lys Glu Ser Leu Arg Ala Glu Leu Arg Val Thr Glu Arg Arg
        115                 120                 125
Ala Glu Val Pro Thr Ala His Pro Ser Pro Ser Pro Arg Pro Ala Gly
    130                 135                 140
Gln Phe Gln Thr Leu Val Gly Thr Arg Ser Arg Glu Pro Lys Ser Ser
145                 150                 155                 160
Asp Lys Thr His Thr Cys Pro Pro Cys Pro Ala Pro Glu Phe Glu Gly
                165                 170                 175
Ala Pro Ser Val Phe Leu Phe Pro Pro Lys Pro Lys Asp Thr Leu Met
            180                 185                 190
Ile Ser Arg Thr Pro Glu Val Thr Cys Val Val Val Asp Val Ser His
        195                 200                 205
Glu Asp Pro Glu Val Lys Phe Asn Trp Tyr Val Asp Gly Val Glu Val
    210                 215                 220
His Asn Ala Lys Thr Lys Pro Arg Glu Glu Gln Tyr Asn Ser Thr Tyr
225                 230                 235                 240
Arg Val Val Ser Val Leu Thr Val Leu His Gln Asp Trp Leu Asn Gly
                245                 250                 255
Lys Glu Tyr Lys Cys Lys Val Ser Asn Lys Ala Leu Pro Thr Pro Ile
            260                 265                 270
Glu Lys Thr Ile Ser Lys Ala Lys Gly Gln Pro Arg Glu Pro Gln Val
        275                 280                 285
Tyr Thr Leu Pro Pro Ser Arg Asp Glu Leu Thr Lys Asn Gln Val Ser
    290                 295                 300
Leu Thr Cys Leu Val Lys Gly Phe Tyr Pro Ser Asp Ile Ala Val Glu
305                 310                 315                 320
Trp Glu Ser Asn Gly Gln Pro Glu Asn Asn Tyr Lys Thr Thr Pro Pro
                325                 330                 335
Val Leu Asp Ser Asp Gly Ser Phe Phe Leu Tyr Ser Lys Leu Thr Val
            340                 345                 350
Asp Lys Ser Arg Trp Gln Gln Gly Asn Val Phe Ser Cys Ser Val Met
        355                 360                 365
His Glu Ala Leu His Asn His Tyr Thr Gln Lys Ser Leu Ser Leu Ser
    370                 375                 380
Pro Gly Lys
385

<210> SEQ ID NO 7
<211> LENGTH: 1128
<212> TYPE: DNA
<213> ORGANISM: Cynomolgous sp.

<400> SEQUENCE: 7
ccaggatggt tcttagaatc cccggacagg ccctggaacc ccccaccctt ctccccagcc      60
ctgctcctgg tgaccgaagg agacaacgcc accttcacct gcagcttctc caacgcctcg     120
gagagcttcg tgctgaactg gtaccgcatg agccccagca accagacgga caagctggcc     180
gccttccccg aggaccgcag ccagcccggc caggactgcc gcttccgtgt cacacaactg     240
cccaacgggc gtgacttcca catgagcgtg gtcagggccc ggcgcaatga cagcggcacc     300
```

```
tacctctgtg gggccatctc cctggccccc aaggcgcaga tcaaagagag cctgcgggca   360
gagctcaggg tgacagagag aagggcagaa gtgcccacag cccacccag ccctcaccc    420
aggccagctg ccagttcca agccggtacc agatctagag gctgcaaacc ctgtatctgc   480
acagtgcccg aggtgagctc cgtgttcatc tttccccca agcccaagga cgtgctgacc   540
atcacactca cacccaaggt cacctgcgtg gtcgtggaca tctccaagga cgaccccgaa   600
gtccagttca gctggttcgt ggacgacgtg gaggtgcaca ccgctcagac ccaacccaga   660
gaggagcagt ttaactccac cttcaggtcc gtgtccgagc tccccatcat gcaccaggac   720
tggctgaatg gcaaggagtt caagtgcagg gtgaactccg ctgctttccc cgccccatt   780
gagaagacca tctccaagac caagggaagg cccaaggccc ccaggtgta caccattccc   840
cctcccaagg agcagatggc caaggacaag gtgtccctga cctgtatgat caccgacttc   900
tttcccgagg acatcaccgt cgaatggcag tggaacggcc agcccgccga aactataag   960
aacacccaac ccatcatgga caccgacggc agctacttcg tgtatagcaa gctcaacgtg  1020
cagaagagca actgggaagc cggaaatacc ttcacctgct ccgtcctgca cgagggcctg  1080
cacaaccacc ataccgaaaa gagcctgagc acagccccg gaaagtaa              1128
```

<210> SEQ ID NO 8
<211> LENGTH: 375
<212> TYPE: PRT
<213> ORGANISM: Cynomolgous sp.

<400> SEQUENCE: 8

```
Pro Gly Trp Phe Leu Glu Ser Pro Asp Arg Pro Trp Asn Pro Pro Thr
1               5                   10                  15

Phe Ser Pro Ala Leu Leu Val Thr Glu Gly Asp Asn Ala Thr Phe
            20                  25                  30

Thr Cys Ser Phe Ser Asn Ala Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Ala Gly Thr Arg Ser Arg Gly Cys Lys Pro Cys Ile Cys
145                 150                 155                 160

Thr Val Pro Glu Val Ser Ser Val Phe Ile Phe Pro Pro Lys Pro Lys
                165                 170                 175

Asp Val Leu Thr Ile Thr Leu Thr Pro Lys Val Thr Cys Val Val Val
            180                 185                 190

Asp Ile Ser Lys Asp Asp Pro Glu Val Gln Phe Ser Trp Phe Val Asp
        195                 200                 205

Asp Val Glu Val His Thr Ala Gln Thr Gln Pro Arg Glu Glu Gln Phe
    210                 215                 220

Asn Ser Thr Phe Arg Ser Val Ser Glu Leu Pro Ile Met His Gln Asp
```

```
                225                 230                 235                 240
Trp Leu Asn Gly Lys Glu Phe Lys Cys Arg Val Asn Ser Ala Ala Phe
                    245                 250                 255

Pro Ala Pro Ile Glu Lys Thr Ile Ser Lys Thr Lys Gly Arg Pro Lys
                260                 265                 270

Ala Pro Gln Val Tyr Thr Ile Pro Pro Lys Glu Gln Met Ala Lys
            275                 280                 285

Asp Lys Val Ser Leu Thr Cys Met Ile Thr Asp Phe Phe Pro Glu Asp
        290                 295                 300

Ile Thr Val Glu Trp Gln Trp Asn Gly Gln Pro Ala Glu Asn Tyr Lys
305                 310                 315                 320

Asn Thr Gln Pro Ile Met Asp Thr Asp Gly Ser Tyr Phe Val Tyr Ser
                325                 330                 335

Lys Leu Asn Val Gln Lys Ser Asn Trp Glu Ala Gly Asn Thr Phe Thr
                340                 345                 350

Cys Ser Val Leu His Glu Gly Leu His Asn His His Thr Glu Lys Ser
            355                 360                 365

Leu Ser His Ser Pro Gly Lys
    370                 375
```

<210> SEQ ID NO 9
<211> LENGTH: 660
<212> TYPE: DNA
<213> ORGANISM: Homo sapiens
<400> SEQUENCE: 9

```
tttactgtca cggttcccaa ggacctatat gtggtagagt atggtagcaa tatgacaatt    60
gaatgcaaat tcccagtaga aaacaattga cctggctg cactaattgt ctattgggaa    120
atggaggata agaacattat tcaatttgtg catggagagg aagacctgaa ggttcagcat    180
agtagctaca gacagagggc cggctgttg aaggaccagc tctccctggg aaatgctgca    240
cttcagatca cagatgtgaa attgcaggat gcaggggtgt accgctgcat gatcagctat    300
ggtggtgccg actacaagcg aattactgtg aaagtcaatg ccccatacaa caaaatcaac    360
caaagaattt tggttgtgga tccagtcacc tctgaacatg aactgacatg tcaggctgag    420
ggctacccca aggccgaagt catctggaca gcagtgacc atcaagtcct gagtggtaag    480
accaccacca ccaattccaa gagagaggag aagcttttca atgtgaccag cacactgaga    540
atcaacacaa caactaatga gatttttctac tgcacttttta ggagattaga tcctgaggaa    600
aaccatacag ctgaattggt catcccagaa ctacctctgg cacatcctcc aaatgaaagg    660
```

<210> SEQ ID NO 10
<211> LENGTH: 220
<212> TYPE: PRT
<213> ORGANISM: Homo sapiens
<400> SEQUENCE: 10

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60
```

| | | | | | | | | | | | | | | |
|---|---|---|---|---|---|---|---|---|---|---|---|---|---|---|
|Gln|Arg|Ala|Arg|Leu|Leu|Lys|Asp|Gln|Leu|Ser|Leu|Gly|Asn|Ala|Ala|
|65| | | |70| | | |75| | | |80| | |

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
            85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
            195                 200                 205

Pro Glu Leu Pro Leu Ala His Pro Pro Asn Glu Arg
    210                 215                 220

<210> SEQ ID NO 11
<211> LENGTH: 681
<212> TYPE: DNA
<213> ORGANISM: Homo sapiens

<400> SEQUENCE: 11

```
tttactgtca cggttcccaa ggacctatat gtggtagagt atggtagcaa tatgacaatt      60
gaatgcaaat tcccagtaga aaacaattga gacctggctg cactaattgt ctattgggaa     120
atggaggata agaacattat tcaatttgtg catggagagg aagacctgaa ggttcagcat     180
agtagctaca gacagagggc ccggctgttg aaggaccagc tctccctggg aaatgctgca     240
cttcagatca cagatgtgaa attgcaggat gcaggggtgt accgctgcat gatcagctat     300
ggtggtgccg actacaagcg aattactgtg aaagtcaatg ccccatacaa caaaatcaac     360
caaagaattt tggttgtgga tccagtcacc tctgaacatg aactgacatg tcaggctgag     420
ggctacccca aggccgaagt catctggaca agcagtgacc atcaagtcct gagtggtaag     480
accaccacca ccaattccaa gagagaggag aagcttttca atgtgaccag cactctgaga     540
atcaacacaa caactaatga gatttttctac tgcacttttta ggagattaga tcctgaggaa     600
aaccatacag ctgaattggt catcccagaa ctacctctgg cacatcctcc aaatgaaagg     660
catcatcacc accatcacta a                                                681
```

<210> SEQ ID NO 12
<211> LENGTH: 226
<212> TYPE: PRT
<213> ORGANISM: Homo sapiens

<400> SEQUENCE: 12

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

```
Phe Val His Gly Glu Glu Asp Leu Lys Val Gln His Ser Ser Tyr Arg
 50                  55                  60
Gln Arg Ala Arg Leu Leu Lys Asp Gln Leu Ser Leu Gly Asn Ala Ala
 65                  70                  75                  80
Leu Gln Ile Thr Asp Val Lys Leu Gln Asp Ala Gly Val Tyr Arg Cys
                 85                  90                  95
Met Ile Ser Tyr Gly Gly Ala Asp Tyr Lys Arg Ile Thr Val Lys Val
            100                 105                 110
Asn Ala Pro Tyr Asn Lys Ile Asn Gln Arg Ile Leu Val Val Asp Pro
        115                 120                 125
Val Thr Ser Glu His Glu Leu Thr Cys Gln Ala Glu Gly Tyr Pro Lys
130                 135                 140
Ala Glu Val Ile Trp Thr Ser Ser Asp His Gln Val Leu Ser Gly Lys
145                 150                 155                 160
Thr Thr Thr Thr Asn Ser Lys Arg Glu Glu Lys Leu Phe Asn Val Thr
                165                 170                 175
Ser Thr Leu Arg Ile Asn Thr Thr Thr Asn Glu Ile Phe Tyr Cys Thr
            180                 185                 190
Phe Arg Arg Leu Asp Pro Glu Glu Asn His Thr Ala Glu Leu Val Ile
        195                 200                 205
Pro Glu Leu Pro Leu Ala His Pro Pro Asn Glu Arg His His His His
    210                 215                 220
His His
225

<210> SEQ ID NO 13
<211> LENGTH: 1344
<212> TYPE: DNA
<213> ORGANISM: Homo sapiens

<400> SEQUENCE: 13
tttactgtca cggttcccaa ggacctatat gtggtagagt atggtagcaa tatgacaatt      60
gaatgcaaat tcccagtaga aaaacaatta gacctggctg cactaattgt ctattgggaa     120
atggaggata gaacattat tcaatttgtg catggagagg aagacctgaa ggttcagcat     180
agtagctaca gacagagggc ccggctgttg aaggaccagc tctccctggg aaatgctgca     240
cttcagatca cagatgtgaa attgcaggat gcaggggtgt accgctgcat gatcagctat     300
ggtggtgccg actacaagcg aattactgtg aaagtcaatg ccccatacaa caaaatcaac     360
caaagaattt tggttgtgga tccagtcacc tctgaacatg aactgacatg tcaggctgag     420
ggctacccca aggccgaagt catctggaca agcagtgacc atcaagtcct gagtggtaag     480
accaccacca ccaattccaa gagagaggag aagcttttca atgtgaccag cacactgaga     540
atcaacacaa caactaatga ttttctac tgcacttta ggagattaga tcctgaggaa     600
aaccatacag ctgaattggt catcccagaa ctacctctgg cacatcctcc aaatgaaagg     660
ggtaccagat ctagaggctg caaaccctgt atctgcacag tgcccgaggt gagctccgtg     720
ttcatctttc cccccaagcc caaggacgtg ctgaccatca cactcacacc caaggtcacc     780
tgcgtggtcg tggacatctc caaggacgac cccgaagtcc agttcagctg gttcgtggac     840
gacgtggagg tgcacaccgc tcagacccaa cccagagagg agcagtttaa ctccaccttc     900
aggtccgtgt ccgagctccc catcatgcac caggactggc tgaatggcaa ggagttcaag     960
tgcagggtga actccgctgc ttccccgccc ccattgaga gaccatctc caagaccaag    1020
ggaaggccca aggccccca ggtgtacacc attcccctc ccaaggagca gatggccaag    1080
```

```
gacaaggtgt ccctgacctg tatgatcacc gacttctttc ccgaggacat caccgtcgaa    1140
tggcagtgga acggccagcc cgccgagaac tataagaaca cccaaccat catggacacc     1200 gacggcagct acttcgtgta tagcaagctc aacgtgcaga agagcaactg ggaagccgga    1260
aataccttca cctgctccgt cctgcacgag ggcctgcaca accaccatac cgaaagagc    1320 ctgagccaca gccccggaaa gtaa                                            1344
```

<210> SEQ ID NO 14
<211> LENGTH: 447
<212> TYPE: PRT
<213> ORGANISM: Homo sapiens

<400> SEQUENCE: 14

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Gly Thr Arg Ser
    210                 215                 220

Arg Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320
```

```
Cys Arg Val Asn Ser Ala Ala Phe Pro Ala Pro Ile Glu Lys Thr Ile
            325                 330                 335

Ser Lys Thr Lys Gly Arg Pro Lys Ala Pro Gln Val Tyr Thr Ile Pro
        340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
        370                 375                 380

Gly Gln Pro Ala Glu Asn Tyr Lys Asn Thr Gln Pro Ile Met Asp Thr
385                 390                 395                 400

Asp Gly Ser Tyr Phe Val Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445
```

<210> SEQ ID NO 15
<211> LENGTH: 1374
<212> TYPE: DNA
<213> ORGANISM: Homo sapiens

<400> SEQUENCE: 15

```
tttactgtca cggttcccaa ggacctatat gtggtagagt atggtagcaa tatgacaatt      60
gaatgcaaat tcccagtaga aaacaattga cctggctgt cactaattgt ctattgggaa     120
atggaggata gaacattat tcaatttgtg catggagagg aagacctgaa ggttcagcat     180
agtagctaca gacagagggc ccggctgttg aaggaccagc tctccctggg aaatgctgca     240
cttcagatca cagatgtgaa attgcaggat gcagggtgt accgctgcat gatcagctat     300
ggtggtgccg actacaagcg aattactgtg aaagtcaatg ccccatacaa caaaatcaac     360
caaagaattt tggttgtgga tccagtcacc tctgaacatg aactgacatg tcaggctgag     420
ggctacccca aggccgaagt catctggaca agcagtgacc atcaagtcct gagtggtaag     480
accaccacca ccaattccaa gagagaggag aagcttttca atgtgaccag cacactgaga     540
atcaacacaa caactaatga ctttttctac tgcacttta ggagattaga tcctgaggaa     600
aaccatacag ctgaattggt catcccagaa ctacctctgg cacatcctcc aaatgaaagg     660
ggtaccagat ctagagagcc caaatcttct gacaaaactc acacatgccc accgtgccca     720
gcacctgaat cgagggtgc accgtcagtc ttcctcttcc ccccaaaacc caaggacacc     780
ctcatgatct cccggactcc tgaggtcaca tgcgtggtgg tggacgtaag ccacgaagac     840
cctgaggtca agttcaactg gtacgtggac ggcgtggagg tgcataatgc caagacaaag     900
ccgcgggagg agcagtacaa cagcacgtac cgtgtggtca gcgtcctcac cgtcctgcac     960
caggactggc tgaatggcaa ggagtacaag tgcaaggtct ccaacaaagc cctcccaacc    1020
cccatcgaga aaccatctc caaagccaaa gggcagcccc gagaaccaca ggtgtacacc    1080
ctgccccat ccggatga gctgaccaag aaccaggtca gcctgacctg cctggtcaaa    1140
ggcttctatc caagcgacat cgccgtggag tgggagagca atgggcagcc ggagaacaac    1200
tacaagacca cgcctcccgt gctggactcc gacggctcct tcttcctcta cagcaagctc    1260
accgtggaca gagcaggtg gcagcagggg aacgtcttct catgctccgt gatgcatgag    1320
gctctgcaca accactacac gcagaagagc ctctccctgt ctccgggtaa atga         1374
```

```
<210> SEQ ID NO 16
<211> LENGTH: 457
<212> TYPE: PRT
<213> ORGANISM: Homo sapiens

<400> SEQUENCE: 16
```

| | | | | | | | | | | | | | | |
|---|---|---|---|---|---|---|---|---|---|---|---|---|---|---|
Phe Thr Val Thr Val Pro Lys Asp Leu Tyr Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Gly Thr Arg Ser
210                 215                 220

Arg Glu Pro Lys Ser Ser Asp Lys Thr His Thr Cys Pro Pro Cys Pro
225                 230                 235                 240

Ala Pro Glu Phe Glu Gly Ala Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Thr Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
370                 375                 380

```
Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455
```

<210> SEQ ID NO 17
<211> LENGTH: 354
<212> TYPE: DNA
<213> ORGANISM: Mus sp.

<400> SEQUENCE: 17

```
gaagtgaagt tggtggagtc tgggggaggc ttagtgaagc ctggagggtc cctgaaactc     60
tcctgtgcag cctctggatt cactttcagt agttatggca tgtcttggct tcgccagact   120
ccggagaaga ggctggagtg ggtcgcaacc atgagtggtg ggggtcgtga catctactat   180
ccagacagta tgaaggggcg attcaccatc tccagagaca atgccaagaa caacctgtac   240
ctgcaaatga gcagtctgag gtctgaggac acggccttat attactgtgc aagacaatat   300
tacgacgact ggtttgctta ctggggccaa gggactctgg tcactgtctc tgca          354
```

<210> SEQ ID NO 18
<211> LENGTH: 118
<212> TYPE: PRT
<213> ORGANISM: Mus sp.

<400> SEQUENCE: 18

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Leu Arg Gln Thr Pro Glu Lys Arg Leu Glu Trp Val
        35                  40                  45

Ala Thr Met Ser Gly Gly Gly Arg Asp Ile Tyr Tyr Pro Asp Ser Met
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Arg Gln Tyr Tyr Asp Asp Trp Phe Ala Tyr Trp Gly Gln Gly Thr
            100                 105                 110

Leu Val Thr Val Ser Ala
        115
```

<210> SEQ ID NO 19
<211> LENGTH: 5
<212> TYPE: PRT
<213> ORGANISM: Mus sp.

<400> SEQUENCE: 19

```
Ser Tyr Gly Met Ser
1               5
```

```
<210> SEQ ID NO 20
<211> LENGTH: 17
<212> TYPE: PRT
<213> ORGANISM: Mus sp.

<400> SEQUENCE: 20

Thr Met Ser Gly Gly Gly Arg Asp Ile Tyr Tyr Pro Asp Ser Met Lys
1               5                   10                  15
Gly

<210> SEQ ID NO 21
<211> LENGTH: 9
<212> TYPE: PRT
<213> ORGANISM: Mus sp.

<400> SEQUENCE: 21

Gln Tyr Tyr Asp Asp Trp Phe Ala Tyr
1               5

<210> SEQ ID NO 22
<211> LENGTH: 324
<212> TYPE: DNA
<213> ORGANISM: Mus sp.

<400> SEQUENCE: 22
gatattgtgc tcacacagac tccagccacc ctgtctgtga ctccaggaga tagcgtcagt      60
ctctcctgca gggccagcca agtattagc aacaacctac actggtatca acaaaaatca     120
catgagtctc caaggcttct catcaagtat gcttcccagt ccatctctgg gatcccctcc     180
aggttcagtg gcagtggatc agggacagac ttcactctca atatcaacag tgtggagacc     240
gaagattttg gaatgtattt ctgtcaacag agtaacagct ggccgctcac gttcggtgct     300
gggaccaagc tggagctgaa acgg                                            324

<210> SEQ ID NO 23
<211> LENGTH: 108
<212> TYPE: PRT
<213> ORGANISM: Mus sp.

<400> SEQUENCE: 23

Asp Ile Val Leu Thr Gln Thr Pro Ala Thr Leu Ser Val Thr Pro Gly
1               5                   10                  15

Asp Ser Val Ser Leu Ser Cys Arg Ala Ser Gln Ser Ile Ser Asn Asn
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Thr Asp Phe Thr Leu Asn Ile Asn Ser Val Glu Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Leu Lys Arg
            100                 105

<210> SEQ ID NO 24
<211> LENGTH: 11
<212> TYPE: PRT
<213> ORGANISM: Mus sp.

<400> SEQUENCE: 24
```

```
Arg Ala Ser Gln Ser Ile Ser Asn Asn Leu His
1               5                   10
```

<210> SEQ ID NO 25
<211> LENGTH: 7
<212> TYPE: PRT
<213> ORGANISM: Mus sp.

<400> SEQUENCE: 25

```
Tyr Ala Ser Gln Ser Ile Ser
1               5
```

<210> SEQ ID NO 26
<211> LENGTH: 9
<212> TYPE: PRT
<213> ORGANISM: Mus sp.

<400> SEQUENCE: 26

```
Gln Gln Ser Asn Ser Trp Pro Leu Thr
1               5
```

<210> SEQ ID NO 27
<211> LENGTH: 366
<212> TYPE: DNA
<213> ORGANISM: Mus sp.

<400> SEQUENCE: 27

```
caggtgcagc tgaagcagtc aggacctggc ctggtgcagc cctcacagaa cctgtccgtc      60
acctgcacag tctctggttt ctcattaact acctatggtg tacactgggt tcgccagtct    120
ccaggaaagg gtctggagtg gctgggggtg atatggagtg gtggaagcac agactataat    180
gcggctttca tatccagact gaccatcagc aaggacaatg ccaggagcca agttttcttt    240
aaaatgaaca gtctgcaagt taatgacaca gccatgtatt actgtgccag agagaaaagc    300
gtctatggta attacgtggg ggctatggac tactggggtc aaggaacctc agtcaccgtc    360
tcctca                                                               366
```

<210> SEQ ID NO 28
<211> LENGTH: 122
<212> TYPE: PRT
<213> ORGANISM: Mus sp.

<400> SEQUENCE: 28

```
Gln Val Gln Leu Lys Gln Ser Gly Pro Gly Leu Val Gln Pro Ser Gln
1               5                   10                  15

Asn Leu Ser Val Thr Cys Thr Val Ser Gly Phe Ser Leu Thr Thr Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Thr Ile Ser Lys Asp Asn Ala Arg Ser Gln Val Phe Phe
65                  70                  75                  80

Lys Met Asn Ser Leu Gln Val Asn Asp Thr Ala Met Tyr Tyr Cys Ala
                85                  90                  95

Arg Glu Lys Ser Val Tyr Gly Asn Tyr Val Gly Ala Met Asp Tyr Trp
            100                 105                 110

Gly Gln Gly Thr Ser Val Thr Val Ser Ser
        115                 120
```

<210> SEQ ID NO 29
<211> LENGTH: 5
<212> TYPE: PRT
<213> ORGANISM: Mus sp.

<400> SEQUENCE: 29

Thr Tyr Gly Val His
1               5

<210> SEQ ID NO 30
<211> LENGTH: 16
<212> TYPE: PRT
<213> ORGANISM: Mus sp.

<400> SEQUENCE: 30

Val Ile Trp Ser Gly Gly Ser Thr Asp Tyr Asn Ala Ala Phe Ile Ser
1               5                   10                  15

<210> SEQ ID NO 31
<211> LENGTH: 14
<212> TYPE: PRT
<213> ORGANISM: Mus sp.

<400> SEQUENCE: 31

Glu Lys Ser Val Tyr Gly Asn Tyr Val Gly Ala Met Asp Tyr
1               5                   10

<210> SEQ ID NO 32
<211> LENGTH: 324
<212> TYPE: DNA
<213> ORGANISM: Mus sp.

<400> SEQUENCE: 32
agtattgtga tgacccagac tcccaaattc ctgcttgtat cagcgggaga cagggttacc      60
ataacctgca aggccagtca gagtgtgagt gatgatgtag cttggtacca acagaagcca     120
gggcagtctc ctaaactgct gatatactat gcattcaatc gctacactgg agtccctgat     180
cgcttcactg gcagtggata tgggacggat ttcactttca ccatcagcac tgtgcagtct     240
gaagacctgg cagtttattt ctgtcagcag gattatcgct ctccgtggac gttcggtgga     300
ggcaccaagc tggaaatcaa acgg                                             324

<210> SEQ ID NO 33
<211> LENGTH: 108
<212> TYPE: PRT
<213> ORGANISM: Mus sp.

<400> SEQUENCE: 33

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asp Asp
            20                  25                  30

Val Ala Trp Tyr Gln Gln Lys Pro Gly Gln Ser Pro Lys Leu Leu Ile
        35                  40                  45

Tyr Tyr Ala Phe Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ser
65                  70                  75                  80

Glu Asp Leu Ala Val Tyr Phe Cys Gln Gln Asp Tyr Arg Ser Pro Trp
                85                  90                  95

Thr Phe Gly Gly Gly Thr Lys Leu Glu Ile Lys Arg
            100                 105

<210> SEQ ID NO 34
<211> LENGTH: 11
<212> TYPE: PRT
<213> ORGANISM: Mus sp.

<400> SEQUENCE: 34

Lys Ala Ser Gln Ser Val Ser Asp Asp Val Ala
1               5                   10

<210> SEQ ID NO 35
<211> LENGTH: 7
<212> TYPE: PRT
<213> ORGANISM: Mus sp.

<400> SEQUENCE: 35

Tyr Ala Phe Asn Arg Tyr Thr
1               5

<210> SEQ ID NO 36
<211> LENGTH: 9
<212> TYPE: PRT
<213> ORGANISM: Mus sp.

<400> SEQUENCE: 36

Gln Gln Asp Tyr Arg Ser Pro Trp Thr
1               5

<210> SEQ ID NO 37
<211> LENGTH: 9
<212> TYPE: PRT
<213> ORGANISM: Mus sp.

<400> SEQUENCE: 37

Gln Gln Asp Tyr Arg Ser Pro Trp Thr
1               5

<210> SEQ ID NO 38
<211> LENGTH: 354
<212> TYPE: DNA
<213> ORGANISM: Mus sp.

<400> SEQUENCE: 38
gaagtgaagt tggtggagtc ggggggaggc ttagtgaagc ctggagggtc cctgaaactc      60
tcctgtggag cctctggatt cactttcagt agttatggca tgtcttgggt tcgccagact     120
ccggagaaga ggctggagtg ggtcgcaacc attagtggtg gtggtagaga tatttattat     180
ccagacagtg tgaaggggcg actcaccatc tccagagaca atgccaagaa caacctgtac     240
ctgcaaatga gcagtctgag gtctgaggac acggccttgt attactgtgt aagacaatat     300
tacgacgact ggttcgctta ttggggccaa gggactctgg tcactgtctc tgca           354

<210> SEQ ID NO 39
<211> LENGTH: 118
<212> TYPE: PRT
<213> ORGANISM: Mus sp.

<400> SEQUENCE: 39

Glu Val Lys Leu Val Glu Ser Gly Gly Gly Leu Val Lys Pro Gly Gly
1               5                   10                  15

```
Ser Leu Lys Leu Ser Cys Gly Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Thr Ile Ser Gly Gly Arg Asp Ile Tyr Tyr Pro Asp Ser Val
50                  55                  60

Lys Gly Arg Leu Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Val Arg Gln Tyr Tyr Asp Asp Trp Phe Ala Tyr Trp Gly Gln Gly Thr
            100                 105                 110

Leu Val Thr Val Ser Ala
            115

<210> SEQ ID NO 40
<211> LENGTH: 5
<212> TYPE: PRT
<213> ORGANISM: Mus sp.

<400> SEQUENCE: 40

Ser Tyr Gly Met Ser
1               5

<210> SEQ ID NO 41
<211> LENGTH: 17
<212> TYPE: PRT
<213> ORGANISM: Mus sp.

<400> SEQUENCE: 41

Thr Ile Ser Gly Gly Arg Asp Ile Tyr Tyr Pro Asp Ser Val Lys
1               5                   10                  15

Gly

<210> SEQ ID NO 42
<211> LENGTH: 9
<212> TYPE: PRT
<213> ORGANISM: Mus sp.

<400> SEQUENCE: 42

Gln Tyr Tyr Asp Asp Trp Phe Ala Tyr
1               5

<210> SEQ ID NO 43
<211> LENGTH: 324
<212> TYPE: DNA
<213> ORGANISM: Mus sp.

<400> SEQUENCE: 43
gacattgtgc tgacacagtc tccagccacc ctgtctgtga ctccaggaga tagcgtcagt      60
ctttcctgca gggccagcca agtattagc aacgaccttc actggtatca acaaaaatca     120
catgagtctc caaggcttct catcaagtat gtttcccagt ccatctctgg atcccctcc      180 aggttcagtg gcagtggatc agggacggat tcactctca gtatcaacag tgtggagact      240
gaggattttg gaatgtattt ctgtcaacag agtgacagct ggccgctcac gttcggtgct      300
gggaccaagc tggagctgaa acgg                                             324

<210> SEQ ID NO 44
<211> LENGTH: 108
```

<212> TYPE: PRT
<213> ORGANISM: Mus sp.

<400> SEQUENCE: 44

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asp
            20                  25                  30

Leu His Trp Tyr Gln Gln Lys Ser His Glu Ser Pro Arg Leu Leu Ile
        35                  40                  45

Lys Tyr Val Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asp Ser Trp Pro Leu
                85                  90                  95

Thr Phe Gly Ala Gly Thr Lys Leu Glu Leu Lys Arg
            100                 105

<210> SEQ ID NO 45
<211> LENGTH: 11
<212> TYPE: PRT
<213> ORGANISM: Mus sp.

<400> SEQUENCE: 45

Arg Ala Ser Gln Ser Ile Ser Asn Asp Leu His
1               5                   10

<210> SEQ ID NO 46
<211> LENGTH: 7
<212> TYPE: PRT
<213> ORGANISM: Mus sp.

<400> SEQUENCE: 46

Tyr Val Ser Gln Ser Ile Ser
1               5

<210> SEQ ID NO 47
<211> LENGTH: 9
<212> TYPE: PRT
<213> ORGANISM: Mus sp.

<400> SEQUENCE: 47

Gln Gln Ser Asp Ser Trp Pro Leu Thr
1               5

<210> SEQ ID NO 48
<211> LENGTH: 360
<212> TYPE: DNA
<213> ORGANISM: Mus sp.

<400> SEQUENCE: 48
gatgtgcagc ttcaggagtc gggacctggc ctggtgaaac cttctcagtc tctgtccctc      60
acctgcactg tcactggcta ctcaatcacc agtgattatg cctggaactg gatccggcag     120
tttccaggaa accaactgga gtggatggcc tacattagtt acagtggtta cactagctac     180
aacccatctc tcaaaagtcg aatctctatc actcgagaca catccaagaa ccagttcttc     240
ctgcagttga attctgtgac tactgaggac acagccacat attactgtgc aagatctctt     300
gactatgatt acggaactat ggactactgg ggtcaaggaa cctcagtcac cgtctcctca     360

<210> SEQ ID NO 49
<211> LENGTH: 120
<212> TYPE: PRT
<213> ORGANISM: Mus sp.

<400> SEQUENCE: 49

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Gln Leu Glu Trp
        35                  40                  45

Met Ala Tyr Ile Ser Tyr Ser Gly Tyr Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Leu Asp Tyr Asp Tyr Gly Thr Met Asp Tyr Trp Gly Gln
            100                 105                 110

Gly Thr Ser Val Thr Val Ser Ser
        115                 120

<210> SEQ ID NO 50
<211> LENGTH: 6
<212> TYPE: PRT
<213> ORGANISM: Mus sp.

<400> SEQUENCE: 50

Ser Asp Tyr Ala Trp Asn
1               5

<210> SEQ ID NO 51
<211> LENGTH: 16
<212> TYPE: PRT
<213> ORGANISM: Mus sp.

<400> SEQUENCE: 51

Tyr Ile Ser Tyr Ser Gly Tyr Thr Ser Tyr Asn Pro Ser Leu Lys Ser
1               5                   10                  15

<210> SEQ ID NO 52
<211> LENGTH: 11
<212> TYPE: PRT
<213> ORGANISM: Mus sp.

<400> SEQUENCE: 52

Ser Leu Asp Tyr Asp Tyr Gly Thr Met Asp Tyr
1               5                   10

<210> SEQ ID NO 53
<211> LENGTH: 321
<212> TYPE: DNA
<213> ORGANISM: Mus sp.

<400> SEQUENCE: 53
caaattgttc tctcccagtc tccagcaatc ctgtctgcat ctccagggga gaaggtcaca    60
atgacctgca gggccaactc aagtgtaagt tccatgcact ggtaccagca gaagccagga   120
tcctcccccg aaccctggat ttatgccatt tccaacctgg cttttggagt ccctactcgc   180

```
ttcagtggca gtgggtctgg gacctcttac tctctcacaa tcagcagagt ggaggctgaa    240
gatgctgcca cttatttctg ccagcagtgg agtagtagac cacccacgtt cggagggggg    300
accaagctgg aaataaaacg g                                               321
```

<210> SEQ ID NO 54
<211> LENGTH: 107
<212> TYPE: PRT
<213> ORGANISM: Mus sp.

<400> SEQUENCE: 54

```
Gln Ile Val Leu Ser Gln Ser Pro Ala Ile Leu Ser Ala Ser Pro Gly
1               5                   10                  15

Glu Lys Val Thr Met Thr Cys Arg Ala Asn Ser Ser Val Ser Ser Met
            20                  25                  30

His Trp Tyr Gln Gln Lys Pro Gly Ser Ser Pro Glu Pro Trp Ile Tyr
        35                  40                  45

Ala Ile Ser Asn Leu Ala Phe Gly Val Pro Thr Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys Gln Gln Trp Ser Ser Arg Pro Pro Thr
                85                  90                  95

Phe Gly Gly Gly Thr Lys Leu Glu Ile Lys Arg
            100                 105
```

<210> SEQ ID NO 55
<211> LENGTH: 10
<212> TYPE: PRT
<213> ORGANISM: Mus sp.

<400> SEQUENCE: 55

```
Arg Ala Asn Ser Ser Val Ser Ser Met His
1               5                   10
```

<210> SEQ ID NO 56
<211> LENGTH: 7
<212> TYPE: PRT
<213> ORGANISM: Mus sp.

<400> SEQUENCE: 56

```
Ala Ile Ser Asn Leu Ala Phe
1               5
```

<210> SEQ ID NO 57
<211> LENGTH: 9
<212> TYPE: PRT
<213> ORGANISM: Mus sp.

<400> SEQUENCE: 57

```
Gln Gln Trp Ser Ser Arg Pro Pro Thr
1               5
```

<210> SEQ ID NO 58
<211> LENGTH: 351
<212> TYPE: DNA
<213> ORGANISM: Mus sp.

<400> SEQUENCE: 58

```
gaagtgaagc tggtggagtc tgggggaggc ttagtgaagc ctggagggtc cctgaaactc    60
tcctgtgcag cctctggatt cgctttccgt agctatgaca tgtcttgggt tcgccagact   120
```

```
ccggagaaga tcctggagtg ggtcgcaacc attagtggtg gtggtagtta cacctactat    180
caagacagtg tgaagggccg attcaccatc tccagagaca atgccaggaa caccctgtac    240
ctgcaaatga gcagtctgag gtctgaggac acggccttgt attactgtgc aagcccctat    300
ggcccctact ttgactactg gggccaaggc accactctca cagtctcctc a             351
```

<210> SEQ ID NO 59
<211> LENGTH: 117
<212> TYPE: PRT
<213> ORGANISM: Mus sp.

<400> SEQUENCE: 59

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ala Phe Arg Ser Tyr
            20                  25                  30

Asp Met Ser Trp Val Arg Gln Thr Pro Glu Lys Ile Leu Glu Trp Val
        35                  40                  45

Ala Thr Ile Ser Gly Gly Gly Ser Tyr Thr Tyr Tyr Gln Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Ala Ser Pro Tyr Gly Pro Tyr Phe Asp Tyr Trp Gly Gln Gly Thr Thr
            100                 105                 110

Leu Thr Val Ser Ser
        115
```

<210> SEQ ID NO 60
<211> LENGTH: 5
<212> TYPE: PRT
<213> ORGANISM: Mus sp.

<400> SEQUENCE: 60

```
Ser Tyr Asp Met Ser
1               5
```

<210> SEQ ID NO 61
<211> LENGTH: 17
<212> TYPE: PRT
<213> ORGANISM: Mus sp.

<400> SEQUENCE: 61

```
Thr Ile Ser Gly Gly Gly Ser Tyr Thr Tyr Tyr Gln Asp Ser Val Lys
1               5                   10                  15

Gly
```

<210> SEQ ID NO 62
<211> LENGTH: 8
<212> TYPE: PRT
<213> ORGANISM: Mus sp.

<400> SEQUENCE: 62

```
Pro Tyr Gly Pro Tyr Phe Asp Tyr
1               5
```

<210> SEQ ID NO 63
<211> LENGTH: 324

<212> TYPE: DNA
<213> ORGANISM: Mus sp.

<400> SEQUENCE: 63

```
gacatccaga tgaaccagtc tccatccagt ctgtctgcat cccttggaga cacgattacc    60
atcacttgcc atgccagtca gagcattaat gtttggttaa gctggtacca gcagaaacca   120
ggaaatattc ctaaactatt gatctatagg gcttccaact tgcacacagg cgtcccatca   180
aggtttagtg gcagtggatc tggaacaggt ttcacattaa ccatcagcag cctgcagcct   240
gacgacattg ccacttacta ctgtcaacag ggtcaaagtt atccgtggac gttcggtgga   300
ggcaccaagc tggaaatcaa acgg                                          324
```

<210> SEQ ID NO 64
<211> LENGTH: 108
<212> TYPE: PRT
<213> ORGANISM: Mus sp.

<400> SEQUENCE: 64

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Ser Ile Asn Val Trp
            20                  25                  30

Leu Ser Trp Tyr Gln Gln Lys Pro Gly Asn Ile Pro Lys Leu Leu Ile
        35                  40                  45

Tyr Arg Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Asp Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys Arg
            100                 105

<210> SEQ ID NO 65
<211> LENGTH: 11
<212> TYPE: PRT
<213> ORGANISM: Mus sp.

<400> SEQUENCE: 65

His Ala Ser Gln Ser Ile Asn Val Trp Leu Ser
1               5                   10

<210> SEQ ID NO 66
<211> LENGTH: 6
<212> TYPE: PRT
<213> ORGANISM: Mus sp.

<400> SEQUENCE: 66

Ala Ser Asn Leu His Thr
1               5

<210> SEQ ID NO 67
<211> LENGTH: 9
<212> TYPE: PRT
<213> ORGANISM: Mus sp.

<400> SEQUENCE: 67

Gln Gln Gly Gln Ser Tyr Pro Trp Thr
1               5

<210> SEQ ID NO 68
<211> LENGTH: 360
<212> TYPE: DNA
<213> ORGANISM: Mus sp.

<400> SEQUENCE: 68
gatgtgcagc ttcaggagtc gggacctggc ctggtgaaac cttctcagtc tctgtccctc    60
acctgcactg tcactggcta ctcaatcacc agtgattatg cctggaactg gatccggcag   120
tttccaggaa accaactgga gtggatggcc tacattagct acagtggtta cactagctac   180
aacccatctc tcaaaagtcg aatctctatc actcgagaca catccaggaa ccagttcttc   240
ctgcagttga attctgtgac tactgaggac acagccacat attactgtgc aagatctctt   300
gactatgatt acggaactat ggactactgg ggtcaaggaa cctcagtcac cgtctcctca   360

<210> SEQ ID NO 69
<211> LENGTH: 120
<212> TYPE: PRT
<213> ORGANISM: Mus sp.

<400> SEQUENCE: 69

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Gln Leu Glu Trp
        35                  40                  45

Met Ala Tyr Ile Ser Tyr Ser Gly Tyr Thr Ser Tyr Asn Pro Ser Leu
    50                  55                  60

Lys Ser Arg Ile Ser Ile Thr Arg Asp Thr Ser Arg Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Leu Asp Tyr Asp Tyr Gly Thr Met Asp Tyr Trp Gly Gln
            100                 105                 110

Gly Thr Ser Val Thr Val Ser Ser
        115                 120

<210> SEQ ID NO 70
<211> LENGTH: 6
<212> TYPE: PRT
<213> ORGANISM: Mus sp.

<400> SEQUENCE: 70

Ser Asp Tyr Ala Trp Asn
1               5

<210> SEQ ID NO 71
<211> LENGTH: 16
<212> TYPE: PRT
<213> ORGANISM: Mus sp.

<400> SEQUENCE: 71

Tyr Ile Ser Tyr Ser Gly Tyr Thr Ser Tyr Asn Pro Ser Leu Lys Ser
1               5                   10                  15

<210> SEQ ID NO 72
<211> LENGTH: 11
<212> TYPE: PRT
<213> ORGANISM: Mus sp.

<400> SEQUENCE: 72

Ser Leu Asp Tyr Asp Tyr Gly Thr Met Asp Tyr
1               5                   10

<210> SEQ ID NO 73
<211> LENGTH: 321
<212> TYPE: DNA
<213> ORGANISM: Mus sp.

<400> SEQUENCE: 73
caaattgttc tctcccagtc tccagcaatc ctgtctgcat ctccagggga gaaggtcaca    60
atgacctgca gggccaactc aagtgtaagt tccatgcact ggtaccaaca gaagccagga   120
tcctcccccg aaccctggat ttatgccatt tccaacctgg cttttggagt ccctgctcgc   180
ttcagtggca gtgggtctgg gacctcttac tctctcacaa tcagcagagt ggaggctgaa   240
gatgctgcca cttatttctg ccagcaatgg aatagtagac cacccacgtt cggagggggg   300
accaagctgg aaataaaacg g                                             321

<210> SEQ ID NO 74
<211> LENGTH: 107
<212> TYPE: PRT
<213> ORGANISM: Mus sp.

<400> SEQUENCE: 74

Gln Ile Val Leu Ser Gln Ser Pro Ala Ile Leu Ser Ala Ser Pro Gly
1               5                   10                  15

Glu Lys Val Thr Met Thr Cys Arg Ala Asn Ser Ser Val Ser Ser Met
            20                  25                  30

His Trp Tyr Gln Gln Lys Pro Gly Ser Ser Pro Glu Pro Trp Ile Tyr
        35                  40                  45

Ala Ile Ser Asn Leu Ala Phe Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys Gln Gln Trp Asn Ser Arg Pro Pro Thr
                85                  90                  95

Phe Gly Gly Gly Thr Lys Leu Glu Ile Lys Arg
            100                 105

<210> SEQ ID NO 75
<211> LENGTH: 10
<212> TYPE: PRT
<213> ORGANISM: Mus sp.

<400> SEQUENCE: 75

Arg Ala Asn Ser Ser Val Ser Ser Met His
1               5                   10

<210> SEQ ID NO 76
<211> LENGTH: 7
<212> TYPE: PRT
<213> ORGANISM: Mus sp.

<400> SEQUENCE: 76

Ala Ile Ser Asn Leu Ala Phe
1               5

<210> SEQ ID NO 77

```
<211> LENGTH: 9
<212> TYPE: PRT
<213> ORGANISM: Mus sp.

<400> SEQUENCE: 77

Gln Gln Trp Asn Ser Arg Pro Pro Thr
1               5

<210> SEQ ID NO 78
<211> LENGTH: 351
<212> TYPE: DNA
<213> ORGANISM: Mus sp.

<400> SEQUENCE: 78
gaagtgaaac tggtggagtc tgggggaggc ttagtgaagc ctggagggtc cctgaaactc      60
tcctgttcag cctctggatt cagtttcagt tactatgaca tgtcttgggt tcggcagact     120
ccggagaagg gactggagtg ggtcgcaacc attagtggtg gtggtagaaa taccattttt     180
atagacagtg tgaaggggcg attcaccatc tccagagaca atgtcaagaa caacctgtat     240
ctgctaatga gcagtctgag gtctgaggat acggccttgt attactgtgc aagcccctat     300
gagggggctg tggacttctg gggtcaagga acctcagtca ccgtctcctc a              351

<210> SEQ ID NO 79
<211> LENGTH: 117
<212> TYPE: PRT
<213> ORGANISM: Mus sp.

<400> SEQUENCE: 79

Glu Val Lys Leu Val Glu Ser Gly Gly Gly Leu Val Lys Pro Gly Gly
1               5                   10                  15

Ser Leu Lys Leu Ser Cys Ser Ala Ser Gly Phe Ser Phe Ser Tyr Tyr
            20                  25                  30

Asp Met Ser Trp Val Arg Gln Thr Pro Glu Lys Gly Leu Glu Trp Val
        35                  40                  45

Ala Thr Ile Ser Gly Gly Gly Arg Asn Thr Tyr Phe Ile Asp Ser Val
    50                  55                  60

Lys Gly Arg Phe Thr Ile Ser Arg Asp Asn Val Lys Asn Asn Leu Tyr
65                  70                  75                  80

Leu Leu Met Ser Ser Leu Arg Ser Glu Asp Thr Ala Leu Tyr Tyr Cys
                85                  90                  95

Ala Ser Pro Tyr Glu Gly Ala Val Asp Phe Trp Gly Gln Gly Thr Ser
            100                 105                 110

Val Thr Val Ser Ser
        115

<210> SEQ ID NO 80
<211> LENGTH: 5
<212> TYPE: PRT
<213> ORGANISM: Mus sp.

<400> SEQUENCE: 80

Tyr Tyr Asp Met Ser
1               5

<210> SEQ ID NO 81
<211> LENGTH: 17
<212> TYPE: PRT
<213> ORGANISM: Mus sp.

<400> SEQUENCE: 81
```

```
Thr Ile Ser Gly Gly Gly Arg Asn Thr Tyr Phe Ile Asp Ser Val Lys
1               5                   10                  15

Gly
```

<210> SEQ ID NO 82
<211> LENGTH: 8
<212> TYPE: PRT
<213> ORGANISM: Mus sp.

<400> SEQUENCE: 82

```
Pro Tyr Glu Gly Ala Val Asp Phe
1               5
```

<210> SEQ ID NO 83
<211> LENGTH: 324
<212> TYPE: DNA
<213> ORGANISM: Mus sp.

<400> SEQUENCE: 83

```
gacattgtga tgacccagtc tcacaaagtc atgtccacat cagtaggaga cagggtcagc    60
atcacctgca aggccagtca ggatgtggat aatgctgtag cctggtatca acagaatccc   120
ggacaatctc ctaaactact gattaagtgg gcatccaccc gacaccatgg agtccctgat   180
cgcttcacag gcagtggatc tgggacagat ttcactctca ccattagcac tgtgcaatct   240
gaagacttgg cagattttt ctgtcagcaa tatagcacct ttccgtacac gttcggaggg    300
gggaccaagc tggaaataaa acgg                                          324
```

<210> SEQ ID NO 84
<211> LENGTH: 108
<212> TYPE: PRT
<213> ORGANISM: Mus sp.

<400> SEQUENCE: 84

```
Asp Ile Val Met Thr Gln Ser His Lys Val Met Ser Thr Ser Val Gly
1               5                   10                  15

Asp Arg Val Ser Ile Thr Cys Lys Ala Ser Gln Asp Val Asp Asn Ala
            20                  25                  30

Val Ala Trp Tyr Gln Gln Asn Pro Gly Gln Ser Pro Lys Leu Leu Ile
        35                  40                  45

Lys Trp Ala Ser Thr Arg His His Gly Val Pro Asp Arg Phe Thr Gly
50                  55                  60

Ser Gly Ser Gly Thr Asp Phe Thr Leu Thr Ile Ser Thr Val Gln Ser
65                  70                  75                  80

Glu Asp Leu Ala Asp Phe Phe Cys Gln Gln Tyr Ser Thr Phe Pro Tyr
                85                  90                  95

Thr Phe Gly Gly Gly Thr Lys Leu Glu Ile Lys Arg
            100                 105
```

<210> SEQ ID NO 85
<211> LENGTH: 11
<212> TYPE: PRT
<213> ORGANISM: Mus sp.

<400> SEQUENCE: 85

```
Lys Ala Ser Gln Asp Val Asp Asn Ala Val Ala
1               5                   10
```

<210> SEQ ID NO 86

```
<211> LENGTH: 7
<212> TYPE: PRT
<213> ORGANISM: Mus sp.

<400> SEQUENCE: 86

Trp Ala Ser Thr Arg His His
1               5

<210> SEQ ID NO 87
<211> LENGTH: 9
<212> TYPE: PRT
<213> ORGANISM: Mus sp.

<400> SEQUENCE: 87

Gln Gln Tyr Ser Thr Phe Pro Tyr Thr
1               5

<210> SEQ ID NO 88
<211> LENGTH: 354
<212> TYPE: DNA
<213> ORGANISM: Mus sp.

<400> SEQUENCE: 88
gaagtgaagt tggtggagtc tgggggaggc ttagtgaagc ctggagggtc cctgaaactc      60
tcctgtgcag cctctggatt cactttcagt agctatggca tgtcttgggt tcgccagact     120
ccggagaaga ggctggagtg ggtcgcaacc attagtggtg gtggtcgtga cacctactat     180
ctagacagtg tgaaggggcg attcaccatc tccagagaca atgccaagaa caacctgtat     240
ttgcaaatga gcagtctgag gtctgaggac acggccttgt attactgtgt gagacagtat     300
tacgacgact ggtttgctta ctggggccaa gggactctgg tctctaactc tgca           354

<210> SEQ ID NO 89
<211> LENGTH: 118
<212> TYPE: PRT
<213> ORGANISM: Mus sp.

<400> SEQUENCE: 89

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Thr Ile Ser Gly Gly Gly Arg Asp Thr Tyr Tyr Leu Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Val Arg Gln Tyr Tyr Asp Asp Trp Phe Ala Tyr Trp Gly Gln Gly Thr
            100                 105                 110

Leu Val Ser Asn Ser Ala
        115

<210> SEQ ID NO 90
<211> LENGTH: 5
<212> TYPE: PRT
<213> ORGANISM: Mus sp.

<400> SEQUENCE: 90
```

```
Ser Tyr Gly Met Ser
1               5

<210> SEQ ID NO 91
<211> LENGTH: 17
<212> TYPE: PRT
<213> ORGANISM: Mus sp.

<400> SEQUENCE: 91

Thr Ile Ser Gly Gly Gly Arg Asp Thr Tyr Tyr Leu Asp Ser Val Lys
1               5                   10                  15

Gly

<210> SEQ ID NO 92
<211> LENGTH: 9
<212> TYPE: PRT
<213> ORGANISM: Mus sp.

<400> SEQUENCE: 92

Gln Tyr Tyr Asp Asp Trp Phe Ala Tyr
1               5

<210> SEQ ID NO 93
<211> LENGTH: 321
<212> TYPE: DNA
<213> ORGANISM: Mus sp.

<400> SEQUENCE: 93
gatattgtgc tcacccagac tccagccacc ctttctgtga ctccaggaga tagtgtcagt      60
ctttcctgca gggccagcca agtcttagc aacaacctac actggtatca acaaaaatca     120
catgagtctc caaggcttct catcaagtat gcttcccagt ccatctctgg gatcccctcc     180
aggttcagtg gcagtggatc aggacagat ttcactctca gtatcaacag tgtggagact     240
gaagattttg gaatgtattt ctgtcaacag agtaacagct ggccgctcac gttcggtgct     300
gggaccaagc tggagatgaa a                                               321

<210> SEQ ID NO 94
<211> LENGTH: 108
<212> TYPE: PRT
<213> ORGANISM: Mus sp.

<400> SEQUENCE: 94

Asp Ile Val Leu Thr Gln Thr Pro Ala Thr Leu Ser Val Thr Pro Gly
1               5                   10                  15

Asp Ser Val Ser Leu Ser Cys Arg Ala Ser Gln Ser Leu Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Met Lys Arg
            100                 105

<210> SEQ ID NO 95
```

```
<211> LENGTH: 11
<212> TYPE: PRT
<213> ORGANISM: Mus sp.

<400> SEQUENCE: 95

Arg Ala Ser Gln Ser Leu Ser Asn Asn Leu His
1               5                   10

<210> SEQ ID NO 96
<211> LENGTH: 7
<212> TYPE: PRT
<213> ORGANISM: Mus sp.

<400> SEQUENCE: 96

Tyr Ala Ser Gln Ser Ile Ser
1               5

<210> SEQ ID NO 97
<211> LENGTH: 9
<212> TYPE: PRT
<213> ORGANISM: Mus sp.

<400> SEQUENCE: 97

Gln Gln Ser Asn Ser Trp Pro Leu Thr
1               5

<210> SEQ ID NO 98
<211> LENGTH: 360
<212> TYPE: DNA
<213> ORGANISM: Mus sp.

<400> SEQUENCE: 98
caggtccagc tgcagcagtc tggagatgag ctggtaaggc ctgggacttc agtgaagatg      60
tcctgcaagg ctgctggata caccttcact aacaactgga taggttgggt aaagcagagg     120
cctggacatg gccttgagtg gattggagat ttctaccctg gaggtggtta tactaactac     180
aatgagaagt tcaagggcaa ggccacactg actgcagaca catcctccag cacagcctac     240
atgcagctca gcagcctgac atctgaggac tctgccatct attactgtgc aagaggctac     300
ggtactaact actggtactt cgatgtctgg ggcgcaggga ccacggtcac cgtctcctca     360

<210> SEQ ID NO 99
<211> LENGTH: 120
<212> TYPE: PRT
<213> ORGANISM: Mus sp.

<400> SEQUENCE: 99

Gln Val Gln Leu Gln Gln Ser Gly Asp Glu Leu Val Arg Pro Gly Thr
1               5                   10                  15

Ser Val Lys Met Ser Cys Lys Ala Ala Gly Tyr Thr Phe Thr Asn Asn
                20                  25                  30

Trp Ile Gly Trp Val Lys Gln Arg Pro Gly His Gly Leu Glu Trp Ile
            35                  40                  45

Gly Asp Phe Tyr Pro Gly Gly Gly Tyr Thr Asn Tyr Asn Glu Lys Phe
        50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg Gly Tyr Gly Thr Asn Tyr Trp Tyr Phe Asp Val Trp Gly Ala
            100                 105                 110
```

-continued

Gly Thr Thr Val Thr Val Ser Ser
        115                 120

<210> SEQ ID NO 100
<211> LENGTH: 5
<212> TYPE: PRT
<213> ORGANISM: Mus sp.

<400> SEQUENCE: 100

Asn Asn Trp Ile Gly
1               5

<210> SEQ ID NO 101
<211> LENGTH: 17
<212> TYPE: PRT
<213> ORGANISM: Mus sp.

<400> SEQUENCE: 101

Asp Phe Tyr Pro Gly Gly Gly Tyr Thr Asn Tyr Asn Glu Lys Phe Lys
1               5                   10                  15

Gly

<210> SEQ ID NO 102
<211> LENGTH: 11
<212> TYPE: PRT
<213> ORGANISM: Mus sp.

<400> SEQUENCE: 102

Gly Tyr Gly Thr Asn Tyr Trp Tyr Phe Asp Val
1               5                   10

<210> SEQ ID NO 103
<211> LENGTH: 324
<212> TYPE: DNA
<213> ORGANISM: Mus sp.

<400> SEQUENCE: 103
aatattgtga tgacccagac tcccaaaatc ctgtttatat cagcaggaga cagggttacc      60
ataacctgca aggccagtca gagtgtgagt aatgatgtag cttggtacca acagaagcca     120
gggcagtctc ctaaactgct gatatactat gcattcactc gctacattgg agtccctgat     180
cgcttcactg gcagtggata tgggacggat ttcactttca ccatcagcac tgtgcaggct     240
gaagacctgg cagtttattt ctgtcagcag gattatagct ctccttacac gttcggaggg     300
gggaccaagc tggaaataaa acgg                                            324

<210> SEQ ID NO 104
<211> LENGTH: 108
<212> TYPE: PRT
<213> ORGANISM: Mus sp.

<400> SEQUENCE: 104

Asn Ile Val Met Thr Gln Thr Pro Lys Ile Leu Phe Ile Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Phe Thr Arg Tyr Ile Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys Arg
            100                 105

<210> SEQ ID NO 105
<211> LENGTH: 11
<212> TYPE: PRT
<213> ORGANISM: Mus sp.

<400> SEQUENCE: 105

Lys Ala Ser Gln Ser Val Ser Asn Asp Val Ala
1               5                   10

<210> SEQ ID NO 106
<211> LENGTH: 7
<212> TYPE: PRT
<213> ORGANISM: Mus sp.

<400> SEQUENCE: 106

Tyr Ala Phe Thr Arg Tyr Ile
1               5

<210> SEQ ID NO 107
<211> LENGTH: 9
<212> TYPE: PRT
<213> ORGANISM: Mus sp.

<400> SEQUENCE: 107

Gln Gln Asp Tyr Ser Ser Pro Tyr Thr
1               5

<210> SEQ ID NO 108
<211> LENGTH: 342
<212> TYPE: DNA
<213> ORGANISM: Mus sp.

<400> SEQUENCE: 108
cagatccact tggtgcagtc tggacctgaa ctgaagaagc ctggagagac agtcaagatc      60
tcctgcaagg cttctggata taccttcaca aactttggaa tgaactgggt gaagcaggct     120
ccaggaaagg gtttaaagtg gatgggctgg ataagtggct acactaggga gccaacatat     180
gctgctgact caagggacg atttgccatc tctttggaaa cctctgccag cactgcctat     240
ttgcagatca acgacctcaa aaatgaagac atggctacat atttctgtgc aagagacgtt     300
tttgactact ggggccaagg caccactctc acagtctcct ca                       342

<210> SEQ ID NO 109
<211> LENGTH: 114
<212> TYPE: PRT
<213> ORGANISM: Mus sp.

<400> SEQUENCE: 109

Gln Ile His Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Gly Met Asn Trp Val Lys Gln Ala Pro Gly Lys Gly Leu Lys Trp Met
        35                  40                  45

```
Gly Trp Ile Ser Gly Tyr Thr Arg Glu Pro Thr Tyr Ala Ala Asp Phe
    50                  55                  60

Lys Gly Arg Phe Ala Ile Ser Leu Glu Thr Ser Ala Ser Thr Ala Tyr
65                  70                  75                  80

Leu Gln Ile Asn Asp Leu Lys Asn Glu Asp Met Ala Thr Tyr Phe Cys
                85                  90                  95

Ala Arg Asp Val Phe Asp Tyr Trp Gly Gln Gly Thr Thr Leu Thr Val
            100                 105                 110

Ser Ser
```

<210> SEQ ID NO 110
<211> LENGTH: 5
<212> TYPE: PRT
<213> ORGANISM: Mus sp.

<400> SEQUENCE: 110

```
Asn Phe Gly Met Asn
1               5
```

<210> SEQ ID NO 111
<211> LENGTH: 17
<212> TYPE: PRT
<213> ORGANISM: Mus sp.

<400> SEQUENCE: 111

```
Trp Ile Ser Gly Tyr Thr Arg Glu Pro Thr Tyr Ala Ala Asp Phe Lys
1               5                   10                  15

Gly
```

<210> SEQ ID NO 112
<211> LENGTH: 5
<212> TYPE: PRT
<213> ORGANISM: Mus sp.

<400> SEQUENCE: 112

```
Asp Val Phe Asp Tyr
1               5
```

<210> SEQ ID NO 113
<211> LENGTH: 333
<212> TYPE: DNA
<213> ORGANISM: Mus sp.

<400> SEQUENCE: 113

```
gacattgtgc tgacccaatc tccagcttct ttggctgtgt ctctagggca gagggccacc      60
atttcctgca gagccagtga aagtgttgat aattatggct atagttttat gaactggttc     120
cagcagaaac caggacagcc acccaaactc ctcatctatc gtgcatccaa cctagaatct     180
gggatccctg ccaggttcag tggcagtggg tctaggacaa acttcaccct caccattaat     240
cctgtggagg ctgatgatgt tgcaacctat ttctgtcagc aaagtaatgc ggatccgacg     300
ttcggtggag gcaccaacct ggaaatcaaa cgg                                   333
```

<210> SEQ ID NO 114
<211> LENGTH: 111
<212> TYPE: PRT
<213> ORGANISM: Mus sp.

<400> SEQUENCE: 114

```
Asp Ile Val Leu Thr Gln Ser Pro Ala Ser Leu Ala Val Ser Leu Gly
1               5                   10                  15
```

```
Gln Arg Ala Thr Ile Ser Cys Arg Ala Ser Glu Ser Val Asp Asn Tyr
            20                  25                  30
Gly Tyr Ser Phe Met Asn Trp Phe Gln Gln Lys Pro Gly Gln Pro Pro
        35                  40                  45
Lys Leu Leu Ile Tyr Arg Ala Ser Asn Leu Glu Ser Gly Ile Pro Ala
 50                  55                  60
Arg Phe Ser Gly Ser Gly Ser Arg Thr Asn Phe Thr Leu Thr Ile Asn
 65                  70                  75                  80
Pro Val Glu Ala Asp Asp Val Ala Thr Tyr Phe Cys Gln Gln Ser Asn
                 85                  90                  95
Ala Asp Pro Thr Phe Gly Gly Gly Thr Asn Leu Glu Ile Lys Arg
            100                 105                 110

<210> SEQ ID NO 115
<211> LENGTH: 15
<212> TYPE: PRT
<213> ORGANISM: Mus sp.

<400> SEQUENCE: 115

Arg Ala Ser Glu Ser Val Asp Asn Tyr Gly Tyr Ser Phe Met Asn
 1               5                   10                  15

<210> SEQ ID NO 116
<211> LENGTH: 7
<212> TYPE: PRT
<213> ORGANISM: Mus sp.

<400> SEQUENCE: 116

Arg Ala Ser Asn Leu Glu Ser
 1               5

<210> SEQ ID NO 117
<211> LENGTH: 8
<212> TYPE: PRT
<213> ORGANISM: Mus sp.

<400> SEQUENCE: 117

Gln Gln Ser Asn Ala Asp Pro Thr
 1               5

<210> SEQ ID NO 118
<211> LENGTH: 1335
<212> TYPE: DNA
<213> ORGANISM: Artificial Sequence
<220> FEATURE:
<223> OTHER INFORMATION: 7A4-IgG1 D265A chimeric antibody heavy chain
      full length DNA sequence

<400> SEQUENCE: 118
cagatccact tggtgcagtc tggacctgaa ctgaagaagc ctggagagac agtcaagatc      60
tcctgcaagg cttctggata taccttcaca aactttggaa tgaactgggt gaagcaggct     120
ccaggaaagg gtttaaagtg gatgggctgg ataagtggct acactaggga gccaacatat     180
gctgctgact caagggacg atttgccatc tctttggaaa cctctgccag cactgcctat     240
ttgcagatca cgacctcaa aaatgaagac atggctacat atttctgtgc aagagacgtt     300
tttgactact ggggccaagg caccactctc acagtctcga gcgcctccac taagggccca     360
tccgtgttcc ctctggcacc ctccagcaag agcacaagcg gaggcaccgc cgcactgggc     420
tgcctcgtga aggactactt cccagaaccc gtgaccgtca gctggaatag cggcgctctg     480
```

```
accagcggag tccacacttt ccccgcagtg ctgcagtcca gcggcctgta cagcctgagc    540
agcgtggtca ctgtgccaag cagcagcctg ggcactcaga cctacatctg caacgtcaac    600
cacaagccca gcaacacaaa ggtggacaag aaggtcgagc ccaagtcctg cgataagacc    660
cacacctgcc ctccatgtcc cgcccccgag ctgctgggag acccagcgt cttcctgttt    720 ccccccaagc caaaggacac cctgatgatc agcaggaccc ccgaagtgac ctgcgtcgtg    780
gtggccgtga gccacgaaga tcccgaggtg aagttcaact ggtacgtgga cggcgtggaa    840
gtgcacaacg ccaagacaaa acccagggag gagcagtatg ccagcaccta cagggtcgtg    900
agcgtcctga ccgtgctgca ccaagactgg ctgaacggca aggagtataa gtgcaaggtg    960
agcaacaagg cactgcccgc ccccatcgag aagaccattt ccaaggccaa ggggcaacct   1020
agggagccac aggtctacac tctgccccct agcagggacg agctgaccaa gaaccaggtc   1080
tccctgactt gcctggtgaa ggggttttat cccagcgaca tcgccgtcga gtgggagagc   1140
aatggccagc ccgaaaacaa ctacaagacc acaccccctg tgctggacag cgacggcagc   1200
ttctttctgt atagcaaact gacagtggat aagagcagat ggcagcaggg caacgtgttc   1260
tcctgctccg tgatgcacga ggccctgcac aatcactaca cccagaagtc cctgagcctg   1320 tccccccggaa aatga                                                   1335
```

<210> SEQ ID NO 119
<211> LENGTH: 444
<212> TYPE: PRT
<213> ORGANISM: Artificial Sequence
<220> FEATURE:
<223> OTHER INFORMATION: 7A4-IgG1 D265A chimeric antibody heavy chain
      full length protein sequence

<400> SEQUENCE: 119

```
Gln Ile His Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Gly Met Asn Trp Val Lys Gln Ala Pro Gly Lys Gly Leu Lys Trp Met
        35                  40                  45

Gly Trp Ile Ser Gly Tyr Thr Arg Glu Pro Thr Tyr Ala Ala Asp Phe
    50                  55                  60

Lys Gly Arg Phe Ala Ile Ser Leu Glu Thr Ser Ala Ser Thr Ala Tyr
65                  70                  75                  80

Leu Gln Ile Asn Asp Leu Lys Asn Glu Asp Met Ala Thr Tyr Phe Cys
                85                  90                  95

Ala Arg Asp Val Phe Asp Tyr Trp Gly Gln Gly Thr Thr Leu Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205
```

Asp Lys Lys Val Glu Pro Lys Ser Cys Asp Lys Thr His Thr Cys Pro
            210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Ala Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 120
<211> LENGTH: 1323
<212> TYPE: DNA
<213> ORGANISM: Artificial Sequence
<220> FEATURE:
<223> OTHER INFORMATION: 7A4-IgG4 F234A L235A chimeric antibody heavy
      chain full length DNA sequence

<400> SEQUENCE: 120
cagatccact tggtgcagtc tggacctgaa ctgaagaagc tggagagaca gtcaagatc        60 tcctgcaagg cttctggata ccttcaca aactttggaa tgaactgggt gaagcaggct       120
ccaggaaagg gtttaaagtg gatgggctgg ataagtggct acactaggga gccaacatat     180
gctgctgact tcaagggacg atttgccatc tctttggaaa cctctgccag cactgcctat     240
ttgcagatca cgaccctcaa aaatgaagac atggctacat atttctgtgc aagagacgtt     300
tttgactact ggggccaagg caccactctc acagtctcga gcgcctccac caagggaccc     360
agcgtgtttc ccctggcccc ctgttccaga tccacctccg aaagcacagc cgctctcggc     420
tgcctggtca aggattactt ccctgagccc gtgacagtct cctggaatag cggcgctctg     480
acctccggcg tgcataccct ccctgctgtg ctgcaatcct ccggactgta cagcctgagc     540
agcgtggtca ccgtgccttc ctccagcctg gaaccaaaaa cctacacatg caacgtggac     600
cacaagccca gcaacaccaa gtggacaag aggtggagt ccaagtacgg accccttgt        660

```
cctccctgcc ctgctcctga agccgctgga ggacctagcg tgttcctgtt tccccccaag    720
cccaaggaca ccctcatgat ctccaggacc cccgaggtga cctgtgtcgt ggtggacgtg    780
agccaagagg accccgaggt gcagttcaac tggtacgtgg atggcgtcga ggtccataac    840
gccaagacca agcctaggga ggagcagttc aacagcacct acagagtggt gagcgtcctg    900
accgtgctcc accaagactg gctgaacggc aaggaataca agtgcaaggt ctccaacaag    960
ggactccctt cctccatcga aagaccatc agcaaggcca agggccagcc cagagaaccc   1020
caagtctaca cactgccccc cagccaagag gaaatgacca gaaccaggt gagcctgacc    1080 tgcctggtga aaggcttcta ccccagcgac attgctgtcg aatgggagag caacggccaa   1140
cccgagaaca actacaagac cacccccct gtgctcgaca gcgacggctc cttcttcctc    1200
tacagcaggc tgacagtgga caagtccagg tggcaagagg gcaatgtctt cagctgtagc    1260
gtcatgcacg aggccctcca caaccactac acccagaaga gcctgtccct ctccctgggc   1320
tga                                                                 1323
```

<210> SEQ ID NO 121
<211> LENGTH: 440
<212> TYPE: PRT
<213> ORGANISM: Artificial Sequence
<220> FEATURE:
<223> OTHER INFORMATION: 7A4-IgG4 F234A L235A chimeric antibody heavy
      chain full length protein sequence

<400> SEQUENCE: 121

```
Gln Ile His Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Gly Met Asn Trp Val Lys Gln Ala Pro Gly Lys Gly Leu Lys Trp Met
        35                  40                  45

Gly Trp Ile Ser Gly Tyr Thr Arg Glu Pro Thr Tyr Ala Ala Asp Phe
    50                  55                  60

Lys Gly Arg Phe Ala Ile Ser Leu Glu Thr Ser Ala Ser Thr Ala Tyr
65                  70                  75                  80

Leu Gln Ile Asn Asp Leu Lys Asn Glu Asp Met Ala Thr Tyr Phe Cys
                85                  90                  95

Ala Arg Asp Val Phe Asp Tyr Trp Gly Gln Gly Thr Thr Leu Thr Val
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
    210                 215                 220

Ala Pro Glu Ala Ala Gly Gly Pro Ser Val Phe Leu Phe Pro Pro Lys
225                 230                 235                 240
```

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly
        435                 440

<210> SEQ ID NO 122
<211> LENGTH: 654
<212> TYPE: DNA
<213> ORGANISM: Artificial Sequence
<220> FEATURE:
<223> OTHER INFORMATION: 7A4 chimeric antibody light chain full length
      DNA sequence

<400> SEQUENCE: 122
gacattgtgc tgacccaatc tccagcttct ttggctgtgt ctctagggca gagggccacc      60
atttcctgca gagccagtga aagtgttgat aattatggct atagttttat gaactggttc     120
cagcagaaac aggacagcc acccaaactc ctcatctatc gtgcatccaa cctagaatct     180
gggatccctg ccaggttcag tggcagtggg tctaggacaa acttcaccct caccattaat     240
cctgtggagg ctgatgatgt tgcaacctat ttctgtcagc aaagtaatgc ggatccgacg     300
ttcggtggag gcaccaacct ggaaatcaaa cgtacggtgg ccgcaccaag cgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agctttaaca gaggcgagtg ctga           654

<210> SEQ ID NO 123
<211> LENGTH: 217
<212> TYPE: PRT
<213> ORGANISM: Artificial Sequence
<220> FEATURE:

<223> OTHER INFORMATION: 7A4 chimeric antibody light chain full length
      protein sequence

<400> SEQUENCE: 123

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Tyr Ser Phe Met Asn Trp Phe Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asn Phe Thr Leu Thr Ile Asn
65                  70                  75                  80

Pro Val Glu Ala Asp Asp Val Ala Thr Tyr Phe Cys Gln Gln Ser Asn
                85                  90                  95

Ala Asp Pro Thr Phe Gly Gly Gly Thr Asn Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 124
<211> LENGTH: 1353
<212> TYPE: DNA
<213> ORGANISM: Artificial Sequence
<220> FEATURE:
<223> OTHER INFORMATION: 13F1-IgG1 D265A chimeric antibody heavy chain
      full length DNA sequence

<400> SEQUENCE: 124

```
gatgtgcagc ttcaggagtc gggacctggc ctggtgaaac cttctcagtc tctgtccctc      60
acctgcactg tcactggcta ctcaatcacc agtgattatg cctggaactg gatccggcag     120
tttccaggaa accaactgga gtggatggcc tacattagtt acagtggtta cactagctac     180
aacccatctc tcaaaagtcg aatctctatc actcgagaca catccaagaa ccagttcttc     240
ctgcagttga attctgtgac tactgaggac acagccacat attactgtgc aagatctctt     300
gactatgatt acggaactat ggactactgg ggtcaaggaa cctcagtcac cgtctcgagc     360
gcctccacta agggcccatc cgtgttccct ctggcaccct ccagcaagag cacaagcgga     420
ggcaccgccg cactgggctg cctcgtgaag gactacttcc cagaaccgt gaccgtcagc     480 tggaatagcg gcgctctgac cagcggagtc cacactttcc ccgcagtgct gcagtccagc     540
ggcctgtaca gcctgagcag cgtggtcact gtgccaagca gcagcctggg cactcagacc     600
tacatctgca acgtcaacca caagcccagc aacacaaagg tggacaagaa ggtcgagccc     660
```

```
aagtcctgcg ataagaccca cacctgccct ccatgtcccg ccccccgagct gctgggagga    720 cccagcgtct tcctgtttcc ccccaagcca aggacaccc tgatgatcag caggacccc    780 gaagtgacct gcgtcgtggt ggccgtgagc cacgaagatc ccgaggtgaa gttcaactgg    840
tacgtggacg gcgtggaagt gcacaacgcc aagacaaaac ccagggagga gcagtatgcc    900
agcacctaca gggtcgtgag cgtcctgacc gtgctgcacc aagactggct gaacggcaag    960
gagtataagt gcaaggtgag caacaaggca ctgcccgccc ccatcgagaa gaccatttcc   1020
aaggccaagg gcaacctag ggagccacag gtctacactc tgcccctag cagggacgag   1080 ctgaccaaga accaggtctc cctgacttgc ctggtgaagg ggttttatcc cagcgacatc   1140
gccgtcgagt gggagagcaa tggccagccc gaaaacaact acaagaccac cccccctgtg   1200
ctggacagcg acggcagctt ctttctgtat agcaaactga cagtggataa gagcagatgg   1260
cagcagggca acgtgttctc ctgctccgtg atgcacgagg ccctgcacaa tcactacacc   1320
cagaagtccc tgagcctgtc ccccggaaaa tga                                1353
```

<210> SEQ ID NO 125
<211> LENGTH: 450
<212> TYPE: PRT
<213> ORGANISM: Artificial Sequence
<220> FEATURE:
<223> OTHER INFORMATION: 13F1-IgG1 D265A chimeric antibody heavy chain
      full length protein sequence

<400> SEQUENCE: 125

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Gln Leu Glu Trp
            35                  40                  45

Met Ala Tyr Ile Ser Tyr Ser Gly Tyr Thr Ser Tyr Asn Pro Ser Leu
        50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Leu Asp Tyr Asp Tyr Gly Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
```

```
                225                 230                 235                 240
Pro Ser Val Phe Leu Phe Pro Lys Pro Lys Asp Thr Leu Met Ile
                245                 250                 255
Ser Arg Thr Pro Glu Val Thr Cys Val Val Val Ala Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Ala Ser Thr Tyr Arg
                290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
    450

<210> SEQ ID NO 126
<211> LENGTH: 1341
<212> TYPE: DNA
<213> ORGANISM: Artificial Sequence
<220> FEATURE:
<223> OTHER INFORMATION: 13F1-IgG4 F234A L235A chimeric antibody heavy
      chain full length DNA sequence

<400> SEQUENCE: 126
gatgtgcagc ttcaggagtc gggacctggc ctggtgaaac cttctcagtc tctgtccctc      60
acctgcactg tcactggcta tcaatcacc agtgattatg cctggaactg gatccggcag     120
tttccaggaa accaactgga gtggatggcc tacattagtt acagtggtta cactagctac     180
aacccatctc tcaaaagtcg aatctctatc actcgagaca catccaagaa ccagttcttc     240
ctgcagttga attctgtgac tactgaggac acagccacat attactgtgc aagatctctt     300
gactatgatt acggaactat ggactactgg ggtcaaggaa cctcagtcac cgtctcgagc     360
gcctccacca agggacccag cgtgtttccc ctggcccct gttccagatc cacctccgaa      420
agcacagccg ctctcggctg cctggtcaag gattacttcc ctgagccgt gacagtctcc      480 tggaatagcg gcgctctgac ctccggcgtg cataccttcc ctgctgtgct gcaatcctcc     540
ggactgtaca gcctgagcag cgtggtcacc gtgccttcct ccagcctggg aaccaaaacc     600
tacacatgca acgtggacca caagcccagc aacaccaaag tggacaagag ggtggagtcc     660
aagtacggac ccccttgtcc tccctgccct gctcctgaag ccgctggagg acctagcgtg     720
```

```
ttcctgtttc cccccaagcc caaggacacc ctcatgatct ccaggacccc cgaggtgacc    780
tgtgtcgtgg tggacgtgag ccaagaggac cccgaggtgc agttcaactg gtacgtggat    840
ggcgtcgagg tccataacgc caagaccaag cctagggagg agcagttcaa cagcacctac    900
agagtggtga gcgtcctgac cgtgctccac caagactggc tgaacggcaa ggaatacaag    960
tgcaaggtct ccaacaaggg actcccttcc tccatcgaga agaccatcag caaggccaag   1020
ggccagccca gagaaccccca agtctacaca ctgcccccca gccaagagga atgaccaag    1080 aaccaggtga gcctgacctg cctggtgaaa ggcttctacc ccagcgacat tgctgtcgaa   1140
tgggagagca acggccaacc cgagaacaac tacaagacca ccccccctgt gctcgacagc   1200
gacggctcct tcttcctcta cagcaggctg acagtggaca agtccaggtg gcaagagggc   1260
aatgtcttca gctgtagcgt catgcacgag gccctccaca accactacac ccagaagagc   1320
ctgtccctct ccctgggctg a                                              1341
```

<210> SEQ ID NO 127
<211> LENGTH: 446
<212> TYPE: PRT
<213> ORGANISM: Artificial Sequence
<220> FEATURE:
<223> OTHER INFORMATION: 13F1-IgG4 F234A L235A chimeric antibody heavy
      chain full length protein sequence

<400> SEQUENCE: 127

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Gln Leu Glu Trp
        35                  40                  45

Met Ala Tyr Ile Ser Tyr Ser Gly Tyr Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Leu Asp Tyr Asp Tyr Gly Thr Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
```

245                 250                 255
Pro Glu Val Thr Cys Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 128
<211> LENGTH: 642
<212> TYPE: DNA
<213> ORGANISM: Artificial Sequence
<220> FEATURE:
<223> OTHER INFORMATION: 13F1 chimeric antibody light chain full length
      DNA sequence

<400> SEQUENCE: 128
caaattgttc tctcccagtc tccagcaatc ctgtctgcat ctccagggga gaaggtcaca      60
atgacctgca gggccaactc aagtgtaagt tccatgcact ggtaccagca gaagccagga     120 tcctccccg aaccctggat ttatgccatt ccaacctgg cttttggagt ccctactcgc       180
ttcagtggca gtgggtctgg gacctcttac tctctcacaa tcagcagagt ggaggctgaa     240
gatgctgcca cttatttctg ccagcagtgg agtagtagac acccacgtt cggagggggg      300 accaagctgg aaataaaacg tacggtggcc gcaccaagcg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag      480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag ctttaacaga ggcgagtgct ga                        642

<210> SEQ ID NO 129
<211> LENGTH: 213
<212> TYPE: PRT
<213> ORGANISM: Artificial Sequence
<220> FEATURE:
<223> OTHER INFORMATION: 13F1 chimeric antibody light chain full length
      protein sequence

<400> SEQUENCE: 129

Gln Ile Val Leu Ser Gln Ser Pro Ala Ile Leu Ser Ala Ser Pro Gly
1               5                   10                  15

Glu Lys Val Thr Met Thr Cys Arg Ala Asn Ser Ser Val Ser Ser Met
            20                  25                  30

His Trp Tyr Gln Gln Lys Pro Gly Ser Ser Pro Glu Pro Trp Ile Tyr
        35                  40                  45

Ala Ile Ser Asn Leu Ala Phe Gly Val Pro Thr Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys Gln Gln Trp Ser Ser Arg Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 130
<211> LENGTH: 342
<212> TYPE: DNA
<213> ORGANISM: Artificial Sequence
<220> FEATURE:
<223> OTHER INFORMATION: Humanized 7A4 antibody heavy chain variable
      region DNA sequence

<400> SEQUENCE: 130
cagatccagc tggtgcagag cgggagcgaa ctgaaaaaac ctggggcaag cgtgaaagtc      60
tcatgtaaag caagcggcta cacatttacc aacttcggca tgaattgggt caggcaggca     120
ccaggacagg gactgaagtg gatggggtgg atctccggat acactcggga gcctacctat     180
gccgctgact tcaaagggag atttgtgatc agtctggata catcagtcag cactgcttac     240
ctgcagatta gctccctgaa ggcagaagac acagccgtgt actattgcgc acgggacgtc     300
tttgattatt ggggacaggg caccctggtg acagtctcga gc                        342

<210> SEQ ID NO 131
<211> LENGTH: 114
<212> TYPE: PRT
<213> ORGANISM: Artificial Sequence
<220> FEATURE:
<223> OTHER INFORMATION: Humanized 7A4 antibody heavy chain variable
      region protein sequence

<400> SEQUENCE: 131

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Phe
            20                  25                  30

Gly Met Asn Trp Val Arg Gln Ala Pro Gly Gln Gly Leu Lys Trp Met
        35                  40                  45

Gly Trp Ile Ser Gly Tyr Thr Arg Glu Pro Thr Tyr Ala Ala Asp Phe
    50                  55                  60

Lys Gly Arg Phe Val Ile Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Val Phe Asp Tyr Trp Gly Gln Gly Thr Leu Val Thr Val
            100                 105                 110

Ser Ser

<210> SEQ ID NO 132
<211> LENGTH: 330
<212> TYPE: DNA
<213> ORGANISM: Artificial Sequence
<220> FEATURE:
<223> OTHER INFORMATION: Humanized 7A4 antibody light chain variable
      region DNA sequence

<400> SEQUENCE: 132
gacatcgtcc tgacacagtc tcccgcatcc ctggccgtct ctcccggaca gcgagcaaca      60
atcacctgcc gagcatctga aagcgtggat aactacgggt atagcttcat gaattggttt     120
cagcagaagc ccggacagcc ccctaaactg ctgatctaca gggcaagtaa cctggagtca     180
ggagtgccag cacgattcag cggatccggg tctagaacag actttaccct gacaattaac     240
cccgtcgaag ccaacgatac cgctaattac tattgccagc agtctaatgc tgaccctact     300
ttcggacagg gcaccaagct ggagatcaaa                                      330

<210> SEQ ID NO 133
<211> LENGTH: 110
<212> TYPE: PRT
<213> ORGANISM: Artificial Sequence
<220> FEATURE:
<223> OTHER INFORMATION: Humanized 7A4 antibody light chain variable
      region protein sequence

<400> SEQUENCE: 133

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met Asn Trp Phe Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asn Asp Thr Ala Asn Tyr Tyr Cys Gln Gln Ser Asn
                85                  90                  95

Ala Asp Pro Thr Phe Gly Gln Gly Thr Lys Leu Glu Ile Lys
            100                 105                 110

<210> SEQ ID NO 134
<211> LENGTH: 1335
<212> TYPE: DNA
<213> ORGANISM: Artificial Sequence
<220> FEATURE:
<223> OTHER INFORMATION: Humanized 7A4-IgG1 D265A antibody heavy chain full length DNA sequence

<400> SEQUENCE: 134

```
cagatccagc tggtgcagag cgggagcgaa ctgaaaaaac ctggggcaag cgtgaaagtc    60
tcatgtaaag caagcggcta cacatttacc aacttcggca tgaattgggt caggcaggca   120
ccaggacagg gactgaagtg gatggggtgg atctccggat acactcggga gcctacctat   180
gccgctgact tcaaagggag atttgtgatc agtctggata catcagtcag cactgcttac   240
ctgcagatta gctccctgaa ggcagaagac acagccgtgt actattgcgc acggacgtc    300
tttgattatt ggggacaggg caccctggtg acagtctcga gcgcctccac taagggccca   360
tccgtgttcc ctctggcacc ctccagcaag agcacaagcg gaggcaccgc cgcactgggc   420
tgcctcgtga aggactactt cccagaaccc gtgaccgtca gctggaatag cggcgctctg   480
accagcggag tccacacttt ccccgcagtg ctgcagtcca gcggcctgta cagcctgagc   540
agcgtggtca ctgtgccaag cagcagcctg ggcactcaga cctacatctg caacgtcaac   600
cacaagccca gcaacacaaa ggtggacaag aaggtcgagc ccaagtcctg cgataagacc   660
cacacctgcc ctccatgtcc cgcccccgag ctgctgggag acccagcgt cttcctgttt    720
ccccccaagc caaggacac cctgatgatc agcaggaccc ccgaagtgac ctgcgtcgtg    780
gtggccgtga gccacgaaga tcccgaggtg aagttcaact ggtacgtgga cggcgtggaa   840
gtgcacaacg ccaagacaaa acccagggag gagcagtata acagcaccta cagggtcgtg   900
agcgtcctga ccgtgctgca ccaagactgg ctgaacggca aggagtataa gtgcaaggtg   960
agcaacaagg cactgcccgc ccccatcgag aagaccattt ccaaggccaa ggggcaacct  1020
agggagccac aggtctacac tctgcccct agcaggacg agctgaccaa gaaccaggtc  1080
tccctgactt gcctggtgaa ggggttttat cccagcgaca tcgccgtcga gtgggagagc  1140
aatggccagc cgaaaacaa ctacaagacc acaccccctg tgctggacag cgacggcagc  1200
ttctttctgt atagcaaact gacagtggat aagagcagat ggcagcaggg caacgtgttc  1260
tcctgctccg tgatgcacga ggccctgcac aatcactaca cccagaagtc cctgagcctg  1320
tcccccggaa aatga                                                  1335
```

<210> SEQ ID NO 135
<211> LENGTH: 444
<212> TYPE: PRT
<213> ORGANISM: Artificial Sequence
<220> FEATURE:
<223> OTHER INFORMATION: Humanized 7A4-IgG1 D265A antibody heavy chain full length protein sequence

<400> SEQUENCE: 135

```
Gln Ile Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Phe
            20                  25                  30

Gly Met Asn Trp Val Arg Gln Ala Pro Gly Gln Gly Leu Lys Trp Met
        35                  40                  45

Gly Trp Ile Ser Gly Tyr Thr Arg Glu Pro Thr Tyr Ala Ala Asp Phe
    50                  55                  60
```

```
Lys Gly Arg Phe Val Ile Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Asp Val Phe Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Ala Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 136
<211> LENGTH: 1323
<212> TYPE: DNA
<213> ORGANISM: Artificial Sequence
<220> FEATURE:
<223> OTHER INFORMATION: Humanized 7A4-IgG4 F234A L235A antibody heavy
``` chain full length DNA sequence

<400> SEQUENCE: 136

| | | | | | |
|---|---|---|---|---|---|
| cagatccagc | tggtgcagag | cgggagcgaa | ctgaaaaaac | ctggggcaag | cgtgaaagtc | 60 |
| tcatgtaaag | caagcggcta | cacatttacc | aacttcggca | tgaattgggt | caggcaggca | 120 |
| ccaggacagg | gactgaagtg | gatggggtgg | atctccggat | acactcggga | gcctacctat | 180 |
| gccgctgact | tcaaagggag | atttgtgatc | agtctggata | catcagtcag | cactgcttac | 240 |
| ctgcagatta | gctccctgaa | ggcagaagac | acagccgtgt | actattgcgc | acgggacgtc | 300 |
| tttgattatt | ggggacaggg | caccctggtg | acagtctcga | gcgcctccac | caagggaccc | 360 |
| agcgtgtttc | ccctggcccc | ctgttccaga | tccacctccg | aaagcacagc | cgctctcggc | 420 |
| tgcctggtca | aggattactt | ccctgagccc | gtgacagtct | cctggaatag | cggcgctctg | 480 |
| acctccggcg | tgcatacctt | ccctgctgtg | ctgcaatcct | ccggactgta | cagcctgagc | 540 |
| agcgtggtca | ccgtgccttc | ctccagcctg | gaaccaaaaa | cctacacatg | caacgtggac | 600 |
| cacaagccca | gcaacaccaa | agtggacaag | agggtggagt | ccaagtacgg | acccccttgt | 660 |
| cctcccctgcc | ctgctcctga | agccgctgga | ggacctagcg | tgttcctgtt | tccccccaag | 720 |
| cccaaggaca | ccctcatgat | ctccaggacc | cccgaggtga | cctgtgtcgt | ggtggacgtg | 780 |
| agccaagagg | accccgaggt | gcagttcaac | tggtacgtgg | atggcgtcga | ggtccataac | 840 |
| gccaagacca | gcctaggga | ggagcagttc | aacagcacct | acagagtggt | gagcgtcctg | 900 |
| accgtgctcc | accaagactg | gctgaacggc | aaggaataca | agtgcaaggt | ctccaacaag | 960 |
| ggactcccctt | cctccatcga | gaagaccatc | agcaaggcca | agggccagcc | cagagaaccc | 1020 |
| caagtctaca | cactgccccc | cagccaagag | gaaatgacca | agaaccaggt | gagcctgacc | 1080 |
| tgcctggtga | aaggcttcta | ccccagcgac | attgctgtcg | aatgggagag | caacggccaa | 1140 |
| cccgagaaca | actacaagac | cacccccccct | gtgctcgaca | gcgacggctc | cttcttcctc | 1200 |
| tacagcaggc | tgacagtgga | caagtccagg | tggcaagagg | gcaatgtctt | cagctgtagc | 1260 |
| gtcatgcacg | aggccctcca | caaccactac | acccagaaga | gcctgtccct | ctccctgggc | 1320 |
| tga | | | | | | 1323 |

<210> SEQ ID NO 137
<211> LENGTH: 440
<212> TYPE: PRT
<213> ORGANISM: Artificial Sequence
<220> FEATURE:
<223> OTHER INFORMATION: Humanized 7A4-IgG4 F234A L235A antibody heavy
      chain full length protein sequence

<400> SEQUENCE: 137

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Phe
            20                  25                  30

Gly Met Asn Trp Val Arg Gln Ala Pro Gly Gln Gly Leu Lys Trp Met
        35                  40                  45

Gly Trp Ile Ser Gly Tyr Thr Arg Glu Pro Thr Tyr Ala Ala Asp Phe
    50                  55                  60

Lys Gly Arg Phe Val Ile Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

| Ala | Arg | Asp | Val | Phe | Asp | Tyr | Trp | Gly | Gln | Gly | Thr | Leu | Val | Thr | Val |
|---|---|---|---|---|---|---|---|---|---|---|---|---|---|---|---|
| | | | 100 | | | | 105 | | | | 110 | | | | |

| Ser | Ser | Ala | Ser | Thr | Lys | Gly | Pro | Ser | Val | Phe | Pro | Leu | Ala | Pro | Cys |
|---|---|---|---|---|---|---|---|---|---|---|---|---|---|---|---|
| | 115 | | | | 120 | | | | | 125 | | | | | |

| Ser | Arg | Ser | Thr | Ser | Glu | Ser | Thr | Ala | Ala | Leu | Gly | Cys | Leu | Val | Lys |
|---|---|---|---|---|---|---|---|---|---|---|---|---|---|---|---|
| | 130 | | | | | 135 | | | | 140 | | | | | |

| Asp | Tyr | Phe | Pro | Glu | Pro | Val | Thr | Val | Ser | Trp | Asn | Ser | Gly | Ala | Leu |
|---|---|---|---|---|---|---|---|---|---|---|---|---|---|---|---|
| 145 | | | | | 150 | | | | 155 | | | | | 160 | |

| Thr | Ser | Gly | Val | His | Thr | Phe | Pro | Ala | Val | Leu | Gln | Ser | Ser | Gly | Leu |
|---|---|---|---|---|---|---|---|---|---|---|---|---|---|---|---|
| | | | | 165 | | | | | 170 | | | | 175 | | |

| Tyr | Ser | Leu | Ser | Ser | Val | Val | Thr | Val | Pro | Ser | Ser | Ser | Leu | Gly | Thr |
|---|---|---|---|---|---|---|---|---|---|---|---|---|---|---|---|
| | | 180 | | | | | 185 | | | | | 190 | | | |

| Lys | Thr | Tyr | Thr | Cys | Asn | Val | Asp | His | Lys | Pro | Ser | Asn | Thr | Lys | Val |
|---|---|---|---|---|---|---|---|---|---|---|---|---|---|---|---|
| | | 195 | | | | 200 | | | | | 205 | | | | |

| Asp | Lys | Arg | Val | Glu | Ser | Lys | Tyr | Gly | Pro | Pro | Cys | Pro | Pro | Cys | Pro |
|---|---|---|---|---|---|---|---|---|---|---|---|---|---|---|---|
| 210 | | | | | 215 | | | | | 220 | | | | | |

| Ala | Pro | Glu | Ala | Ala | Gly | Gly | Pro | Ser | Val | Phe | Leu | Phe | Pro | Pro | Lys |
|---|---|---|---|---|---|---|---|---|---|---|---|---|---|---|---|
| 225 | | | | | 230 | | | | | 235 | | | | | 240 |

| Pro | Lys | Asp | Thr | Leu | Met | Ile | Ser | Arg | Thr | Pro | Glu | Val | Thr | Cys | Val |
|---|---|---|---|---|---|---|---|---|---|---|---|---|---|---|---|
| | | | | 245 | | | | | 250 | | | | | 255 | |

| Val | Val | Asp | Val | Ser | Gln | Glu | Asp | Pro | Glu | Val | Gln | Phe | Asn | Trp | Tyr |
|---|---|---|---|---|---|---|---|---|---|---|---|---|---|---|---|
| | | | 260 | | | | | 265 | | | | | 270 | | |

| Val | Asp | Gly | Val | Glu | Val | His | Asn | Ala | Lys | Thr | Lys | Pro | Arg | Glu | Glu |
|---|---|---|---|---|---|---|---|---|---|---|---|---|---|---|---|
| | | 275 | | | | | 280 | | | | | 285 | | | |

| Gln | Phe | Asn | Ser | Thr | Tyr | Arg | Val | Val | Ser | Val | Leu | Thr | Val | Leu | His |
|---|---|---|---|---|---|---|---|---|---|---|---|---|---|---|---|
| | 290 | | | | | 295 | | | | | 300 | | | | |

| Gln | Asp | Trp | Leu | Asn | Gly | Lys | Glu | Tyr | Lys | Cys | Lys | Val | Ser | Asn | Lys |
|---|---|---|---|---|---|---|---|---|---|---|---|---|---|---|---|
| 305 | | | | | 310 | | | | | 315 | | | | | 320 |

| Gly | Leu | Pro | Ser | Ser | Ile | Glu | Lys | Thr | Ile | Ser | Lys | Ala | Lys | Gly | Gln |
|---|---|---|---|---|---|---|---|---|---|---|---|---|---|---|---|
| | | | | 325 | | | | | 330 | | | | | 335 | |

| Pro | Arg | Glu | Pro | Gln | Val | Tyr | Thr | Leu | Pro | Pro | Ser | Gln | Glu | Glu | Met |
|---|---|---|---|---|---|---|---|---|---|---|---|---|---|---|---|
| | | | 340 | | | | | 345 | | | | | 350 | | |

| Thr | Lys | Asn | Gln | Val | Ser | Leu | Thr | Cys | Leu | Val | Lys | Gly | Phe | Tyr | Pro |
|---|---|---|---|---|---|---|---|---|---|---|---|---|---|---|---|
| | | 355 | | | | | 360 | | | | | 365 | | | |

| Ser | Asp | Ile | Ala | Val | Glu | Trp | Glu | Ser | Asn | Gly | Gln | Pro | Glu | Asn | Asn |
|---|---|---|---|---|---|---|---|---|---|---|---|---|---|---|---|
| 370 | | | | | 375 | | | | | 380 | | | | | |

| Tyr | Lys | Thr | Thr | Pro | Pro | Val | Leu | Asp | Ser | Asp | Gly | Ser | Phe | Phe | Leu |
|---|---|---|---|---|---|---|---|---|---|---|---|---|---|---|---|
| 385 | | | | | 390 | | | | | 395 | | | | | 400 |

| Tyr | Ser | Arg | Leu | Thr | Val | Asp | Lys | Ser | Arg | Trp | Gln | Glu | Gly | Asn | Val |
|---|---|---|---|---|---|---|---|---|---|---|---|---|---|---|---|
| | | | | 405 | | | | | 410 | | | | | 415 | |

| Phe | Ser | Cys | Ser | Val | Met | His | Glu | Ala | Leu | His | Asn | His | Tyr | Thr | Gln |
|---|---|---|---|---|---|---|---|---|---|---|---|---|---|---|---|
| | | | 420 | | | | | 425 | | | | | 430 | | |

| Lys | Ser | Leu | Ser | Leu | Ser | Leu | Gly |
|---|---|---|---|---|---|---|---|
| | | 435 | | | | 440 | |

<210> SEQ ID NO 138
<211> LENGTH: 654
<212> TYPE: DNA
<213> ORGANISM: Artificial Sequence
<220> FEATURE:
<223> OTHER INFORMATION: Humanized 7A4 antibody light chain full length
    DNA sequence

<400> SEQUENCE: 138
gacatcgtcc tgacacagtc tcccgcatcc ctggccgtct ctcccggaca gcgagcaaca    60

```
atcacctgcc gagcatctga aagcgtggat aactacgggt atagcttcat gaattggttt    120
cagcagaagc ccggacagcc ccctaaactg ctgatctaca gggcaagtaa cctggagtca    180
ggagtgccag cacgattcag cggatccggg tctagaacag actttaccct gacaattaac    240
cccgtcgaag ccaacgatac cgctaattac tattgccagc agtctaatgc tgaccctact    300
ttcggacagg gcaccaagct ggagatcaaa cgtacggtgg ccgcaccaag cgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agctttaaca gaggcgagtg ctga          654
```

<210> SEQ ID NO 139
<211> LENGTH: 217
<212> TYPE: PRT
<213> ORGANISM: Artificial Sequence
<220> FEATURE:
<223> OTHER INFORMATION: Humanized 7A4 antibody light chain full length
      protein sequence

<400> SEQUENCE: 139

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met Asn Trp Phe Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asn Asp Thr Ala Asn Tyr Tyr Cys Gln Gln Ser Asn
                85                  90                  95

Ala Asp Pro Thr Phe Gly Gln Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 140
<211> LENGTH: 360
<212> TYPE: DNA
<213> ORGANISM: Artificial Sequence
<220> FEATURE:

<223> OTHER INFORMATION: Humanized 13F1 antibody heavy chain variable
     region DNA sequence

<400> SEQUENCE: 140

```
caggtgcagc tgcaggagag cggacccgga ctggtgaagc ctagccagac actgagcctg    60
acttgtactg tgagcggata ttccattagc tccgactacg cttggaactg gatcaggcag   120
ccacctggca agggactgga gtggatggcc tacatttcct attctgggta caccagctat   180
aaccccagtc tgaaatcacg gatcacaatt agcagagaca cttccaagaa tcagttctct   240
ctgaaactgt ctagtgtgac tgccgctgat accgcagtct actattgcgc ccggtccctg   300
gactacgatt atggcacaat ggattattgg ggacagggca ccctggtgac agtctcgagc   360
```

<210> SEQ ID NO 141
<211> LENGTH: 120
<212> TYPE: PRT
<213> ORGANISM: Artificial Sequence
<220> FEATURE:
<223> OTHER INFORMATION: Humanized 13F1 antibody heavy chain variable
     region protein sequence

<400> SEQUENCE: 141

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Tyr Ala Trp Asn Trp Ile Arg Gln Pro Pro Gly Lys Gly Leu Glu Trp
        35                  40                  45

Met Ala Tyr Ile Ser Tyr Ser Gly Tyr Thr Ser Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Leu Asp Tyr Asp Tyr Gly Thr Met Asp Tyr Trp Gly Gln
            100                 105                 110

Gly Thr Leu Val Thr Val Ser Ser
        115                 120

<210> SEQ ID NO 142
<211> LENGTH: 318
<212> TYPE: DNA
<213> ORGANISM: Artificial Sequence
<220> FEATURE:
<223> OTHER INFORMATION: Humanized 13F1 antibody light chain variable
     region DNA sequence

<400> SEQUENCE: 142

```
gaaatcgtcc tgacccagag tcccgccacc ctgtcactga gccccggaga aagagccaca    60
ctgagttgta gagcaaatag cagcgtgagc tccatgcact ggtaccagca gaagcctgga   120
cagtccccag agccctggat ctatgccatt agcaacctgg ctttcggcgt gccagcaagg   180
ttttccggct ctgggagtgg aacagactac accctgacaa tctctagtct ggagcccgaa   240
gatttcgccg tctactattg ccagcagtgg tcaagccggc ccctactttt tggccagggg   300
accaagctgg agatcaag                                                 318
```

<210> SEQ ID NO 143
<211> LENGTH: 106
<212> TYPE: PRT

<213> ORGANISM: Artificial Sequence
<220> FEATURE:
<223> OTHER INFORMATION: Humanized 13F1 antibody light chain variable region protein sequence

<400> SEQUENCE: 143

Glu Ile Val Leu Thr Gln Ser Pro Ala Thr Leu Ser Leu Ser Pro Gly
1               5                   10                  15

Glu Arg Ala Thr Leu Ser Cys Arg Ala Asn Ser Ser Val Ser Ser Met
            20                  25                  30

His Trp Tyr Gln Gln Lys Pro Gly Gln Ser Pro Glu Pro Trp Ile Tyr
        35                  40                  45

Ala Ile Ser Asn Leu Ala Phe Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Arg Pro Pro Thr
                85                  90                  95

Phe Gly Gln Gly Thr Lys Leu Glu Ile Lys
            100                 105

<210> SEQ ID NO 144
<211> LENGTH: 1353
<212> TYPE: DNA
<213> ORGANISM: Artificial Sequence
<220> FEATURE:
<223> OTHER INFORMATION: Humanized 13F1-IgG1 D265A antibody heavy chain full length DNA sequence

<400> SEQUENCE: 144

```
caggtgcagc tgcaggagag cggacccgga ctggtgaagc ctagccagac actgagcctg      60
acttgtactg tgagcggata ttccattagc tccgactacg cttggaactg gatcaggcag     120
ccacctggca agggactgga gtggatggcc tacatttcct attctgggta caccagctat     180
aaccccagtc tgaaatcacg gatcacaatt agcagagaca cttccaagaa tcagttctct     240
ctgaaactgt ctagtgtgac tgccgctgat accgcagtct actattgcgc ccggtccctg     300
gactacgatt atggcacaat ggattattgg ggacagggca ccctggtgac agtctcgagc     360
gcctccacta agggcccatc cgtgttccct ctggcaccct ccagcaagag cacaagcgga     420
ggcaccgccg cactgggctg cctcgtgaag gactacttcc cagaacccgt gaccgtcagc     480
tggaatagcg gcgctctgac cagcggagtc cacactttcc ccgcagtgct gcagtccagc     540
ggcctgtaca gcctgagcag cgtggtcact gtgccaagca gcagcctggg cactcagacc     600
tacatctgca acgtcaacca caagcccagc aacacaaagg tggacaagaa ggtcgagccc     660
aagtcctgcg ataagaccca cacctgccct ccatgtcccg cccccgagct gctgggagga     720
cccagcgtct tcctgttccc ccccaagcca aggacacccc tgatgatcag caggacccca     780
gaagtgacct gcgtcgtggt ggccgtgagc acgaagatcc cgaggtgaa gttcaactgg     840
tacgtggacg gcgtggaagt gcacaacgcc aagacaaaac ccagggagga gcagtataac     900
agcacctaca gggtcgtgag cgtcctgacc gtgctgcacc aagactggct gaacggcaag     960
gagtataagt gcaaggtgag caacaaggca ctgcccgccc catcgagaa gaccatttcc    1020
aaggccaagg gcaacctag ggagccacag gtctacactc tgcccctag cagggacgag    1080
ctgaccaaga accaggtctc cctgacttgc ctggtgaagg gtttttatcc cagcgacatc    1140
gccgtcgagt gggagagcaa tggccagccc gaaaacaact acaagaccac accccctgtg    1200
```

-continued

```
ctggacagcg acggcagctt ctttctgtat agcaaactga cagtggataa gagcagatgg    1260
cagcagggca acgtgttctc ctgctccgtg atgcacgagg ccctgcacaa tcactacacc    1320
cagaagtccc tgagcctgtc ccccggaaaa tga                                 1353
```

<210> SEQ ID NO 145
<211> LENGTH: 450
<212> TYPE: PRT
<213> ORGANISM: Artificial Sequence
<220> FEATURE:
<223> OTHER INFORMATION: Humanized 13F1-IgG1 D265A antibody heavy chain
full length protein sequence

<400> SEQUENCE: 145

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Tyr Ala Trp Asn Trp Ile Arg Gln Pro Pro Gly Lys Gly Leu Glu Trp
        35                  40                  45

Met Ala Tyr Ile Ser Tyr Ser Gly Tyr Thr Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Leu Asp Tyr Asp Tyr Gly Thr Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ala Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 146
<211> LENGTH: 1341
<212> TYPE: DNA
<213> ORGANISM: Artificial Sequence
<220> FEATURE:
<223> OTHER INFORMATION: Humanized 13F1-IgG4 F234A L235A antibody heavy
      chain full length DNA sequence

<400> SEQUENCE: 146
caggtgcagc tgcaggagag cggacccgga ctggtgaagc ctagccagac actgagcctg      60
acttgtactg tgagcggata ttccattagc tccgactacg cttggaactg gatcaggcag     120
ccacctggca agggactgga gtggatggcc tacatttcct attctgggta caccagctat     180
aaccccagtc tgaaatcacg gatcacaatt agcagagaca cttccaagaa tcagttctct     240
ctgaaactgt ctagtgtgac tgccgctgat accgcagtct actattgcgc ccggtccctg     300
gactacgatt atggcacaat ggattattgg ggacagggca cctggtgac agtctcgagc     360 gcctccacca agggcccag cgtgtttccc ctggccccct gttccagatc cacctccgaa     420
agcacagccg ctctcggctg cctggtcaag gattacttcc ctgagcccgt gacagtctcc     480
tggaatagcg gcgctctgac ctccggcgtg catacctcc ctgctgtgct gcaatcctcc     540
ggactgtaca gcctgagcag cgtggtcacc gtgccttcct ccagcctggg aaccaaaacc     600
tacacatgca cgtggacca caagcccagc aacaccaaag tggacaagag ggtggagtcc     660
aagtacggac ccccttgtcc tcctgccct gctcctgaag ccgctggagg acctagcgtg     720
ttcctgtttc ccccaagcc caaggacacc ctcatgatct ccaggacccc cgaggtgacc     780
tgtgtcgtgg tggacgtgag ccaagaggac cccgaggtgc agttcaactg gtacgtggat     840
ggcgtcgagg tccataacgc caagaccaag cctaggagg agcagttcaa cagcacctac     900
agagtggtga gcgtcctgac cgtgctccac caagactggc tgaacggcaa ggaatacaag     960
tgcaaggtct ccaacaaggg actccccttcc tccatcgaga gaccatcag caaggccaag    1020 ggccagccca gaaacccca gtctacaca ctgcccccca gccaagagga atgaccaag      1080 aaccaggtga gcctgacctg cctggtgaaa ggcttctacc ccagcgacat tgctgtcgaa    1140
tgggagagca acggccaacc cgagaacaac tacaagacca ccccccctgt gctcgacagc    1200
gacggctcct tcttcctcta cagcaggctg acagtggaca gtccaggtg caagagggc      1260 aatgtcttca gctgtagcgt catgcacgag gccctccaca accactacac ccagaagagc    1320
```
ctgtccctct ccctgggctg a 1341

<210> SEQ ID NO 147
<211> LENGTH: 446
<212> TYPE: PRT
<213> ORGANISM: Artificial Sequence
<220> FEATURE:
<223> OTHER INFORMATION: Humanized 13F1-IgG4 F234A L235A antibody heavy
      chain full length protein sequence

<400> SEQUENCE: 147

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Tyr Ala Trp Asn Trp Ile Arg Gln Pro Pro Gly Lys Gly Leu Glu Trp
        35                  40                  45

Met Ala Tyr Ile Ser Tyr Ser Gly Tyr Thr Ser Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Leu Asp Tyr Asp Tyr Gly Thr Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
                420                 425                 430
His Asn His Tyr Thr Gln Lys Ser Leu Ser Leu Ser Leu Gly
                435                 440                 445

<210> SEQ ID NO 148
<211> LENGTH: 642
<212> TYPE: DNA
<213> ORGANISM: Artificial Sequence
<220> FEATURE:
<223> OTHER INFORMATION: Humanized 13F1 antibody light chain full length
      DNA sequence

<400> SEQUENCE: 148
gaaatcgtcc tgacccagag tcccgccacc ctgtcactga gccccggaga agagccaca       60 ctgagttgta gagcaaatag cagcgtgagc tccatgcact ggtaccagca gaagcctgga      120
cagtccccag agccctggat ctatgccatt agcaacctgg ctttcggcgt gccagcaagg      180 tttccggct ctgggagtgg aacagactac accctgacaa tctctagtct ggagcccgaa      240
gatttcgccg tctactattg ccagcagtgg tcaagccggc ccctactttt ggccagggg      300 accaagctgg agatcaagcg tacggtggcc gcaccaagcg tcttcatctt cccgccatct      360
gatgagcagt tgaaatctgg aactgcctct gttgtgtgcc tgctgaataa cttctatccc      420
agagaggcca agtacagtg gaaggtggat aacgccctcc aatcgggtaa ctcccaggag      480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttttaacaga ggcgagtgct ga                       642

<210> SEQ ID NO 149
<211> LENGTH: 213
<212> TYPE: PRT
<213> ORGANISM: Artificial Sequence
<220> FEATURE:
<223> OTHER INFORMATION: Humanized 13F1 antibody light chain full length
      protein sequence

<400> SEQUENCE: 149

Glu Ile Val Leu Thr Gln Ser Pro Ala Thr Leu Ser Leu Ser Pro Gly
1               5                   10                  15
Glu Arg Ala Thr Leu Ser Cys Arg Ala Asn Ser Ser Val Ser Ser Met
                20                  25                  30
His Trp Tyr Gln Gln Lys Pro Gly Gln Ser Pro Glu Pro Trp Ile Tyr
            35                  40                  45
Ala Ile Ser Asn Leu Ala Phe Gly Val Pro Ala Arg Phe Ser Gly Ser
        50                  55                  60
Gly Ser Gly Thr Asp Tyr Thr Leu Thr Ile Ser Ser Leu Glu Pro Glu
65                  70                  75                  80
Asp Phe Ala Val Tyr Tyr Cys Gln Gln Trp Ser Ser Arg Pro Pro Thr
```

```
            85                  90                  95
Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 150
<211> LENGTH: 330
<212> TYPE: PRT
<213> ORGANISM: Homo sapiens

<400> SEQUENCE: 150

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 151
<211> LENGTH: 326
<212> TYPE: PRT
<213> ORGANISM: Homo sapiens

<400> SEQUENCE: 151

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 152
<211> LENGTH: 110
<212> TYPE: PRT
<213> ORGANISM: Artificial Sequence
<220> FEATURE:
<223> OTHER INFORMATION: 7A4D Humanized Light chain variable

<400> SEQUENCE: 152

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met Asn Trp Phe Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Thr Ala Asn Tyr Tyr Cys Gln Gln Ser Asn
                85                  90                  95

Ala Asp Pro Thr Phe Gly Gln Gly Thr Lys Leu Glu Ile Lys
            100                 105                 110

<210> SEQ ID NO 153
<211> LENGTH: 217
<212> TYPE: PRT
<213> ORGANISM: Artificial Sequence
<220> FEATURE:
<223> OTHER INFORMATION: 7A4D Humanized Full light chain

<400> SEQUENCE: 153

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met Asn Trp Phe Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Thr Ala Asn Tyr Tyr Cys Gln Gln Ser Asn
                85                  90                  95

Ala Asp Pro Thr Phe Gly Gln Gly Thr Lys Leu Glu Ile Lys Arg Thr
            100                 105                 110

Val Ala Ala Pro Ser Val Phe Ile Phe Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
```

-continued

```
            145                 150                 155                 160

Asn Ser Gln Glu Ser Val Thr Glu Gln Asp Ser Lys Asp Ser Thr Tyr
                    165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
        210                 215
```